US010709705B2

(12) United States Patent
Wang et al.

(10) Patent No.: US 10,709,705 B2
(45) Date of Patent: Jul. 14, 2020

(54) AMINOPYRIMIDINES AS ALK INHIBITORS

(71) Applicant: THE REGENTS OF THE UNIVERSITY OF MICHIGAN, Ann Arbor, MI (US)

(72) Inventors: Shaomeng Wang, Superior Township, MI (US); Jianyong Chen, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/559,445

(22) PCT Filed: Aug. 28, 2017

(86) PCT No.: PCT/US2017/048845
§ 371 (c)(1),
(2) Date: Sep. 19, 2017

(87) PCT Pub. No.: WO2018/044767
PCT Pub. Date: Mar. 8, 2018

(65) Prior Publication Data
US 2019/0175595 A1 Jun. 13, 2019

Related U.S. Application Data

(60) Provisional application No. 62/380,818, filed on Aug. 29, 2016.

(51) Int. Cl.
A61K 31/506 (2006.01)
C07D 405/14 (2006.01)
C07D 401/12 (2006.01)
A61P 35/00 (2006.01)

(52) U.S. Cl.
CPC ............ A61K 31/506 (2013.01); A61P 35/00 (2018.01); C07D 401/12 (2013.01); C07D 405/14 (2013.01)

(58) Field of Classification Search
CPC ............................ A61K 31/506; C07D 401/12
USPC .......................................... 514/275; 544/323
See application file for complete search history.

(56) References Cited

U.S. PATENT DOCUMENTS

| | | |
|---|---|---|
| 7,153,964 B2 | 12/2006 | Pease et al. |
| 7,893,074 B2 | 2/2011 | Garcia-Echeverria et al. |
| 7,964,592 B2 | 6/2011 | Garcia-Echeverria et al. |
| 8,039,479 B2 | 10/2011 | Michellys et al. |
| 8,377,921 B2 | 2/2013 | Michellys et al. |
| 8,592,432 B2 | 11/2013 | Chen et al. |
| 8,957,081 B2 | 2/2015 | Michellys et al. |
| 9,273,077 B2 | 3/2016 | Wang et al. |
| 2014/0024620 A1 | 1/2014 | Dalgarno et al. |

FOREIGN PATENT DOCUMENTS

| | | | |
|---|---|---|---|
| WO | WO-2012/106540 A1 | 8/2012 | |
| WO | WO-2015/081813 A1 | 6/2015 | |
| WO | WO-2015/130014 A1 | 9/2015 | |
| WO | WO2015130014 | * 9/2016 | ........... C07D 401/12 |

OTHER PUBLICATIONS

Bingham et al., Over one hundred solvates of sulfathiazole, Chem. Commun., 7:603-4 (2001).
Caira et al., Preparation and crystal characterization of a polymorph, a monohydrate, and an ethyl acetate solvate of the antifungal fluconazole, J. Pharm. Sci., 93(3):601-11 (2004).
Moss, Basic terminology of stereochemistry, Pure & Appl. Chem., 68(12):2193-222 (1996).
Pulford et al., The emerging normal and disease-related roles of anaplastic lymphoma kinase, Cell Mol. Life Sci., 61(23):2939-53 (2004).
Roskoski, Anaplastic lymphoma kinase (ALK): structure, oncogenic activation, and pharmacological inhibition, Pharmacol. Res., 68(1):68-94 (2013).
Van Tonder et al., Preparation and physicochemical characterization of 5 niclosamide solvates and 1 hemisolvate, AAPS PharmSciTech., 5(1):E12 (2004).
International Application No. PCT/US2017/048845, International Search Report and Written Opinion, dated Mar. 6, 2018.

* cited by examiner

Primary Examiner — Jeffrey H Murray
(74) Attorney, Agent, or Firm — Marshall, Gerstein & Borun LLP

(57) ABSTRACT

The present disclosure provides compounds represented by Formula I:

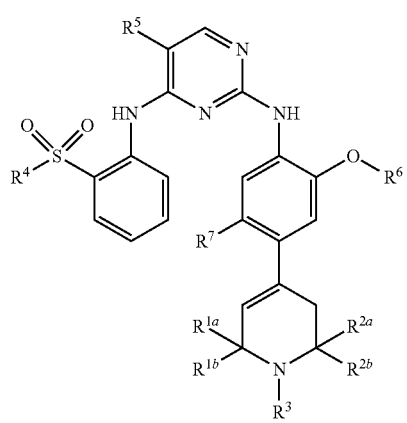

and the pharmaceutically acceptable salts, hydrates, and solvates thereof, wherein $R^{1a}$, $R^{1b}$, $R^{2a}$, $R^{2b}$, $R^3$, $R^4$, $R^5$, $R^6$, and $R^7$ are as defined as set forth in the specification. The present disclosure also provides compounds of Formula I for use to treat a condition or disorder responsive to inhibition of ALK such as cancer.

14 Claims, 1 Drawing Sheet

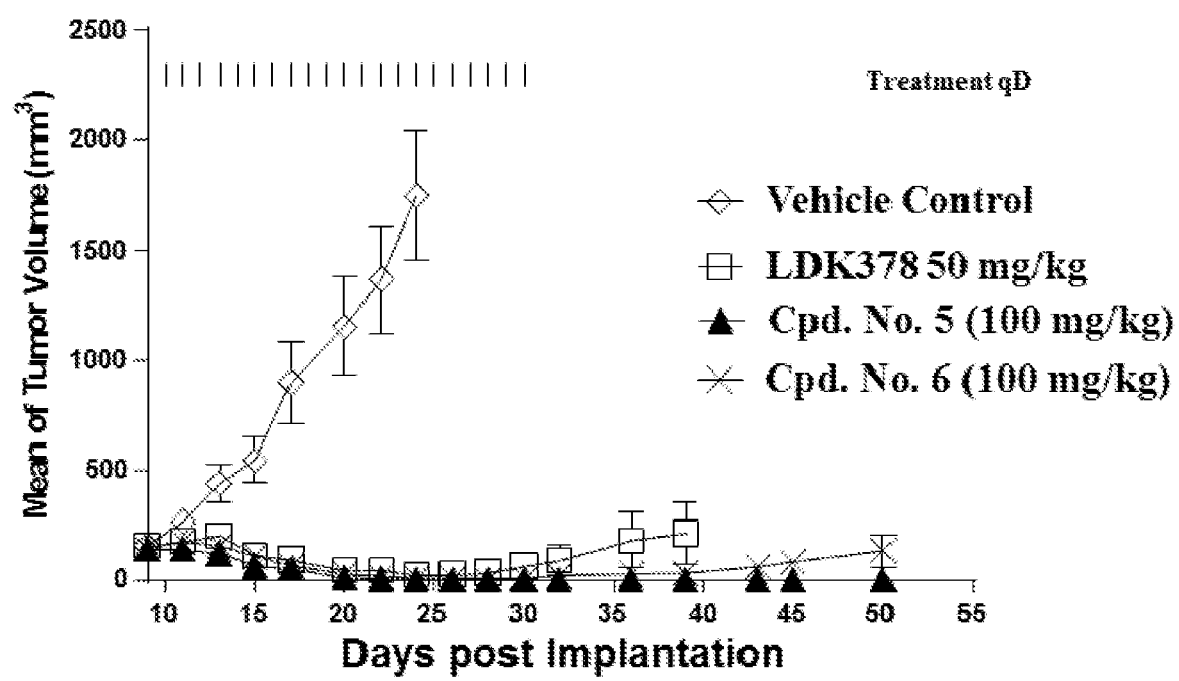

AMINOPYRIMIDINES AS ALK INHIBITORS

BACKGROUND OF THE INVENTION

Field of the Invention

The present disclosure provides anaplastic lymphoma kinase inhibitors and therapeutic methods of treating conditions and diseases wherein inhibition of anaplastic lymphoma kinase provides a benefit.

Background

Anaplastic lymphoma kinase (ALK), a member of the insulin receptor superfamily of receptor tyrosine kinases, has been implicated in oncogenesis in hematopoietic and non-hematopoietic tumors. The aberrant expression of full-length ALK receptor proteins has been reported in neuroblastomas and glioblastomas; and ALK fusion proteins have occurred in anaplastic large cell lymphoma. The study of ALK fusion proteins has also raised the possibility of new therapeutic treatments for patients with ALK-positive malignancies. Pulford et al., *Cell. Mol. Life. Sci.* 61:2939-2953 (2004).

Small molecule ALK inhibitors have therapeutic potential for the treatment of diseases and conditions in which ALK has a role, including cancer. Roskoski, *Pharmacological Research* 68:68-94 (2013). ALK inhibitors are disclosed in U.S. Pat. No. 8,039,479 and WO 2015/130014.

There is an ongoing need for new agents, e.g., small molecules, for treating and/or preventing cancer and other diseases responsive to ALK inhibition.

BRIEF SUMMARY OF THE INVENTION

In one aspect, the present disclosure provides compounds represented by any one of Formulae I-VI, below, and the pharmaceutically acceptable salts and solvates thereof, collectively referred to as "Compounds of the Disclosure." Compounds of the Disclosure are ALK inhibitors and are thus useful in treating or preventing diseases or conditions wherein ALK inhibition provides a benefit.

In another aspect, the present disclosure provides methods of treating or preventing a condition or disease by administering a therapeutically effective amount of a Compound of the Disclosure to an individual, e.g., a human, in need thereof. The disease or condition of interest is treatable or preventable by inhibition of ALK, for example, a cancer, a chronic autoimmune disorder, an inflammatory condition, a proliferative disorder, sepsis, or a viral infection. Also provided are methods of preventing the proliferation of unwanted proliferating cells, such as in cancer, in a subject comprising administering a therapeutically effective amount of a Compound of the Disclosure to a subject at risk of developing a condition characterized by unwanted proliferating cells. In some embodiments, the Compounds of the Disclosure may reduce the proliferation of unwanted cells by inducing apoptosis in those cells.

In another aspect, the present disclosure provides a method of inhibiting ALK in an individual, comprising administering to the individual an effective amount of at least one Compound of the Disclosure.

In another aspect, the present disclosure provides a pharmaceutical composition comprising a Compound of the Disclosure and an excipient and/or pharmaceutically acceptable carrier.

In another aspect, the present disclosure provides a composition comprising a Compound of the Disclosure and an excipient and/or pharmaceutically acceptable carrier for use treating or preventing diseases or conditions wherein inhibition of ALK provides a benefit, e.g., cancer.

In another aspect, the present disclosure provides a composition comprising: (a) a Compound of the Disclosure; (b) a second therapeutically active agent; and (c) optionally an excipient and/or pharmaceutically acceptable carrier.

In another aspect, the present disclosure provides a Compound of the Disclosure for use in treatment or prevention of a disease or condition of interest, e.g., cancer.

In another aspect, the present disclosure provides a use of a Compound of the Disclosure for the manufacture of a medicament for treating a disease or condition of interest, e.g., cancer.

In another aspect, the present disclosure provides a kit comprising a Compound of the Disclosure, and, optionally, a packaged composition comprising a second therapeutic agent useful in the treatment of a disease or condition of interest, and a package insert containing directions for use in the treatment of a disease or condition, e.g., cancer.

In another aspect, the present disclosure provides methods of preparing Compounds of the Disclosure.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF DRAWINGS

FIG. 1 is a line graph showing Cpd. Nos. 5 and 6 inhibit tumor growth in the KARPAS 299 xenograph model in mice.

DETAILED DESCRIPTION OF THE INVENTION

Compounds of the Disclosure are ALK inhibitors.

In one embodiment, Compounds of the Disclosure are compounds represented by Formula I:

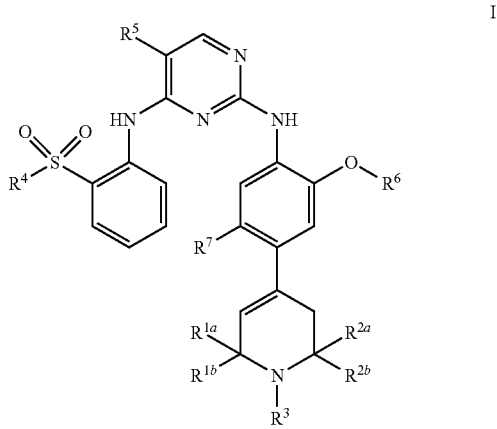

I or a pharmaceutically acceptable salt or solvate thereof, wherein:

$R^{1a}$ and $R^{1b}$ are independently selected from the group consisting of hydrogen, $C_{1-6}$ alkyl, and $C_{3-8}$ cycloalkyl;

$R^{2a}$ and $R^{2b}$ are independently selected from the group consisting of hydrogen, $C_{1-6}$ alkyl, and $C_{3-8}$ cycloalkyl;

$R^3$ is selected from the group consisting of hydrogen, $C_{1-6}$ alkyl, $C_{3-6}$ cycloalkyl, and $C_{4-8}$ heterocyclo, $R^4$ is selected from the group consisting of $C_{1-4}$ alkyl and $C_{3-6}$ cycloalkyl;

$R^5$ is halo;

$R^6$ is selected from the group consisting of $C_{1-4}$ alkyl and $C_{3-6}$ cycloalkyl; and $R^7$ is selected from the group consisting of hydrogen, $C_{1-4}$ alkyl, and $C_{3-6}$ cycloalkyl, with proviso that when $R^{1a}$, $R^{1b}$, $R^{2a}$, and $R^{2b}$ are each hydrogen, then $R^3$ is selected from the group consisting of $C_{3-6}$ cycloalkyl and $C_{4-8}$ heterocyclo.

In another embodiment, Compounds of the Disclosure are compounds represented by Formula II:

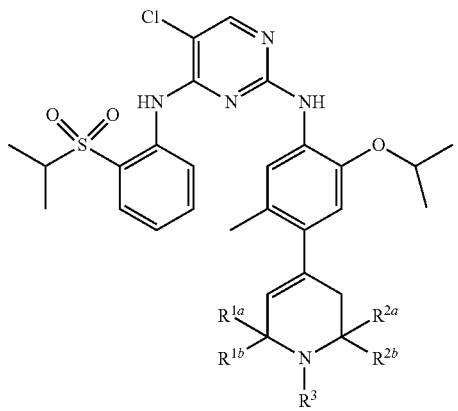

II or a pharmaceutically acceptable salt or solvate thereof, wherein:

$R^{1a}$ and $R^{1b}$ are independently selected from the group consisting of hydrogen, $C_{1-4}$ alkyl, and $C_{3-6}$ cycloalkyl;

$R^{2a}$ and $R^{2b}$ are independently selected from the group consisting of hydrogen, $C_{1-4}$ alkyl, and $C_{3-6}$ cycloalkyl; and $R^3$ is selected from the group consisting of hydrogen, $C_{1-4}$ alkyl, $C_{3-6}$ cycloalkyl, and $C_{4-8}$ heterocyclo, with proviso that when $R^{1a}$, $R^{1b}$, $R^{2a}$, and $R^{2b}$ are each hydrogen, then $R^3$ is selected from the group consisting of $C_{3-6}$ cycloalkyl and $C_{4-8}$ heterocyclo.

In another embodiment, Compounds of the Disclosure are compounds represented by Formula I or II, with proviso that when $R^{1a}$, $R^{1b}$, $R^{2a}$, and $R^{2b}$ are each hydrogen, then $R^3$ is $C_{4-8}$ heterocyclo.

In another embodiment, Compounds of the Disclosure are compounds represented by Formula I or II, or a pharmaceutically acceptable salt or solvate thereof, wherein $R^{1b}$ and $R^{2b}$ are each hydrogen.

In another embodiment, Compounds of the Disclosure are compounds represented by Formula I or II, or a pharmaceutically acceptable salt or solvate thereof, wherein $R^{1a}R^{1b}$, $R^{2a}$, and $R^{2b}$ are each hydrogen.

In another embodiment, Compounds of the Disclosure are compounds represented by Formula I or II, or a pharmaceutically acceptable salt or solvate thereof, wherein $R^{1b}$ and $R^{2b}$ are each hydrogen; and $R^{1a}$ and $R^{2a}$ are each $C_{1-4}$ alkyl. In another embodiment, $R^{1a}$ and $R^{2a}$ are each methyl. In another embodiment, $R^{1a}$ and $R^{2a}$ have a cis stereochemical relationship. In another embodiment, $R^{1a}$ and $R^{2a}$ have a trans stereochemical relationship.

In another embodiment, Compounds of the Disclosure are compounds represented by Formula I or II, or a pharmaceutically acceptable salt or solvate thereof, wherein $R^{1b}$ and $R^{2b}$ are each hydrogen; and $R^{1a}$ and $R^{2a}$ are each $C_{3-6}$ cycloalkyl. In another embodiment, $R^{1a}$ and $R^{2a}$ are each cyclopropyl. In another embodiment, $R^{1a}$ and $R^{2a}$ have a cis stereochemical relationship. In another embodiment, $R^{1a}$ and $R^{2a}$ have a trans stereochemical relationship.

In another embodiment, Compounds of the Disclosure are compounds represented by Formula I or II, or a pharmaceutically acceptable salt or solvate thereof, wherein $R^{1a}$, $R^{1b}$, $R^{2a}$, and $R^{2b}$ are each $C_{1-3}$ alkyl. In another embodiment, $R^{1a}$, $R^{1b}$, $R^{2a}$, and $R^{2b}$ are each methyl.

In another embodiment, Compounds of the Disclosure are compounds represented by Formula III:

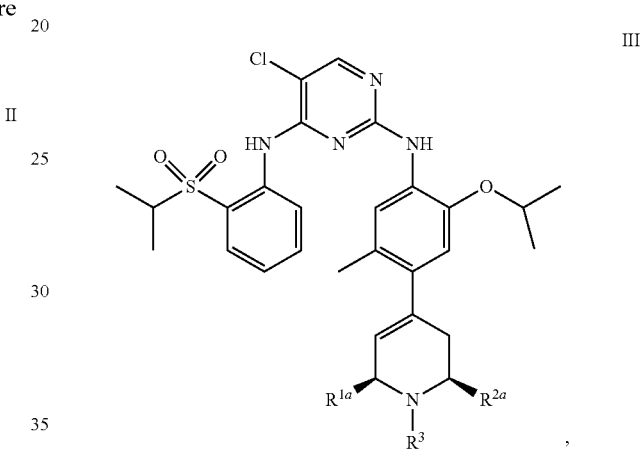

III or a pharmaceutically acceptable salt or solvate thereof, wherein the compound has an enantiomeric excess of about 90% or more; $R^{1a}$ and $R^{2a}$ are each independently $C_{1-4}$ alkyl, or $C_{3-6}$ cycloalkyl; and $R^3$ is as defined in connection with Formula II. In another embodiment, the compound has an enantiomeric excess of about 91% or more, about 92% or more, about 93% or more, about 94% or more, about 95% or more, about 96% or more, about 97% or more, about 98% or more, or about 99% or more.

In another embodiment, Compounds of the Disclosure are compounds represented by Formula IV:

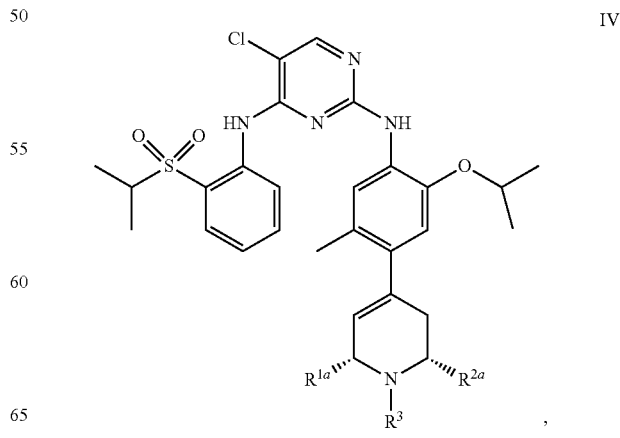

IV or a pharmaceutically acceptable salt or solvate thereof, wherein the compound has an enantiomeric excess of about 90% or more; $R^{1a}$ and $R^{2a}$ are each independently $C_{1-4}$ alkyl, or $C_{3-6}$ cycloalkyl; and $R^3$ is as defined in connection with Formula II. In another embodiment, the compound has an enantiomeric excess of about 91% or more, about 92% or more, about 93% or more, about 94% or more, about 95% or more, about 96% or more, about 97% or more, about 98% or more, or about 99% or more.

In another embodiment, Compounds of the Disclosure are compounds represented by Formula V:

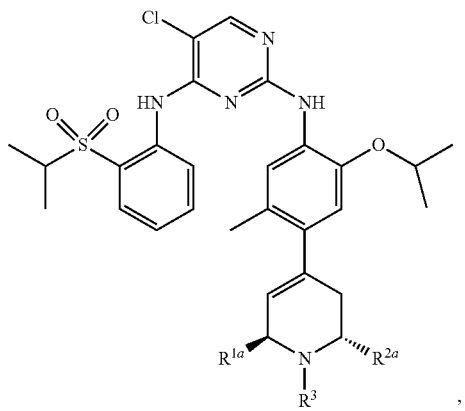

V or a pharmaceutically acceptable salt or solvate thereof, wherein the compound has an enantiomeric excess of about 90% or more; $R^{1a}$ and $R^{2a}$ are each independently $C_{1-4}$ alkyl, or $C_{3-6}$ cycloalkyl; and $R^3$ is as defined in connection with Formula II. In another embodiment, the compound has an enantiomeric excess of about 91% or more, about 92% or more, about 93% or more, about 94% or more, about 95% or more, about 96% or more, about 97% or more, about 98% or more, or about 99% or more.

In another embodiment, Compounds of the Disclosure are compounds represented by Formula VI:

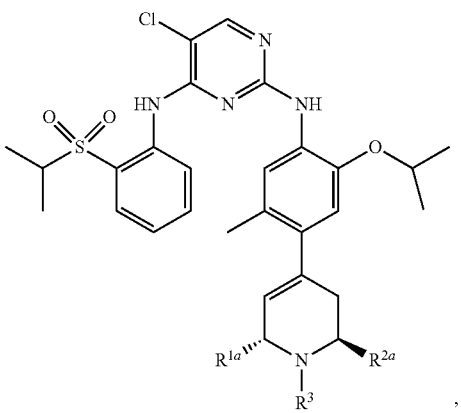

VI or a pharmaceutically acceptable salt or solvate thereof, wherein the compound has an enantiomeric excess of about 90% or more; $R^{1a}$ and $R^{2a}$ are each independently $C_{1-4}$ alkyl, or $C_{3-6}$ cycloalkyl; and $R^3$ is as defined in connection with Formula II. In another embodiment, the compound has an enantiomeric excess of about 91% or more, about 92% or more, about 93% or more, about 94% or more, about 95% or more, about 96% or more, about 97% or more, about 98% or more, or about 99% or more.

In another embodiment, Compounds of the Disclosure are compounds represented by any one of Formula III-VI, or a pharmaceutically acceptable salt or solvate thereof, wherein $R^{1a}$ and $R^{2a}$ are each $C_{1-3}$ alkyl. In another embodiment, $R^{1a}$ and $R^{2a}$ are each methyl.

In another embodiment, Compounds of the Disclosure are compounds represented by any one of Formula III-VI, or a pharmaceutically acceptable salt or solvate thereof, wherein $R^{1a}$ and $R^{2a}$ are each $C_{3-6}$ cycloalkyl. In another embodiment, $R^{1a}$ and $R^{2a}$ are each cyclopropyl.

In another embodiment, Compounds of the Disclosure are compounds represented by any one of Formula I-VI, or a pharmaceutically acceptable salt or solvate thereof, wherein $R^3$ is hydrogen.

In another embodiment, Compounds of the Disclosure are compounds represented by any one of Formula I-VI, or a pharmaceutically acceptable salt or solvate thereof, wherein $R^3$ is $C_{1-3}$ alkyl. In another embodiment, $R^3$ is methyl.

In another embodiment, Compounds of the Disclosure are compounds represented by any one of Formula I-VI, or a pharmaceutically acceptable salt or solvate thereof, wherein $R^3$ is $C_{3-6}$ heterocyclo. In another embodiment, $R^3$ is $C_{3-6}$ heterocyclo selected from the group consisting of:

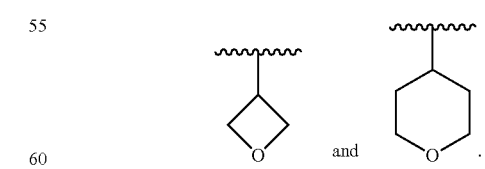

In another embodiment, Compounds of the Disclosure are compounds of Table 1, and the pharmaceutically acceptable salts and solvates thereof. The compounds of Table 1 are racemates.

TABLE 1

| Cpd. No. | Structure | Name |
|---|---|---|
| 1 | 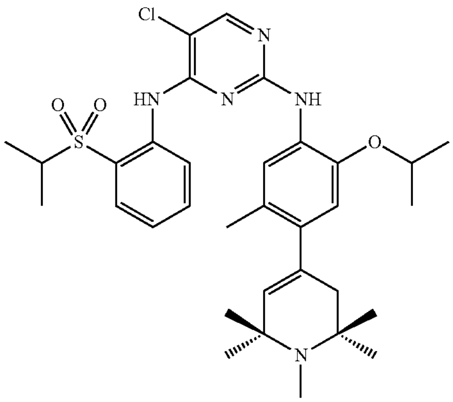 | 5-chloro-N2-(2-isopropoxy-5-methyl-4-(1,2,2,6,6-pentamethyl-1,2,3,6-tetrahydropyridin-4-yl)phenyl)-N4-(2-(isopropylsulfonyl)phenyl)pyrimidine-2,4-diamine |
| 2 | 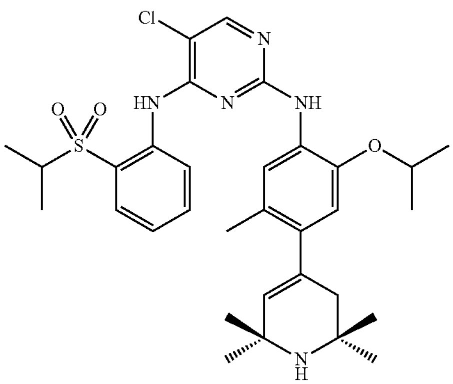 | 5-chloro-N2-(2-isopropoxy-5-methyl-4-(2,2,6,6-tetramethyl-1,2,3,6-tetrahydropyridin-4-yl)phenyl)-N4-(2-(isopropylsulfonyl)phenyl)pyrimidine-2,4-diamine |
| 3 | 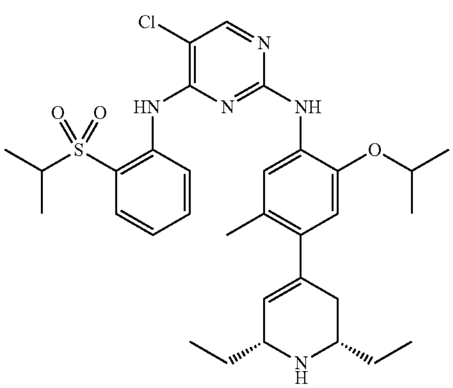 [SMILES: CC[C@H]1CC(c2cc(OC(C)C)c(Nc3ncc(Cl)c(Nc4ccccc4S(=O)(=O)C(C)C)n3)cc2C)=C[C@@H](CC)N1] | 5-chloro-N2-(4-((cis)-2,6-diethyl-1,2,3,6-tetrahydropyridin-4-yl)-2-isopropoxy-5-methylphenyl)-N4-(2-(isopropylsulfonyl)phenyl)pyrimidine-2,4-diamine |
| 4 | 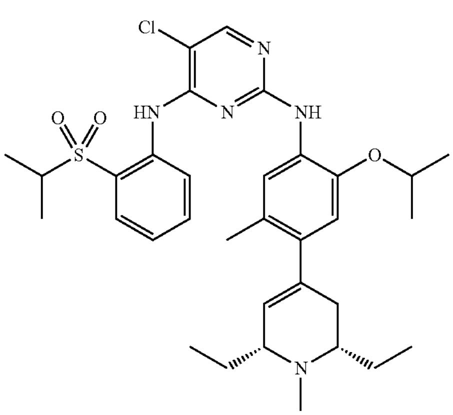 [SMILES: CC[C@H]1CC(c2cc(OC(C)C)c(Nc3ncc(Cl)c(Nc4ccccc4S(=O)(=O)C(C)C)n3)cc2C)=C[C@@H](CC)N1C] | 5-chloro-N2-(4-((cis)-2,6-diethyl-1-methyl-1,2,3,6-tetrahydropyridin-4-yl)-2-isopropoxy-5-methylphenyl)-N4-(2-(isopropylsulfonyl)phenyl)pyrimidine-2,4-diamine |

TABLE 1-continued

| Cpd. No. | Structure | Name |
|---|---|---|
| 5 | 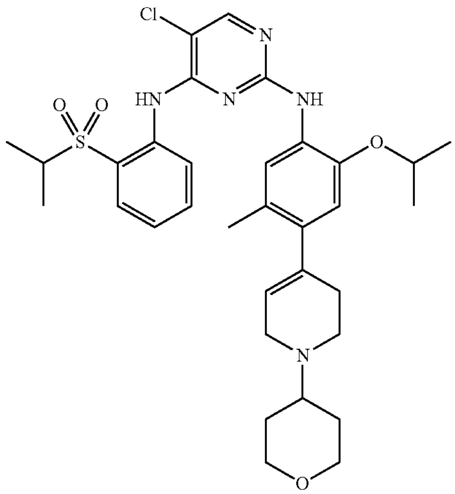 [SMILES: Cc1cc(Nc2ncc(Cl)c(Nc3ccccc3S(=O)(=O)C(C)C)n2)c(OC(C)C)cc1C1=CCN(C2CCOCC2)CC1] | 5-chloro-N2-(2-isopropoxy-5-methyl-4-(1-(tetrahydro-2H-pyran-4-yl)-1,2,3,6-tetrahydropyridin-4-yl)phenyl)-N4-(2-(isopropylsulfonyl)phenyl)pyrimidine-2,4-diamine |
| 6 | 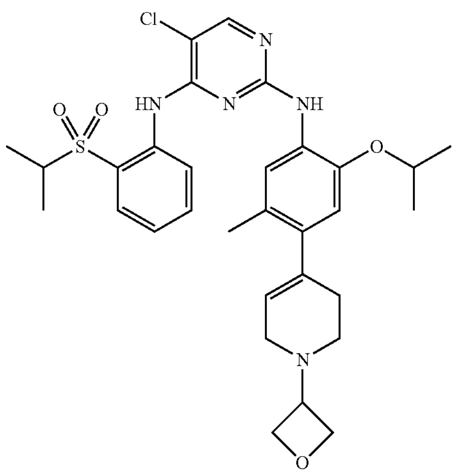 [SMILES: Cc1cc(Nc2ncc(Cl)c(Nc3ccccc3S(=O)(=O)C(C)C)n2)c(OC(C)C)cc1C1=CCN(C2COC2)CC1] | 5-chloro-N2-(2-isopropoxy-5-methyl-4-(1-(oxetan-3-yl)-1,2,3,6-tetrahydropyridin-4-yl)phenyl)-N4-(2-(isopropylsulfonyl)phenyl)pyrimidine-2,4-diamine |
| 7 | 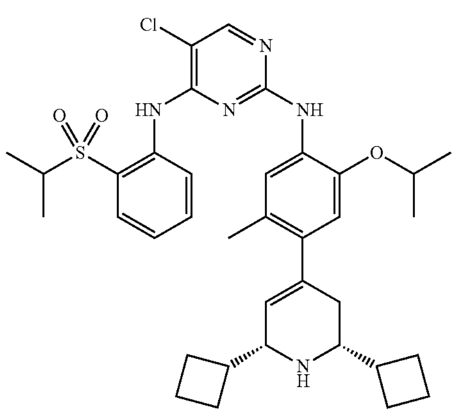 [SMILES: Cc1cc(Nc2ncc(Cl)c(Nc3ccccc3S(=O)(=O)C(C)C)n2)c(OC(C)C)cc1C1=C[C@@H](C2CCC2)N[C@@H](C2CCC2)C1] | 5-chloro-N2-(4-((cis)-2,6-dicyclobutyl-1,2,3,6-tetrahydropyridin-4-yl)-2-isopropoxy-5-methylphenyl)-N4-(2-(isopropylsulfonyl)phenyl)pyrimidine-2,4-diamine |

TABLE 1-continued

| Cpd. No. | Structure | Name |
|---|---|---|
| 8 | 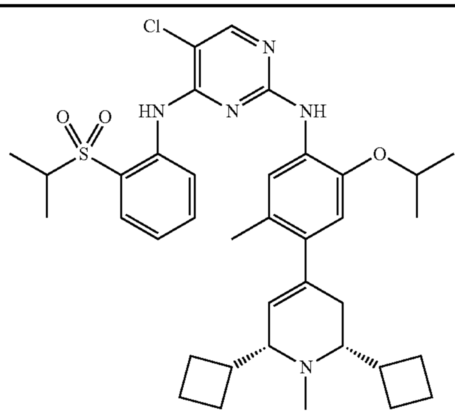 | 5-chloro-N2-(4-((cis)-2,6-dicyclobutyl-1-methyl-1,2,3,6-tetrahydropyridin-4-yl)-2-isopropoxy-5-methylphenyl)-N4-(2-(isopropylsulfonyl)phenyl)pyrimidine-2,4-diamine |
| 9 | 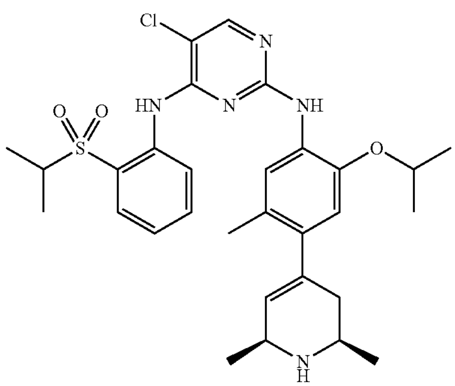 [SMILES: Cc1cc(Nc2ncc(Cl)c(Nc3ccccc3S(=O)(=O)C(C)C)n2)c(OC(C)C)cc1C1=C[C@H](C)N[C@H](C)C1] | 5-chloro-N2-(4-((cis)-2,6-dimethyl-1,2,3,6-tetrahydropyridin-4-yl)-2-isopropoxy-5-methylphenyl)-N4-(2-(isopropylsulfonyl)phenyl)pyrimidine-2,4-diamine |
| 10 | 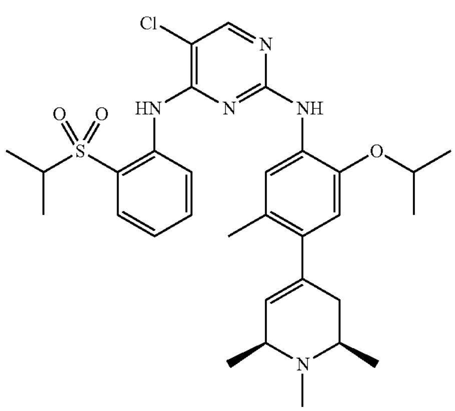 [SMILES: Cc1cc(Nc2ncc(Cl)c(Nc3ccccc3S(=O)(=O)C(C)C)n2)c(OC(C)C)cc1C1=C[C@H](C)N(C)[C@H](C)C1] | 5-chloro-N2-(2-isopropoxy-5-methyl-4-((cis)-1,2,6-trimethyl-1,2,3,6-tetrahydropyridin-4-yl)phenyl)-N4-(2-(isopropylsulfonyl)phenyl)pyrimidine-2,4-diamine |
| 11 | 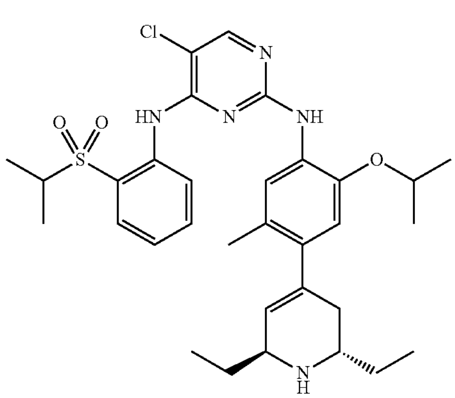 [SMILES: CC[C@H]1CC(c2cc(OC(C)C)c(Nc3ncc(Cl)c(Nc4ccccc4S(=O)(=O)C(C)C)n3)cc2C)=C[C@H](CC)N1] | 5-chloro-N2-(4-((trans)-2,6-diethyl-1,2,3,6-tetrahydropyridin-4-yl)-2-isopropoxy-5-methylphenyl)-N4-(2-(isopropylsulfonyl)phenyl)pyrimidine-2,4-diamine |

TABLE 1-continued

| Cpd. No. | Structure | Name |
|---|---|---|
| 12 | 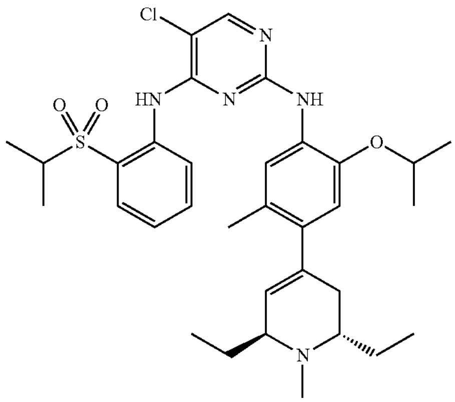 [SMILES: CC[C@H]1CC(c2cc(OC(C)C)c(Nc3ncc(Cl)c(Nc4ccccc4S(=O)(=O)C(C)C)n3)cc2C)=C[C@H](CC)N1C] | 5-chloro-N2-(4-((trans)-2,6-diethyl-1-methyl-1,2,3,6-tetrahydropyridin-4-yl)-2-isopropoxy-5-methylphenyl)-N4-(2-(isopropylsulfonyl)phenyl)pyrimidine-2,4-diamine |
| 13 | 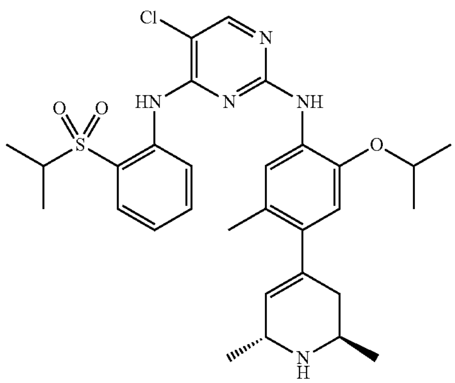 [SMILES: Cc1cc(Nc2ncc(Cl)c(Nc3ccccc3S(=O)(=O)C(C)C)n2)c(OC(C)C)cc1C1=C[C@@H](C)N[C@H](C)C1] | 5-chloro-N2-(4-((trans)-2,6-dimethyl-1,2,3,6-tetrahydropyridin-4-yl)-2-isopropoxy-5-methylphenyl)-N4-(2-(isopropylsulfonyl)phenyl)pyrimidine-2,4-diamine |
| 14 | 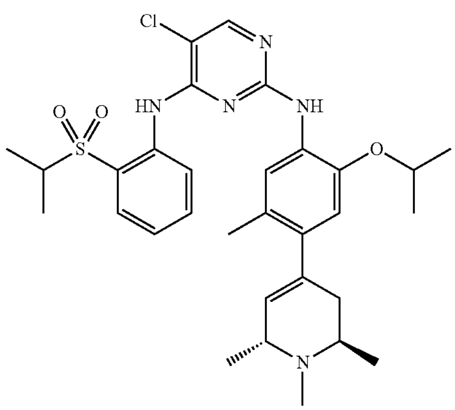 [SMILES: Cc1cc(Nc2ncc(Cl)c(Nc3ccccc3S(=O)(=O)C(C)C)n2)c(OC(C)C)cc1C1=C[C@@H](C)N(C)[C@H](C)C1] | 5-chloro-N2-(2-isopropoxy-5-methyl-4-((trans)-1,2,6-trimethyl-1,2,3,6-tetrahydropyridin-4-yl)phenyl)-N4-(2-(isopropylsulfonyl)phenyl)pyrimidine-2,4-diamine |
| 15 | 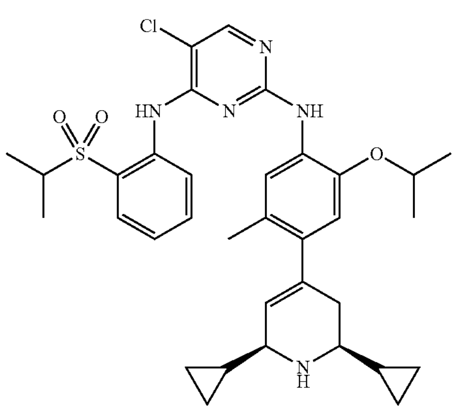 [SMILES: Cc1cc(Nc2ncc(Cl)c(Nc3ccccc3S(=O)(=O)C(C)C)n2)c(OC(C)C)cc1C1=C[C@H](C2CC2)N[C@H](C2CC2)C1] | 5-chloro-N2-(4-((cis)-2,6-dicyclopropyl-1,2,3,6-tetrahydropyridin-4-yl)-2-isopropoxy-5-methylphenyl)-N4-(2-(isopropylsulfonyl)phenyl)pyrimidine-2,4-diamine |

TABLE 1-continued

| Cpd. No. | Structure | Name |
|---|---|---|
| 16 | 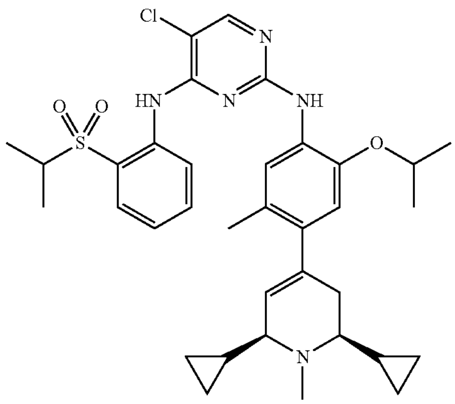 [SMILES: Cc1cc(Nc2ncc(Cl)c(Nc3ccccc3S(=O)(=O)C(C)C)n2)c(OC(C)C)cc1C1=C[C@H](C2CC2)N(C)[C@H](C2CC2)C1] | 5-chloro-N2-(4-((cis)-2,6-dicyclopropyl-1-methyl-1,2,3,6-tetrahydropyridin-4-yl)-2-isopropoxy-5-methylphenyl)-N4-(2-(isopropylsulfonyl)phenyl)pyrimidine-2,4-diamine |
| 17 | 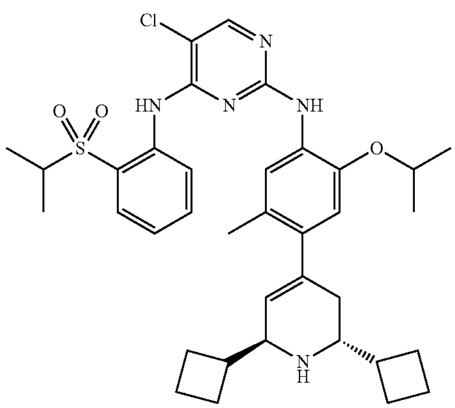 [SMILES: Cc1cc(Nc2ncc(Cl)c(Nc3ccccc3S(=O)(=O)C(C)C)n2)c(OC(C)C)cc1C1=C[C@H](C2CCC2)N[C@@H](C2CCC2)C1] | 5-chloro-N2-(4-((trans)-2,6-dicyclobutyl-1,2,3,6-tetrahydropyridin-4-yl)-2-isopropoxy-5-methylphenyl)-N4-(2-(isopropylsulfonyl)phenyl)pyrimidine-2,4-diamine |
| 18 | 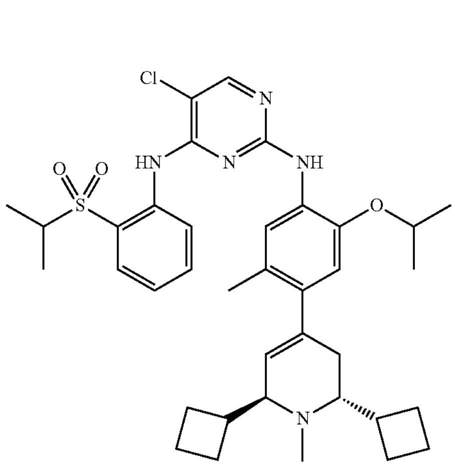 [SMILES: Cc1cc(Nc2ncc(Cl)c(Nc3ccccc3S(=O)(=O)C(C)C)n2)c(OC(C)C)cc1C1=C[C@H](C2CCC2)N(C)[C@@H](C2CCC2)C1] | 5-chloro-N2-(4-((trans)-2,6-dicyclobutyl-1-methyl-1,2,3,6-tetrahydropyridin-4-yl)-2-isopropoxy-5-methylphenyl)-N4-(2-(isopropylsulfonyl)phenyl)pyrimidine-2,4-diamine |

TABLE 1-continued

| Cpd. No. | Structure | Name |
|---|---|---|
| 19 | 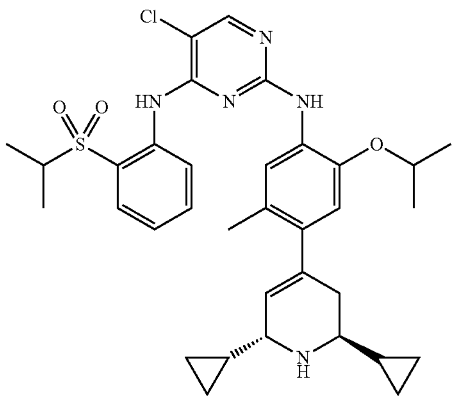 [SMILES: Cc1cc(Nc2ncc(Cl)c(Nc3ccccc3S(=O)(=O)C(C)C)n2)c(OC(C)C)cc1C1=C[C@@H](C2CC2)N[C@H](C2CC2)C1] | 5-chloro-N2-(4-((trans)-2,6-dicyclopropyl-1,2,3,6-tetrahydropyridin-4-yl)-2-isopropoxy-5-methylphenyl)-N4-(2-(isopropylsulfonyl)phenyl)pyrimidine-2,4-diamine |
| 20 | 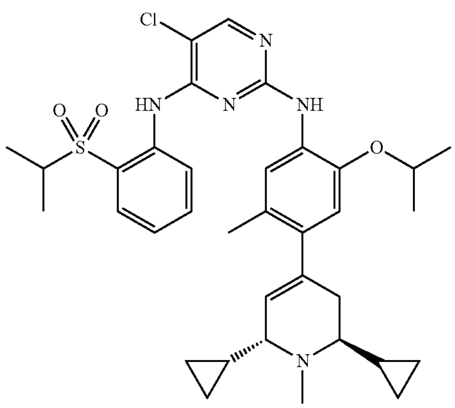 [SMILES: Cc1cc(Nc2ncc(Cl)c(Nc3ccccc3S(=O)(=O)C(C)C)n2)c(OC(C)C)cc1C1=C[C@@H](C2CC2)N(C)[C@H](C2CC2)C1] | 5-chloro-N2-(4-((trans)-2,6-dicyclopropyl-1-methyl-1,2,3,6-tetrahydropyridin-4-yl)-2-isopropoxy-5-methylphenyl)-N4-(2-(isopropylsulfonyl)phenyl)pyrimidine-2,4-diamine |
| 21 | 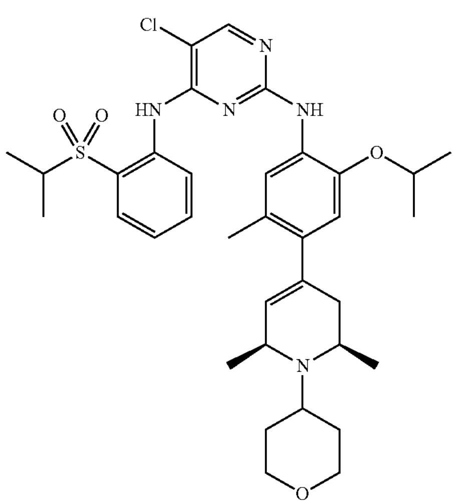 [SMILES: Cc1cc(Nc2ncc(Cl)c(Nc3ccccc3S(=O)(=O)C(C)C)n2)c(OC(C)C)cc1C1=C[C@H](C)N(C2CCOCC2)[C@H](C)C1] | 5-chloro-N2-(4-((cis)-2,6-dimethyl-1-(tetrahydro-2H-pyran-4-yl)-1,2,3,6-tetrahydropyridin-4-yl)-2-isopropoxy-5-methylphenyl)-N4-(2-(isopropylsulfonyl)phenyl)pyrimidine-2,4-diamine |

TABLE 1-continued

| Cpd. No. | Structure | Name |
|---|---|---|
| 22 | 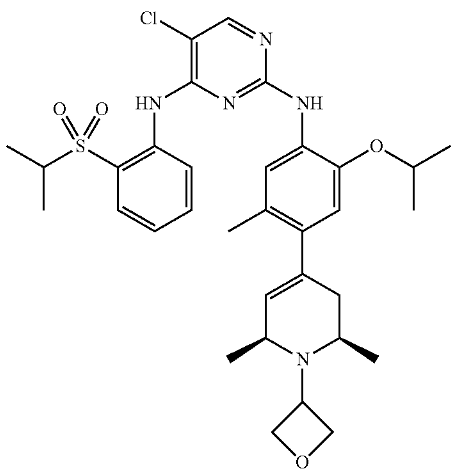 [SMILES: Cc1cc(Nc2ncc(Cl)c(Nc3ccccc3S(=O)(=O)C(C)C)n2)c(OC(C)C)cc1C1=C[C@H](C)N(C2COC2)[C@H](C)C1] | 5-chloro-N2-(4-((cis)-2,6-dimethyl-1-(oxetan-3-yl)-1,2,3,6-tetrahydropyridin-4-yl)-2-isopropoxy-5-methylphenyl)-N4-(2-(isopropylsulfonyl)phenyl)pyrimidine-2,4-diamine |
| 23 | 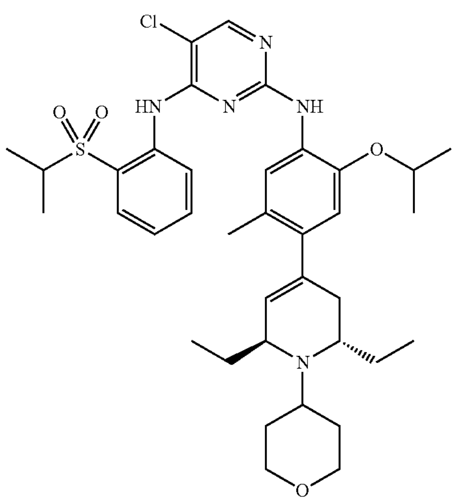 [SMILES: CC[C@H]1CC(c2cc(OC(C)C)c(Nc3ncc(Cl)c(Nc4ccccc4S(=O)(=O)C(C)C)n3)cc2C)=C[C@H](CC)N1C1CCOCC1] | 5-chloro-N2-(4-((trans)-2,6-diethyl-1-(tetrahydro-2H-pyran-4-yl)-1,2,3,6-tetrahydropyridin-4-yl)-2-isopropoxy-5-methylphenyl)-N4-(2-(isopropylsulfonyl)phenyl)pyrimidine-2,4-diamine |
| 24 | 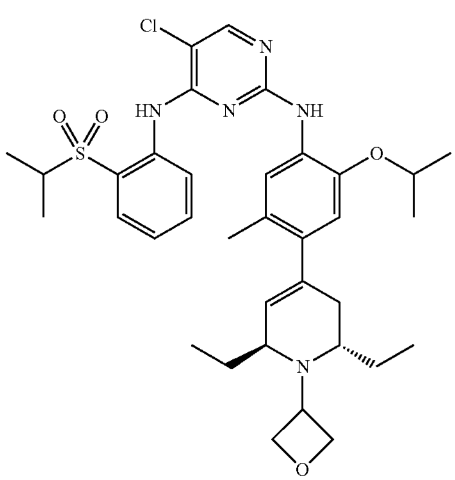 [SMILES: CC[C@H]1CC(c2cc(OC(C)C)c(Nc3ncc(Cl)c(Nc4ccccc4S(=O)(=O)C(C)C)n3)cc2C)=C[C@H](CC)N1C1COC1] | 5-chloro-N2-(4-((2S,6S)-2,6-diethyl-1-(oxetan-3-yl)-1,2,3,6-tetrahydropyridin-4-yl)-2-isopropoxy-5-methylphenyl)-N4-(2-(isopropylsulfonyl)phenyl)pyrimidine-2,4-diamine |

TABLE 1-continued

| Cpd. No. | Structure | Name |
|---|---|---|
| 25 | 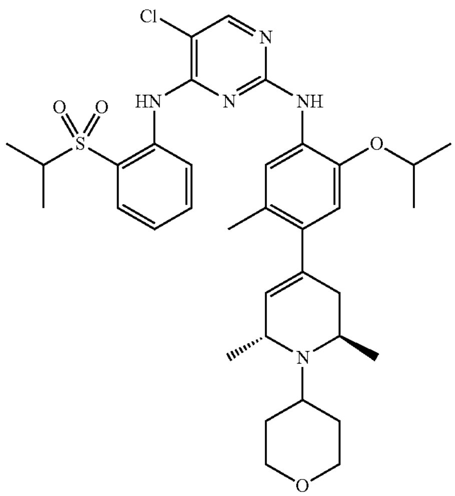 [SMILES: Cc1cc(Nc2ncc(Cl)c(Nc3ccccc3S(=O)(=O)C(C)C)n2)c(OC(C)C)cc1C1=C[C@@H](C)N(C2CCOCC2)[C@H](C)C1] | 5-chloro-N2-(4-((trans)-2,6-dimethyl-1-(tetrahydro-2H-pyran-4-yl)-1,2,3,6-tetrahydropyridin-4-yl)-2-isopropoxy-5-methylphenyl)-N4-(2-(isopropylsulfonyl)phenyl)pyrimidine-2,4-diamine |
| 26 | 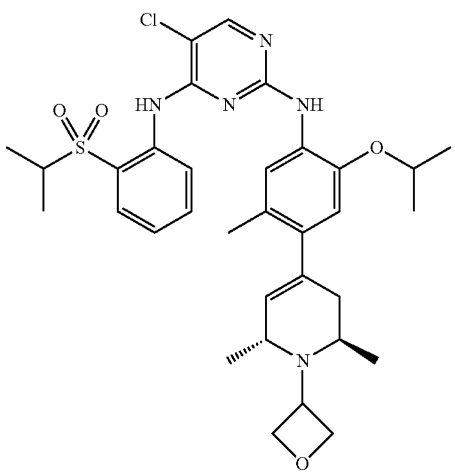 [SMILES: Cc1cc(Nc2ncc(Cl)c(Nc3ccccc3S(=O)(=O)C(C)C)n2)c(OC(C)C)cc1C1=C[C@@H](C)N(C2COC2)[C@H](C)C1] | 5-chloro-N2-(4-((trans)-2,6-dimethyl-1-(oxetan-3-yl)-1,2,3,6-tetrahydropyridin-4-yl)-2-isopropoxy-5-methylphenyl)-N4-(2-(isopropylsulfonyl)phenyl)pyrimidine-2,4-diamine |
| 27 | 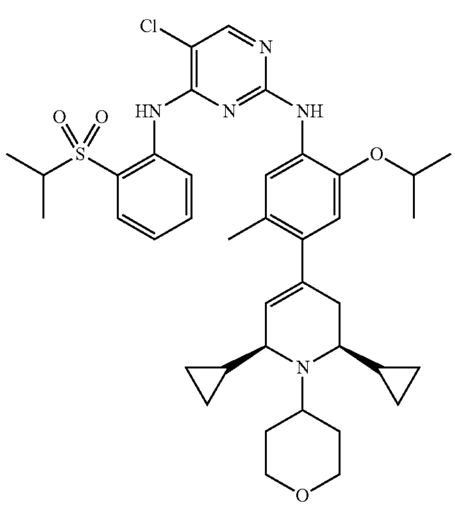 [SMILES: Cc1cc(Nc2ncc(Cl)c(Nc3ccccc3S(=O)(=O)C(C)C)n2)c(OC(C)C)cc1C1=C[C@H](C2CC2)N(C2CCOCC2)[C@H](C2CC2)C1] | 5-chloro-N2-(4-((cis)-2,6-dicyclopropyl-1-(tetrahydro-2H-pyran-4-yl)-1,2,3,6-tetrahydropyridin-4-yl)-2-isopropoxy-5-methylphenyl)-N4-(2-(isopropylsulfonyl)phenyl)pyrimidine-2,4-diamine |

TABLE 1-continued

| Cpd. No. | Structure | Name |
|---|---|---|
| 28 | 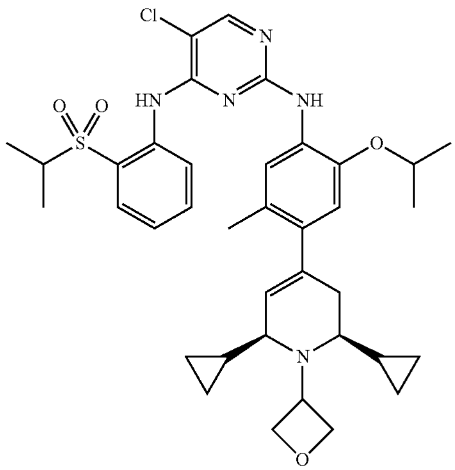 [SMILES: Cc1cc(Nc2ncc(Cl)c(Nc3ccccc3S(=O)(=O)C(C)C)n2)c(OC(C)C)cc1C1=C[C@H](C2CC2)N(C2COC2)[C@H](C2CC2)C1] | 5-chloro-N2-(4-((cis)-2,6-dicyclopropyl-1-(oxetan-3-yl)-1,2,3,6-tetrahydropyridin-4-yl)-2-isopropoxy-5-methylphenyl)-N4-(2-(isopropylsulfonyl)phenyl)pyrimidine-2,4-diamine |
| 29 | 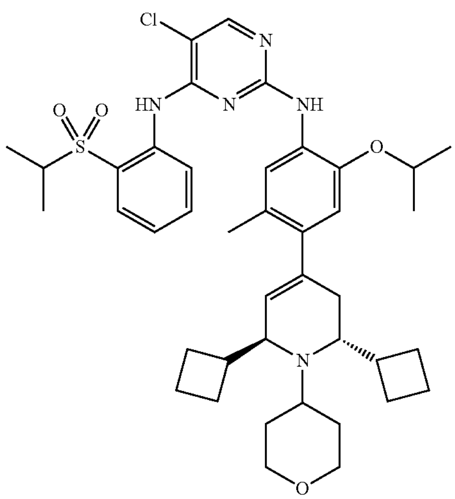 [SMILES: Cc1cc(Nc2ncc(Cl)c(Nc3ccccc3S(=O)(=O)C(C)C)n2)c(OC(C)C)cc1C1=C[C@H](C2CCC2)N(C2CCOCC2)[C@@H](C2CCC2)C1] | 5-chloro-N2-(4-((trans)-2,6-dicyclobutyl-1-(tetrahydro-2H-pyran-4-yl)-1,2,3,6-tetrahydropyridin-4-yl)-2-isopropoxy-5-methylphenyl)-N4-(2-(isopropylsulfonyl)phenyl)pyrimidine-2,4-diamine |
| 30 | 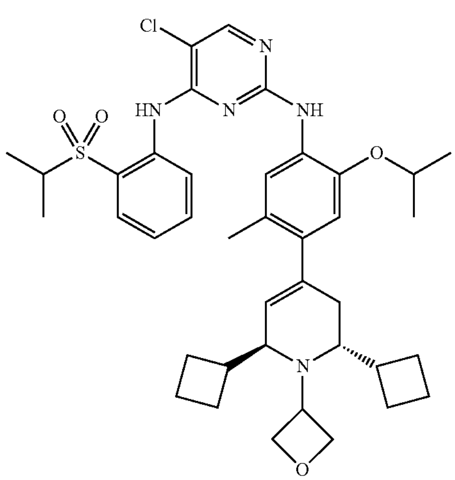 [SMILES: Cc1cc(Nc2ncc(Cl)c(Nc3ccccc3S(=O)(=O)C(C)C)n2)c(OC(C)C)cc1C1=C[C@H](C2CCC2)N(C2COC2)[C@@H](C2CCC2)C1] | 5-chloro-N2-(4-((trans)-2,6-dicyclobutyl-1-(oxetan-3-yl)-1,2,3,6-tetrahydropyridin-4-yl)-2-isopropoxy-5-methylphenyl)-N4-(2-(isopropylsulfonyl)phenyl)pyrimidine-2,4-diamine |

TABLE 1-continued

| Cpd. No. | Structure | Name |
|---|---|---|
| 31 | 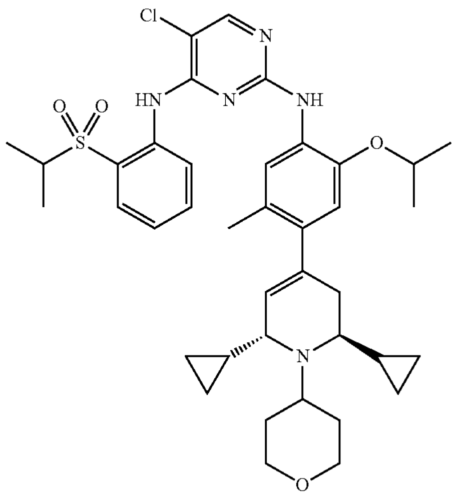 [SMILES: Cc1cc(Nc2ncc(Cl)c(Nc3ccccc3S(=O)(=O)C(C)C)n2)c(OC(C)C)cc1C1=C[C@@H](C2CC2)N(C2CCOCC2)[C@H](C2CC2)C1] | 5-chloro-N2-(4-((trans)-2,6-dicyclopropyl-1-(tetrahydro-2H-pyran-4-yl)-1,2,3,6-tetrahydropyridin-4-yl)-2-isopropoxy-5-methylphenyl)-N4-(2-(isopropylsulfonyl)phenyl)pyrimidine-2,4-diamine |
| 32 | 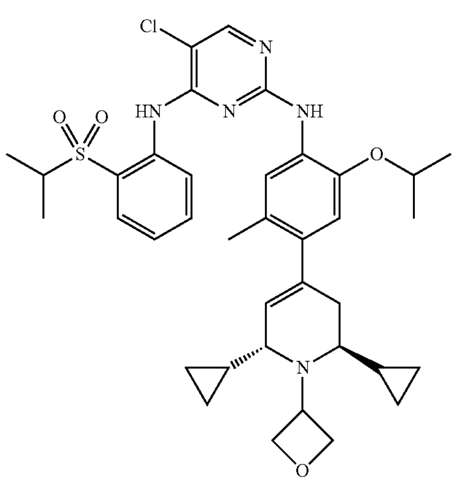 [SMILES: Cc1cc(Nc2ncc(Cl)c(Nc3ccccc3S(=O)(=O)C(C)C)n2)c(OC(C)C)cc1C1=C[C@@H](C2CC2)N(C2COC2)[C@H](C2CC2)C1] | 5-chloro-N2-(4-((trans)-2,6-dicyclopropyl-1-(oxetan-3-yl)-1,2,3,6-tetrahydropyridin-4-yl)-2-isopropoxy-5-methylphenyl)-N4-(2-(isopropylsulfonyl)phenyl)pyrimidine-2,4-diamine |

In another embodiment, Compounds of the Disclosure are compounds of Table 2, and the pharmaceutically acceptable salts and solvates thereof. The compounds of Table 2 are enantiomerically enriched.

TABLE 2

| Cpd. No. | Structure | Name |
|---|---|---|
| 33 | 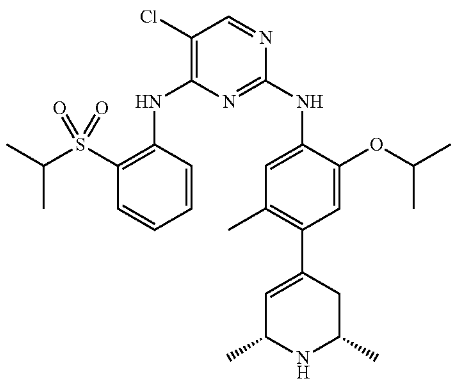 [SMILES: Cc1cc(Nc2ncc(Cl)c(Nc3ccccc3S(=O)(=O)C(C)C)n2)c(OC(C)C)cc1C1=C[C@@H](C)N[C@@H](C)C1] | 5-chloro-N2-(4-((2S,6R)-2,6-dimethyl-1,2,3,6-tetrahydropyridin-4-yl)-2-isopropoxy-5-methylphenyl)-N4-(2-(isopropylsulfonyl)phenyl)pyrimidine-2,4-diamine |
| 34 | 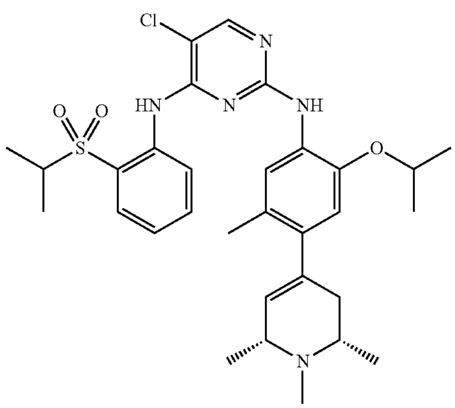 [SMILES: Cc1cc(Nc2ncc(Cl)c(Nc3ccccc3S(=O)(=O)C(C)C)n2)c(OC(C)C)cc1C1=C[C@@H](C)N(C)[C@@H](C)C1] | 5-chloro-N2-(2-isopropoxy-5-methyl-4-((2S,6R)-1,2,6-trimethyl-1,2,3,6-tetrahydropyridin-4-yl)phenyl)-N4-(2-(isopropylsulfonyl)phenyl)pyrimidine-2,4-diamine |
| 35 | 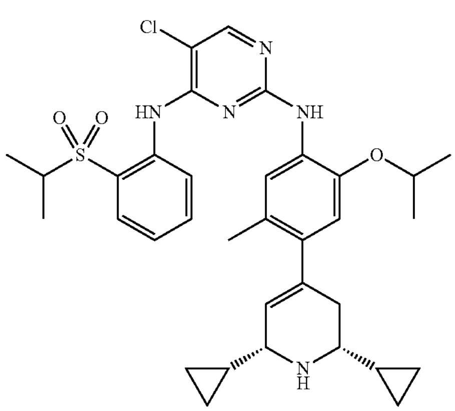 [SMILES: Cc1cc(Nc2ncc(Cl)c(Nc3ccccc3S(=O)(=O)C(C)C)n2)c(OC(C)C)cc1C1=C[C@@H](C2CC2)N[C@@H](C2CC2)C1] | 5-chloro-N2-(4-((2R,6R)-2,6-dicyclopropyl-1,2,3,6-tetrahydropyridin-4-yl)-2-isopropoxy-5-methylphenyl)-N4-(2-(isopropylsulfonyl)phenyl)pyrimidine-2,4-diamine |

TABLE 2-continued

| Cpd. No. | Structure | Name |
| --- | --- | --- |
| 36 | 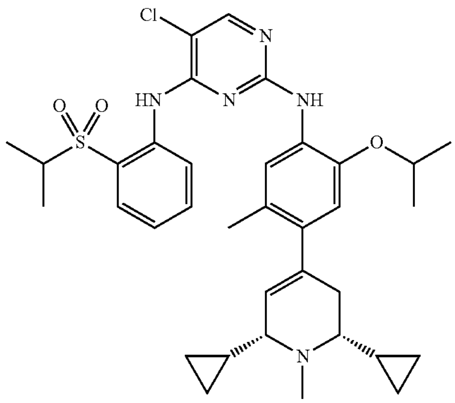 [SMILES: Cc1cc(Nc2ncc(Cl)c(Nc3ccccc3S(=O)(=O)C(C)C)n2)c(OC(C)C)cc1C1=C[C@@H](C2CC2)N(C)[C@@H](C2CC2)C1] | 5-chloro-N2-(4-((2R,6R)-2,6-dicyclopropyl-1-methyl-1,2,3,6-tetrahydropyridin-4-yl)-2-isopropoxy-5-methylphenyl)-N4-(2-(isopropylsulfonyl)phenyl)pyrimidine-2,4-diamine |
| 37 | 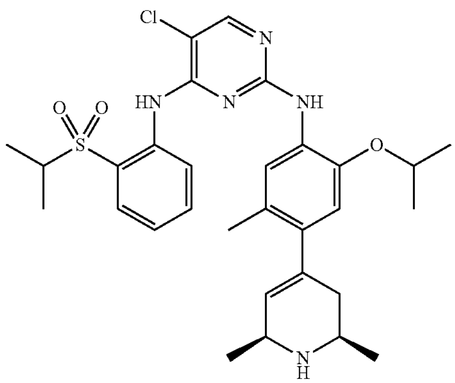 [SMILES: Cc1cc(Nc2ncc(Cl)c(Nc3ccccc3S(=O)(=O)C(C)C)n2)c(OC(C)C)cc1C1=C[C@H](C)N[C@H](C)C1] | 5-chloro-N2-(4-((2R,6S)-2,6-dimethyl-1,2,3,6-tetrahydropyridin-4-yl)-2-isopropoxy-5-methylphenyl)-N4-(2-(isopropylsulfonyl)phenyl)pyrimidine-2,4-diamine |
| 38 | 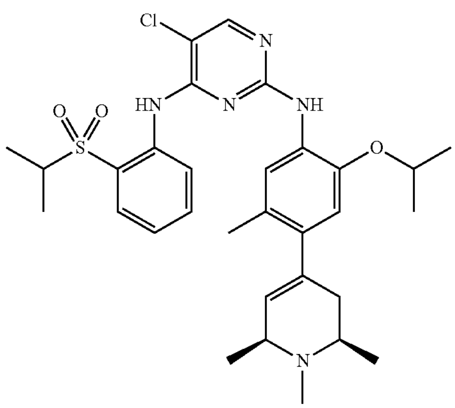 [SMILES: Cc1cc(Nc2ncc(Cl)c(Nc3ccccc3S(=O)(=O)C(C)C)n2)c(OC(C)C)cc1C1=C[C@H](C)N(C)[C@H](C)C1] | 5-chloro-N2-(2-isopropoxy-5-methyl-4-((2R,6S)-1,2,6-trimethyl-1,2,3,6-tetrahydropyridin-4-yl)phenyl)-N4-(2-(isopropylsulfonyl)phenyl)pyrimidine-2,4-diamine |
| 39 | 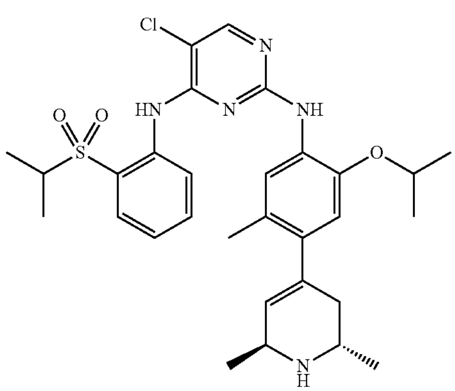 [SMILES: Cc1cc(Nc2ncc(Cl)c(Nc3ccccc3S(=O)(=O)C(C)C)n2)c(OC(C)C)cc1C1=C[C@H](C)N[C@@H](C)C1] | 5-chloro-N2-(4-((2S,6S)-2,6-dimethyl-1,2,3,6-tetrahydropyridin-4-yl)-2-isopropoxy-5-methylphenyl)-N4-(2-(isopropylsulfonyl)phenyl)pyrimidine-2,4-diamine |

TABLE 2-continued

| Cpd. No. | Structure | Name |
|---|---|---|
| 40 | 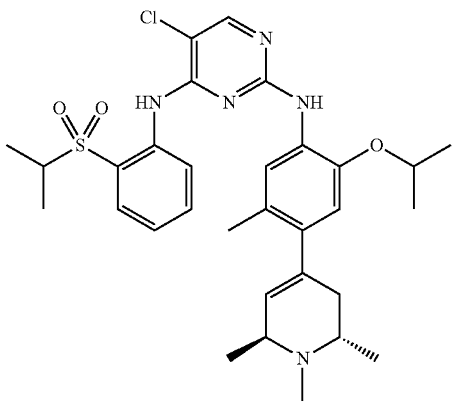 [SMILES: Cc1cc(Nc2ncc(Cl)c(Nc3ccccc3S(=O)(=O)C(C)C)n2)c(OC(C)C)cc1C1=C[C@H](C)N(C)[C@@H](C)C1] | 5-chloro-N2-(2-isopropoxy-5-methyl-4-((2S,6S)-1,2,6-trimethyl-1,2,3,6-tetrahydropyridin-4-yl)phenyl)-N4-(2-(isopropylsulfonyl)phenyl)pyrimidine-2,4-diamine |
| 41 | 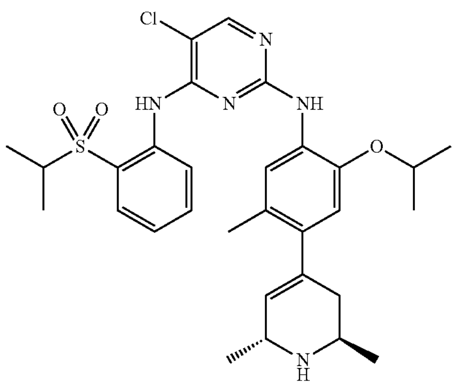 [SMILES: Cc1cc(Nc2ncc(Cl)c(Nc3ccccc3S(=O)(=O)C(C)C)n2)c(OC(C)C)cc1C1=C[C@@H](C)N[C@H](C)C1] | 5-chloro-N2-(4-((2R,6R)-2,6-dimethyl-1,2,3,6-tetrahydropyridin-4-yl)-2-isopropoxy-5-methylphenyl)-N4-(2-(isopropylsulfonyl)phenyl)pyrimidine-2,4-diamine |
| 42 | 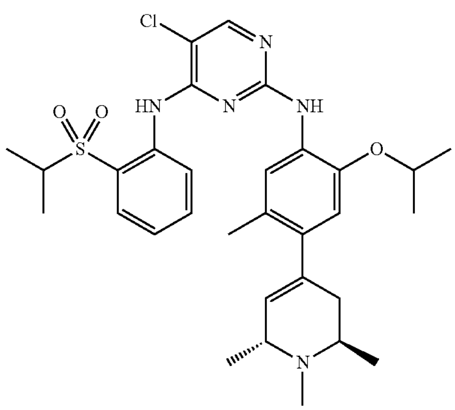 [SMILES: Cc1cc(Nc2ncc(Cl)c(Nc3ccccc3S(=O)(=O)C(C)C)n2)c(OC(C)C)cc1C1=C[C@@H](C)N(C)[C@H](C)C1] | 5-chloro-N2-(2-isopropoxy-5-methyl-4-((2R,6R)-1,2,6-trimethyl-1,2,3,6-tetrahydropyridin-4-yl)phenyl)-N4-(2-(isopropylsulfonyl)phenyl)pyrimidine-2,4-diamine |
| 43 | 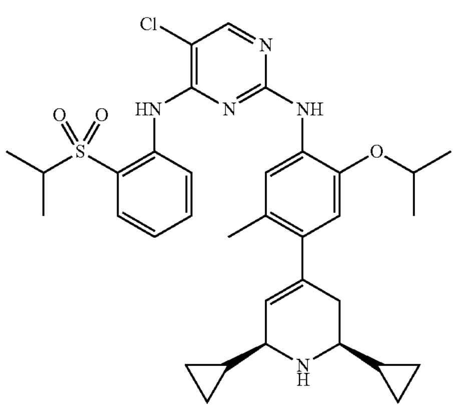 [SMILES: Cc1cc(Nc2ncc(Cl)c(Nc3ccccc3S(=O)(=O)C(C)C)n2)c(OC(C)C)cc1C1=C[C@H](C2CC2)N[C@H](C2CC2)C1] | 5-chloro-N2-(4-((2S,6S)-2,6-dicyclopropyl-1,2,3,6-tetrahydropyridin-4-yl)-2-isopropoxy-5-methylphenyl)-N4-(2-(isopropylsulfonyl)phenyl)pyrimidine-2,4-diamine |

TABLE 2-continued

| Cpd. No. | Structure | Name |
|---|---|---|
| 44 | 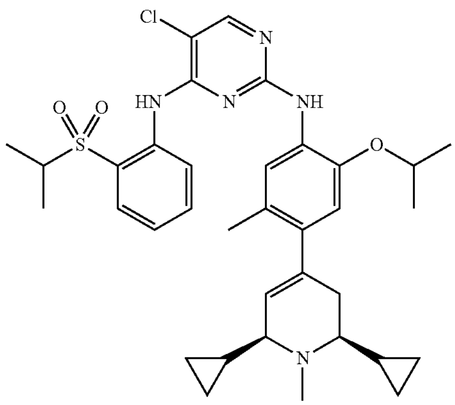 [SMILES: Cc1cc(Nc2ncc(Cl)c(Nc3ccccc3S(=O)(=O)C(C)C)n2)c(OC(C)C)cc1C1=C[C@H](C2CC2)N(C)[C@H](C2CC2)C1] | 5-chloro-N2-(4-((2S,6S)-2,6-dicyclopropyl-1-methyl-1,2,3,6-tetrahydropyridin-4-yl)-2-isopropoxy-5-methylphenyl)-N4-(2-(isopropylsulfonyl)phenyl)pyrimidine-2,4-diamine |
| 45 | 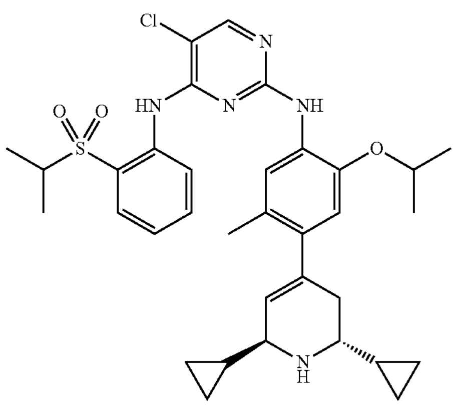 [SMILES: Cc1cc(Nc2ncc(Cl)c(Nc3ccccc3S(=O)(=O)C(C)C)n2)c(OC(C)C)cc1C1=C[C@H](C2CC2)N[C@@H](C2CC2)C1] | 5-chloro-N2-(4-((2R,6S)-2,6-dicyclopropyl-1,2,3,6-tetrahydropyridin-4-yl)-2-isopropoxy-5-methylphenyl)-N4-(2-(isopropylsulfonyl)phenyl)pyrimidine-2,4-diamine |
| 46 | 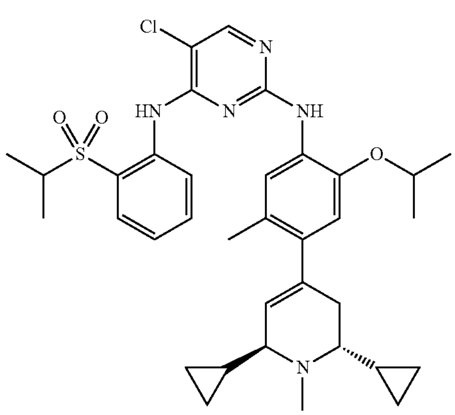 [SMILES: Cc1cc(Nc2ncc(Cl)c(Nc3ccccc3S(=O)(=O)C(C)C)n2)c(OC(C)C)cc1C1=C[C@H](C2CC2)N(C)[C@@H](C2CC2)C1] | 5-chloro-N2-(4-((2R,6S)-2,6-dicyclopropyl-1-methyl-1,2,3,6-tetrahydropyridin-4-yl)-2-isopropoxy-5-methylphenyl)-N4-(2-(isopropylsulfonyl)phenyl)pyrimidine-2,4-diamine |

TABLE 2-continued

| Cpd. No. | Structure | Name |
|---|---|---|
| 47 | 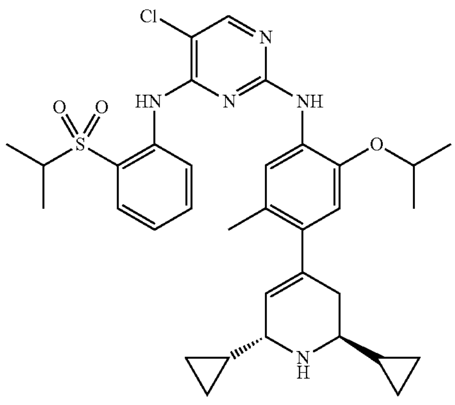 [SMILES: Cc1cc(Nc2ncc(Cl)c(Nc3ccccc3S(=O)(=O)C(C)C)n2)c(OC(C)C)cc1C1=C[C@@H](C2CC2)N[C@H](C2CC2)C1] | 5-chloro-N2-(4-((2S,6R)-2,6-dicyclopropyl-1,2,3,6-tetrahydropyridin-4-yl)-2-isopropoxy-5-methylphenyl)-N4-(2-(isopropylsulfonyl)phenyl)pyrimidine-2,4-diamine |
| 48 | 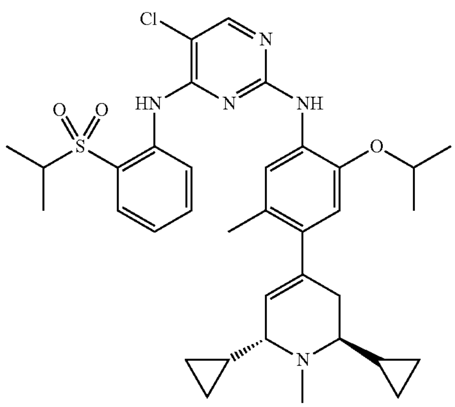 [SMILES: Cc1cc(Nc2ncc(Cl)c(Nc3ccccc3S(=O)(=O)C(C)C)n2)c(OC(C)C)cc1C1=C[C@@H](C2CC2)N(C)[C@H](C2CC2)C1] | 5-chloro-N2-(4-((2S,6R)-2,6-dicyclopropyl-1-methyl-1,2,3,6-tetrahydropyridin-4-yl)-2-isopropoxy-5-methylphenyl)-N4-(2-(isopropylsulfonyl)phenyl)pyrimidine-2,4-diamine |
| 49 | 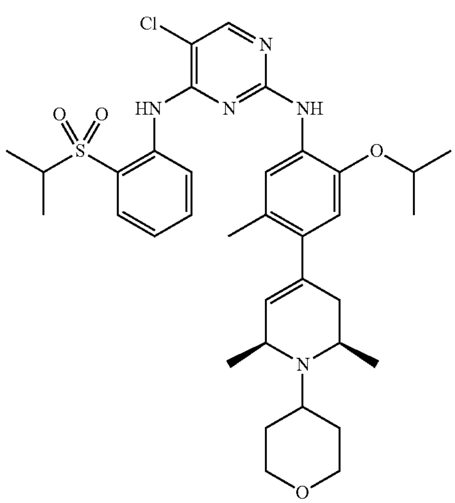 [SMILES: Cc1cc(Nc2ncc(Cl)c(Nc3ccccc3S(=O)(=O)C(C)C)n2)c(OC(C)C)cc1C1=C[C@H](C)N(C2CCOCC2)[C@H](C)C1] | 5-chloro-N2-(4-((2R,6S)-2,6-dimethyl-1-(tetrahydro-2H-pyran-4-yl)-1,2,3,6-tetrahydropyridin-4-yl)-2-isopropoxy-5-methylphenyl)-N4-(2-(isopropylsulfonyl)phenyl)pyrimidine-2,4-diamine |

TABLE 2-continued

| Cpd. No. | Structure | Name |
|---|---|---|
| 50 | 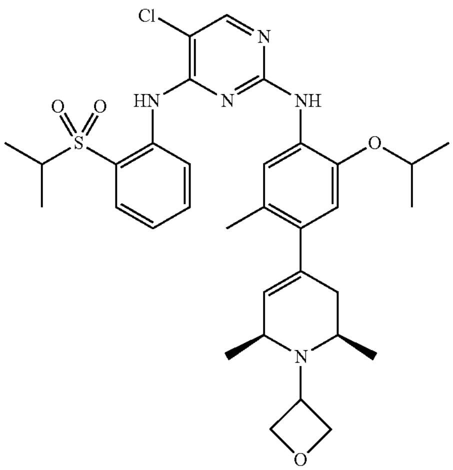 [SMILES: Cc1cc(Nc2ncc(Cl)c(Nc3ccccc3S(=O)(=O)C(C)C)n2)c(OC(C)C)cc1C1=C[C@H](C)N(C2COC2)[C@H](C)C1] | 5-chloro-N2-(4-((2R,6S)-2,6-dimethyl-1-(oxetan-3-yl)-1,2,3,6-tetrahydropyridin-4-yl)-2-isopropoxy-5-methylphenyl)-N4-(2-(isopropylsulfonyl)phenyl)pyrimidine-2,4-diamine |
| 51 | 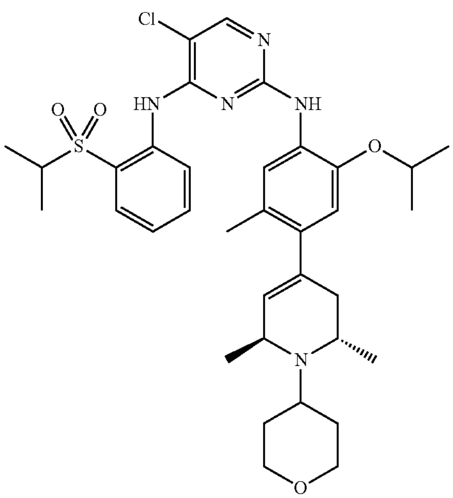 [SMILES: Cc1cc(Nc2ncc(Cl)c(Nc3ccccc3S(=O)(=O)C(C)C)n2)c(OC(C)C)cc1C1=C[C@H](C)N(C2CCOCC2)[C@@H](C)C1] | 5-chloro-N2-(4-((2S,6S)-2,6-dimethyl-1-(tetrahydro-2H-pyran-4-yl)-1,2,3,6-tetrahydropyridin-4-yl)-2-isopropoxy-5-methylphenyl)-N4-(2-(isopropylsulfonyl)phenyl)pyrimidine-2,4-diamine |
| 52 | 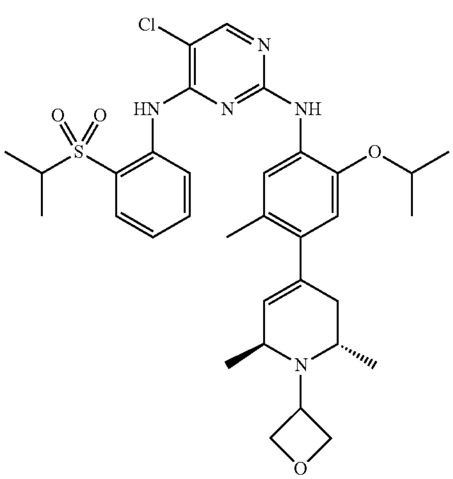 [SMILES: Cc1cc(Nc2ncc(Cl)c(Nc3ccccc3S(=O)(=O)C(C)C)n2)c(OC(C)C)cc1C1=C[C@H](C)N(C2COC2)[C@@H](C)C1] | 5-chloro-N2-(4-((2S,6S)-2,6-dimethyl-1-(oxetan-3-yl)-1,2,3,6-tetrahydropyridin-4-yl)-2-isopropoxy-5-methylphenyl)-N4-(2-(isopropylsulfonyl)phenyl)pyrimidine-2,4-diamine |

TABLE 2-continued

| Cpd. No. | Structure | Name |
|---|---|---|
| 53 | 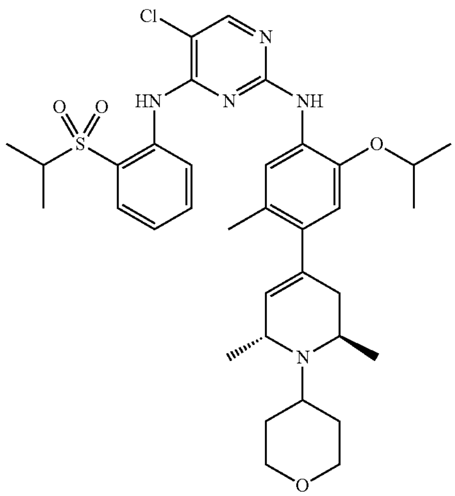 [SMILES: Cc1cc(Nc2ncc(Cl)c(Nc3ccccc3S(=O)(=O)C(C)C)n2)c(OC(C)C)cc1C1=C[C@@H](C)N(C2CCOCC2)[C@H](C)C1] | 5-chloro-N2-(4-((2R,6R)-2,6-dimethyl-1-(tetrahydro-2H-pyran-4-yl)-1,2,3,6-tetrahydropyridin-4-yl)-2-isopropoxy-5-methylphenyl)-N4-(2-(isopropylsulfonyl)phenyl)pyrimidine-2,4-diamine |
| 54 | 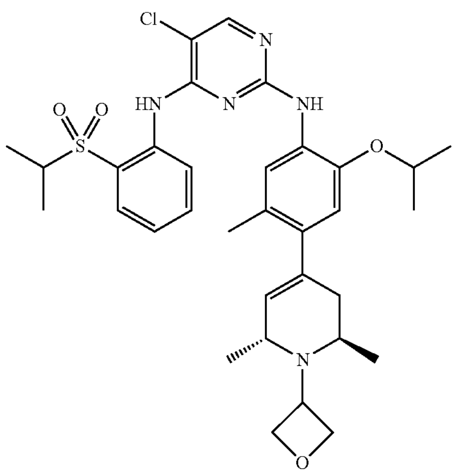 [SMILES: Cc1cc(Nc2ncc(Cl)c(Nc3ccccc3S(=O)(=O)C(C)C)n2)c(OC(C)C)cc1C1=C[C@@H](C)N(C2COC2)[C@H](C)C1] | 5-chloro-N2-(4-((2R,6R)-2,6-dimethyl-1-(oxetan-3-yl)-1,2,3,6-tetrahydropyridin-4-yl)-2-isopropoxy-5-methylphenyl)-N4-(2-(isopropylsulfonyl)phenyl)pyrimidine-2,4-diamine |
| 55 | 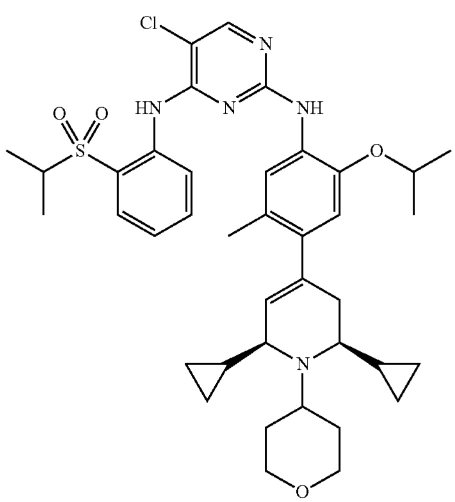 [SMILES: Cc1cc(Nc2ncc(Cl)c(Nc3ccccc3S(=O)(=O)C(C)C)n2)c(OC(C)C)cc1C1=C[C@H](C2CC2)N(C2CCOCC2)[C@H](C2CC2)C1] | 5-chloro-N2-(4-((2S,6S)-2,6-dicyclopropyl-1-(tetrahydro-2H-pyran-4-yl)-1,2,3,6-tetrahydropyridin-4-yl)-2-isopropoxy-5-methylphenyl)-N4-(2-(isopropylsulfonyl)phenyl)pyrimidine-2,4-diamine |

TABLE 2-continued

| Cpd. No. | Structure | Name |
|---|---|---|
| 56 | 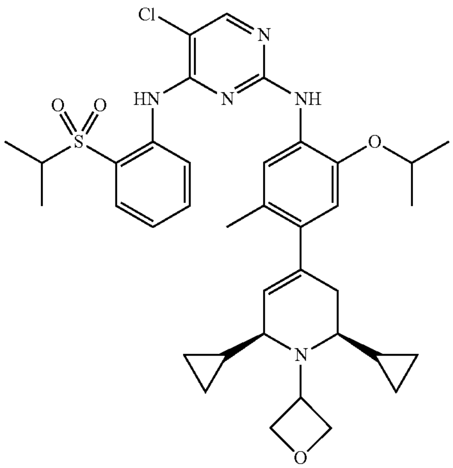 [SMILES: Cc1cc(Nc2ncc(Cl)c(Nc3ccccc3S(=O)(=O)C(C)C)n2)c(OC(C)C)cc1C1=C[C@H](C2CC2)N(C2COC2)[C@H](C2CC2)C1] | 5-chloro-N2-(4-((2S,6S)-2,6-dicyclopropyl-1-(oxetan-3-yl)-1,2,3,6-tetrahydropyridin-4-yl)-2-isopropoxy-5-methylphenyl)-N4-(2-(isopropylsulfonyl)phenyl)pyrimidine-2,4-diamine |
| 57 | 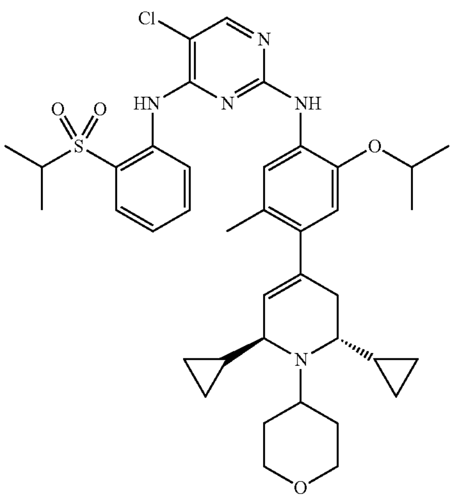 [SMILES: Cc1cc(Nc2ncc(Cl)c(Nc3ccccc3S(=O)(=O)C(C)C)n2)c(OC(C)C)cc1C1=C[C@H](C2CC2)N(C2CCOCC2)[C@@H](C2CC2)C1] | 5-chloro-N2-(4-((2R,6S)-2,6-dicyclopropyl-1-(tetrahydro-2H-pyran-4-yl)-1,2,3,6-tetrahydropyridin-4-yl)-2-isopropoxy-5-methylphenyl)-N4-(2-(isopropylsulfonyl)phenyl)pyrimidine-2,4-diamine |
| 58 | 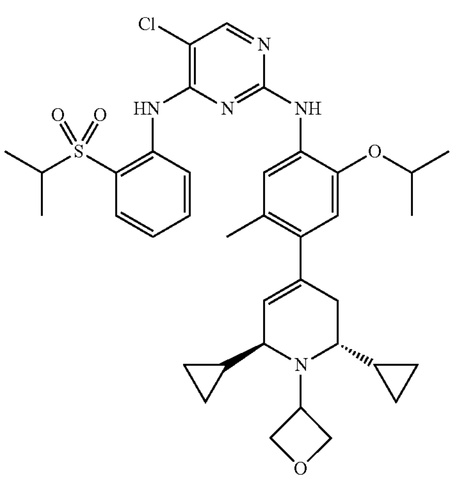 [SMILES: Cc1cc(Nc2ncc(Cl)c(Nc3ccccc3S(=O)(=O)C(C)C)n2)c(OC(C)C)cc1C1=C[C@H](C2CC2)N(C2COC2)[C@@H](C2CC2)C1] | 5-chloro-N2-(4-((2R,6S)-2,6-dicyclopropyl-1-(oxetan-3-yl)-1,2,3,6-tetrahydropyridin-4-yl)-2-isopropoxy-5-methylphenyl)-N4-(2-(isopropylsulfonyl)phenyl)pyrimidine-2,4-diamine |

TABLE 2-continued

| Cpd. No. | Structure | Name |
|---|---|---|
| 59 | 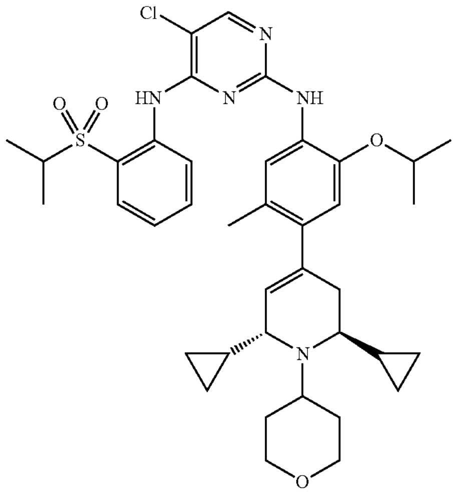 [SMILES: Cc1cc(Nc2ncc(Cl)c(Nc3ccccc3S(=O)(=O)C(C)C)n2)c(OC(C)C)cc1C1=C[C@@H](C2CC2)N(C2CCOCC2)[C@H](C2CC2)C1] | 5-chloro-N2-(4-((2S,6R)-2,6-dicyclopropyl-1-(tetrahydro-2H-pyran-4-yl)-1,2,3,6-tetrahydropyridin-4-yl)-2-isopropoxy-5-methylphenyl)-N4-(2-(isopropylsulfonyl)phenyl)pyrimidine-2,4-diamine |
| 60 | 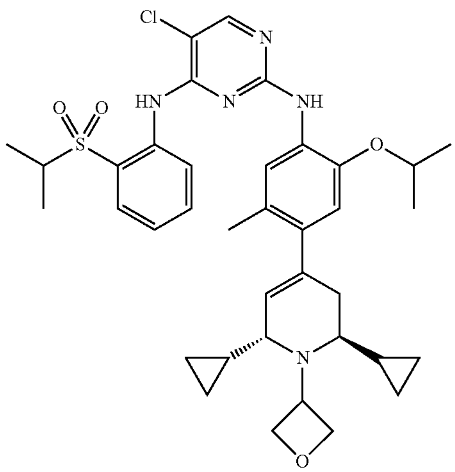 [SMILES: Cc1cc(Nc2ncc(Cl)c(Nc3ccccc3S(=O)(=O)C(C)C)n2)c(OC(C)C)cc1C1=C[C@@H](C2CC2)N(C2COC2)[C@H](C2CC2)C1] | 5-chloro-N2-(4-((2S,6R)-2,6-dicyclopropyl-1-(oxetan-3-yl)-1,2,3,6-tetrahydropyridin-4-yl)-2-isopropoxy-5-methylphenyl)-N4-(2-(isopropylsulfonyl)phenyl)pyrimidine-2,4-diamine |

In another embodiment, a Compound of the Disclosure is 5-chloro-$N^2$-(2-isopropoxy-5-methyl-4-(1-(tetrahydro-2H-pyran-4-yl)-1,2,3,6-tetrahydropyridin-4-yl) phenyl)-$N^4$-(2-(isopropylsulfonyl)phenyl)pyrimidine-2,4-diamine, or a pharmaceutically acceptable salt or hydrate thereof.

Compounds of the Disclosure inhibit ALK and are useful in the treatment or prevention of a variety of diseases and conditions. In particular, Compounds of the Disclosure are useful in methods of treating or preventing a disease or condition wherein inhibition of ALK provides a benefit, for example, cancers and proliferative diseases. The therapeutic methods of this disclosure comprise administering a therapeutically effective amount of a Compound of the Disclosure to an individual in need thereof. The present methods also encompass administering a second therapeutic agent to the individual in addition to the Compound of the Disclosure. The second therapeutic agent is selected from drugs known as useful in treating the disease or condition afflicting the individual in need thereof, e.g., a chemotherapeutic agent and/or radiation known as useful in treating a particular cancer.

Certain of the Compounds of the Disclosure may exist as stereoisomers, i.e., isomers that differ only in the spatial arrangement of atoms, including optical isomers and conformational isomers (or conformers) and tautomers. The disclosure includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" or "racemate" refers to a mixture of equal parts of enantiomers and which mixture is optically inactive.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry. Certain compounds of the Disclosure can have an ee of about 70% or more, e.g., about 80% or more, about 90% or more, about 91% or more, about 92% or more, about 93% or more, about 94% or more, about 95% or more, about 96% or more, about 97% or more, about 98% or more, or about 99% or more, The terms "enantiomerically pure" or "enantiopure" refer to a sample of a chiral substance all of whose molecules (within the limits of detection) have the same chirality sense.

The terms "enantiomerically enriched" or "enantioenriched" refer to a sample of a chiral substance whose enantiomeric ratio is greater than 50:50. In Enantiomerically enriched compounds may be enantiomerically pure.

Salts, hydrates, and solvates of the Compounds of the Disclosure can also be used in the methods disclosed herein. The present disclosure encompasses the preparation and use of salts of Compounds of the Disclosure. As used herein, the pharmaceutical "pharmaceutically acceptable salt" refers to salts or zwitterionic forms of Compounds of the Disclosure. Salts of Compounds of the Disclosure can be prepared during the final isolation and purification of the compounds or separately by reacting the compound with an acid having a suitable cation. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, and ethanol, and it is intended that the disclosure includes both solvated and unsolvated forms of Compounds of the Disclosure.

One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by van Tonder et al., *AAPS Pharm. Sci. Tech.*, 5(1):Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present disclosure provides Compounds of the Disclosure as inhibitors of ALK for the treatment of a variety of diseases and conditions wherein inhibition has a beneficial effect. Compounds of the Disclosure typically have a binding affinity ($IC_{50}$) to ALK of less than 100 μM, e.g., less than about 50 μM, less than about 25 μM, and less than about 5 μM, less than about 1 μM, less than about 0.5 μM, less than about 0.1 μM, less than about 0.05 μM, less than about 0.01 μM, less than about 0.005 μM, or less than about 0.001 μM. In one embodiment, the present disclosure relates to a method of treating an individual suffering from a disease or condition wherein inhibition of ALK provides a benefit comprising administering a therapeutically effective amount of a Compound of the Disclosure to an individual in need thereof.

Since Compounds of the Disclosure are ALK inhibitors, a number of diseases and conditions mediated by ALK can be treated by employing these compounds. The present disclosure is thus directed generally to a method for treating a condition or disorder responsive to inhibition of ALK, or an isoform or mutant thereof, in an animal, e.g., a human patient, suffering from, or at risk of suffering from, the condition or disorder, the method comprising administering to the animal an effective amount of one or more Compounds of the Disclosure.

The present disclosure is further directed to a method of inhibiting ALK, or an isoform or mutant thereof, in an animal in need thereof, said method comprising administering to the animal an effective amount of at least one Compound of the Disclosure.

The methods of the present disclosure can be accomplished by administering a Compound of the Disclosure as the neat compound or as a pharmaceutical composition. Administration of a pharmaceutical composition, or neat compound of a Compound of the Disclosure, can be performed during or after the onset of the disease or condition of interest. Typically, the pharmaceutical compositions are sterile, and contain no toxic, carcinogenic, or mutagenic compounds that would cause an adverse reaction when administered.

Further provided are kits comprising a Compound of the Disclosure and, optionally, a second therapeutic agent useful in the treatment of diseases and conditions wherein inhibition of ALK, or an isoform or mutant thereof, provides a benefit, packaged separately or together, and an insert having instructions for using these active agents.

In one embodiment, a Compound of the Disclosure is administered in conjunction with a second therapeutic agent useful in the treatment of a disease or condition wherein inhibition of ALK proteins provides a benefit. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered. The Compound of the Disclosure therefore can be used in conjunction with one or more second therapeutic agents, for example, but not limited to, anticancer agents.

Diseases and conditions treatable by the methods of the present disclosure include, but are not limited to, cancer and other proliferative disorders, inflammatory diseases, sepsis, autoimmune disease, and viral infection. In one embodiment, Diseases and conditions treatable by the methods of the present disclosure are cancer, a chronic autoimmune disorder, an inflammatory condition, or a proliferative disorder. In one embodiment, a human patient is treated with a Compound of the Disclosure, or a pharmaceutical composition comprising a Compound of the Disclosure, wherein the compound is administered in an amount sufficient to inhibit ALK in the patient.

In one embodiment, the disease to be treated or prevented by the Compound of the Disclosure is cancer. In another embodiment, the present disclosure provides a method of treating or preventing cancer in a subject in need thereof comprising administering a therapeutically effective amount of a Compound of the Disclosure to the subject. While not being limited to a specific mechanism, in some embodiments, Compounds of the Disclosure can treat or prevent cancer by inhibiting ALK. Examples of treatable cancers include, but are not limited to, any one or more of the cancers of Table 3.

TABLE 3 adrenal cancer
acinic cell carcinoma
acoustic neuroma
acral lentigious melanoma
acrospiroma
acute eosinophilic leukemia
acute erythroid leukemia
acute lymphoblastic leukemia
acute megakaryoblastic leukemia
acute monocytic leukemia
acute promyelocytic leukemia
adenocarcinoma
adenoid cystic carcinoma
adenoma
adenomatoid odontogenic tumor
adenosquamous carcinoma
adipose tissue neoplasm
adrenocortical carcinoma
adult T-cell leukemia/lymphoma
aggressive NK-cell leukemia
AIDS-related lymphoma
alveolar rhabdomyosarcoma
alveolar soft part sarcoma
ameloblastic fibroma
anaplastic large cell lymphoma
anaplastic thyroid cancer
angioimmunoblastic T-cell lymphoma,
angiomyolipoma
angiosarcoma
astrocytoma
atypical teratoid rhabdoid tumor
B-cell chronic lymphocytic leukemia
B-cell prolymphocytic leukemia
B-cell lymphoma
basal cell carcinoma
biliary tract cancer
bladder cancer
blastoma
bone cancer
Brenner tumor
Brown tumor
Burkitt's lymphoma
breast cancer
brain cancer
carcinoma
carcinoma in situ
carcinosarcoma
cartilage tumor
cementoma
myeloid sarcoma
chondroma
chordoma
choriocarcinoma
choroid plexus papilloma
clear-cell sarcoma of the kidney
craniopharyngioma
cutaneous T-cell lymphoma
cervical cancer
colorectal cancer
Degos disease
desmoplastic small round cell tumor TABLE 3-continued diffuse large B-cell lymphoma
dysembryoplastic neuroepithelial tumor,
dysgerminoma
embryonal carcinoma
endocrine gland neoplasm
endodermal sinus tumor
enteropathy-associated T-cell lymphoma
esophageal cancer
fetus in fetu
fibroma
fibrosarcoma
follicular lymphoma
follicular thyroid cancer
ganglioneuroma
gastrointestinal cancer
germ cell tumor
gestational choriocarcinoma
giant cell fibroblastoma
giant cell tumor of the bone
glial tumor
glioblastoma multiforme
glioma
gliomatosis cerebri
glucagonoma
gonadoblastoma
granulosa cell tumor
gynandroblastoma
gallbladder cancer
gastric cancer
hairy cell leukemia
hemangioblastoma
head and neck cancer
hemangiopericytoma
hematological malignancy
hepatoblastoma
hepatosplenic T-cell lymphoma
Hodgkin's lymphoma
non-Hodgkin's lymphoma
invasive lobular carcinoma
intestinal cancer
kidney cancer
laryngeal cancer
lentigo maligna
lethal midline carcinoma
leukemia
leydig cell tumor
liposarcoma
lung cancer
lymphangioma
lymphangiosarcoma
lymphoepithelioma
lymphoma
acute lymphocytic leukemia
acute myelogeous leukemia
chronic lymphocytic leukemia
liver cancer
small cell lung cancer
non-small cell lung cancer
MALT lymphoma
malignant fibrous histiocytoma
malignant peripheral nerve sheath tumor
malignant triton tumor
mantle cell lymphoma
marginal zone B-cell lymphoma
mast cell leukemia
mediastinal germ cell tumor
medullary carcinoma of the breast
medullary thyroid cancer,
medulloblastoma
melanoma,
meningioma,
merkel cell cancer
mesothelioma
metastatic urothelial carcinoma
mixed Mullerian tumor
mucinous tumor
multiple myeloma
muscle tissue neoplasm
mycosis fungoides
myxoid liposarcoma
myxoma
myxosarcoma
nasopharyngeal carcinoma
neurinoma
neuroblastoma
neurofibroma
neuroma
nodular melanoma
ocular cancer
oligoastrocytoma
oligodendroglioma
oncocytoma
optic nerve sheath meningioma
optic nerve tumor
oral cancer
osteosarcoma
ovarian cancer
Pancoast tumor
papillary thyroid cancer
paraganglioma
pinealoblastoma
pineocytoma
pituicytoma
pituitary adenoma
pituitary tumor
plasmacytoma
polyembryoma
precursor T-lymphoblastic lymphoma
primary central nervous system lymphoma
primary effusion lymphoma
preimary peritoneal cancer
prostate cancer
pancreatic cancer
pharyngeal cancer
pseudomyxoma periotonei
renal cell carcinoma
renal medullary carcinoma
retinoblastoma
rhabdomyoma
rhabdomyosarcoma
Richter's transformation
rectal cancer
sarcoma
Schwannomatosis
seminoma
Sertoli cell tumor
sex cord-gonadal stromal tumor
signet ring cell carcinoma
skin cancer
small blue round cell tumors
small cell carcinoma
soft tissue sarcoma
somatostatinoma
soot wart
spinal tumor
splenic marginal zone lymphoma
squamous cell carcinoma
synovial sarcoma
Sezary's disease
small intestine cancer
squamous carcinoma
stomach cancer
T-cell lymphoma
testicular cancer
thecoma
thyroid cancer
transitional cell carcinoma
throat cancer
urachal cancer
urogenital cancer
urothelial carcinoma
uveal melanoma
uterine cancer
verrucous carcinoma
visual pathway glioma
vulvar cancer
vaginal cancer TABLE 3-continued Waldenstrom's macroglobulinemia
Warthin's tumor
Wilms' tumor In another embodiment, the cancer is a leukemia, for example a leukemia selected from acute monocytic leukemia, acute myelogenous leukemia, chronic myelogenous leukemia, chronic lymphocytic leukemia and mixed lineage leukemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In another embodiment, the cancer is anaplastic large-cell lymphoma, non-small cell lung cancer, diffuse large B-cell lymphoma, inflammatory myofibroblastic tumors, neuroblastoma, anaplastic thyroid cancer, and rhabdomyosarcoma.

In another embodiment, the cancer is breast cancer, colorectal cancer, esophageal squamous cell cancer, and renal cell carcinoma.

In another embodiment, the present disclosure provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

Compounds of the Disclosure can also treat infectious and noninfectious inflammatory events and autoimmune and other inflammatory diseases by administration of an effective amount of a present compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendictitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In another embodiment, the present disclosure provides a method of treating systemic inflammatory response syndromes, such as LPS-induced endotoxic shock and/or bacteria-induced sepsis by administration of an effective amount of a Compound of the Disclosure to a mammal, in particular a human in need of such treatment.

In another embodiment, the present disclosure provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatis B virus, and hepatitis C virus.

In another embodiment, the present disclosure provides therapeutic method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of a Compound of the Disclosure to a subject in need of such therapy.

In another embodiment, the present disclosure provides a method of regulating endogenous or heterologous promoter activity by contacting a cell with a Compound of the Disclosure.

In methods of the present disclosure, a therapeutically effective amount of a Compound of the Disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the patient, and ultimately is determined by the attendant physician. Dosage amounts and intervals can be adjusted individually to provide plasma levels of the ALK inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A Compound of the Disclosure used in a method of the present disclosure can be administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a Compound of the Disclosure, or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

As stated above, a Compound of the Disclosure can be administered in combination with a second therapeutically active agent. In some embodiments, the second therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, chemotherapeutic agents or other anti-proliferative agents can be combined with Compound of the Disclosure to treat proliferative diseases and cancer. Examples of therapies and anticancer agents that can be used in combination with Compounds of the Disclosure include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Examples of antiproliferative compounds include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include, but are not limited to, steroids, such as atamestane, exemestane, and formestane, and non-steroids, such as aminoglutethimide, roglethimide, pyridoglutethimide, trilostane, testolactone, ketoconazole, vorozole, fadrozole, anastrozole, and letrozole.

Nonlimiting anti-estrogens include, but are not limited to, tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Exemplary topoisomerase I inhibitors include, but are not limited to, topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; vinca alkaloids, such as vinblastine, vinblastine sulfate, vincristine, and vincristine sulfate, and vinorelbine; discodermolides; cochicine and epothilones and derivatives thereof.

Exemplary nonlimiting alkylating agents include cyclophosphamide, ifosfamide, melphalan, and nitrosoureas, such as carmustine and lomustine.

Exemplary nonlimiting cyclooxygenase inhibitors include Cox-2 inhibitors, 5-alkyl substituted 2-arylaminophenylacetic acid and derivatives, such as celecoxib, rofecoxib, etoricoxib, valdecoxib, or a 5-alkyl-2-arylaminophenylacetic acid, such as lumiracoxib.

Exemplary nonlimiting matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary nonlimiting mTOR inhibitors include compounds that inhibit the mammalian target of rapamycin (mTOR) and possess antiproliferative activity such as sirolimus, everolimus, CCI-779, and ABT578.

Exemplary nonlimiting antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Exemplary nonlimiting platin compounds include carboplatin, cis-platin, cisplatinum, and oxaliplatin.

Exemplary nonlimiting methionine aminopeptidase inhibitors include bengamide or a derivative thereof and PPI-2458.

Exemplary nonlimiting bisphosphonates include etridonic acid, clodronic acid, tiludronic acid, pamidronic acid, alendronic acid, ibandronic acid, risedronic acid, and zoledronic acid.

Exemplary nonlimiting antiproliferative antibodies include trastuzumab, trastuzumab-DM1, cetuximab, bevacizumab, rituximab, PR064553, and 2C4. The term "antibody" includes intact monoclonal antibodies, polyclonal antibodies, multispecific antibodies formed from at least two intact antibodies, and antibody fragments, so long as they exhibit the desired biological activity.

Exemplary nonlimiting heparanase inhibitors include compounds that target, decrease, or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras, for example, a farnesyl transferase inhibitor, such as L-744832, DK8G557, tipifarnib, and lonafarnib.

Exemplary nonlimiting telomerase inhibitors include compounds that target, decrease, or inhibit the activity of telomerase, such as compounds that inhibit the telomerase receptor, such as telomestatin.

Exemplary nonlimiting proteasome inhibitors include compounds that target, decrease, or inhibit the activity of the proteasome including, but not limited to, bortezomid.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, I-β-D-arabinofuransylcytosine (ara-c), and bisulfan; and ALK inhibitors, which are compounds which target, decrease, or inhibit anaplastic lymphoma kinase.

Exemplary nonlimiting Flt-3 inhibitors include PKC412, midostaurin, a staurosporine derivative, SU11248, and MLN518.

Exemplary nonlimiting HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino,17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidine-amine derivatives, such as imatinib, SU101, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Axl receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl) methyl]amino}-benzoic acid adamantyl ester; NSC 680410, adaphostin); l) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, C1-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a present ALK inhibitor include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

Other examples of second therapeutic agents, one or more of which a present ALK inhibitor also can be combined, include, but are not limited to: a treatment for Alzheimer's Disease, such as donepezil and rivastigmine; a treatment for Parkinson's Disease, such as L-DOPA/carbidopa, entacapone, ropinrole, pramipexole, bromocriptine, pergolide, trihexephendyl, and amantadine; an agent for treating multiple sclerosis (MS) such as beta interferon (e.g., AVONEX® and REBIF®), glatiramer acetate, and mitoxantrone; a treatment for asthma, such as albuterol and montelukast; an agent for treating schizophrenia, such as zyprexa, risperdal, seroquel, and haloperidol; an anti-inflammatory agent, such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor, such as an acetylcholinesterase inhibitor, an MAO inhibitor, an interferon, an anti-convulsant, an ion channel blocker, riluzole, or an anti-Parkinson's agent; an agent for treating cardiovascular disease, such as a beta-blocker, an ACE inhibitor, a diuretic, a nitrate, a calcium channel blocker, or a statin; an agent for treating liver disease, such as a corticosteroid, cholestyramine, an interferon, and an anti-viral agent; an agent for treating blood disorders, such as a corticosteroid, an anti-leukemic agent, or a growth factor; or an agent for treating immunodeficiency disorders, such as gamma globulin.

The above-mentioned second therapeutically active agents, one or more of which can be used in combination with a Compound of the Disclosure, are prepared and administered as described in the art.

Compounds of the Disclosure typically are administered in admixture with a pharmaceutical carrier selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compound of the Disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of the Disclosure can be readily combined with pharmaceutically acceptable carriers well-known in the art. In one embodiment, a pharmaceutical composition comprising a Compound of the Disclosure, or a pharmaceutically acceptable salt or hydrate thereof, and a pharmaceutically acceptable carrier, is provided. Standard pharmaceutical carriers are described in Remington's Pharmaceutical Sciences, Mack Publishing Co., Easton, Pa., 19th ed. 1995. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in watersoluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration.

The term "a disease or condition wherein inhibition of ALK provides a benefit" pertains to a disease or condition in which ALK, is important or necessary, e.g., for the onset, progress, expression of that disease or condition, or a disease or a condition which is known to be treated by an ALK inhibitor. Examples of such conditions include, but are not limited to, a cancer, a chronic autoimmune disease, an inflammatory disease, a proliferative disease, sepsis, and a viral infection. One of ordinary skill in the art is readily able to determine whether a compound treats a disease or condition mediated by an ALK inhibitor for any particular cell type, for example, by assays which conveniently can be used to assess the activity of particular compounds. The term "anaplastic lymphoma kinase" or "ALK" includes isoforms and mutants of ALK.

The term "second therapeutic agent" refers to a therapeutic agent different from a Compound of the Disclosure and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, Compounds of the Disclosure are inhibitors of ALK and can be used in treating or preventing diseases and conditions wherein inhibition of ALK provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. The term "treat" and synonyms contemplate administering a therapeutically effective amount of a Compound of the Disclosure to a subject in need of such treatment. The treatment can be orientated symptomatically, for example, to suppress symptoms. It can be effected over a short period, be oriented over a medium term, or can be a long-term treatment, for example within the context of a maintenance therapy.

As used herein, the terms "prevent," "preventing," and "prevention" refer to a method of preventing the onset of a disease or condition and/or its attendant symptoms or barring a subject from acquiring a disease. As used herein, "prevent," "preventing," and "prevention" also include delaying the onset of a disease and/or its attendant symptoms and reducing a subject's risk of acquiring a disease. The terms "prevent," "preventing" and "prevention" may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a Compound of the Disclosure can be administered at the same time or sequentially in any order at different points in time as a second therapeutic agent. A Compound of the Disclosure and the second therapeutic agent can be administered separately, in any appropriate form and by any suitable route. When a Compound of the Disclosure and the second therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a Compound of the Disclosure and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart.

The use of the terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

In the present disclosure, the term "alkyl" as used by itself or as part of another group refers to unsubstituted straight- or branched-chain aliphatic hydrocarbons containing from one to twelve carbon atoms, i.e., $C_{1-12}$ alkyl, or the number of carbon atoms designated, e.g., a $C_1$ alkyl such as methyl, a $C_2$ alkyl such as ethyl, a $C_3$ alkyl such as propyl or isopropyl, a $C_{1-3}$ alkyl such as methyl, ethyl, propyl, or isopropyl, and so on. In one embodiment, the alkyl is a $C_{1-4}$ alkyl. Non-limiting exemplary $C_{1-12}$ alkyl groups include methyl, ethyl, propyl, isopropyl, butyl, sec-butyl, tert-butyl, iso-butyl, 3-pentyl, hexyl, heptyl, octyl, nonyl, and decyl. Exemplary $C_{1-4}$ alkyl groups are methyl, ethyl, propyl, isopropyl, butyl, sec-butyl, tert-butyl, and iso-butyl.

In the present disclosure, the term "cycloalkyl" as used by itself or as part of another group refers to saturated and partially unsaturated (containing one or two double bonds) cyclic aliphatic hydrocarbons containing one or two rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, cyclopentenyl, and cyclohexenyl.

In the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members (i.e., a 3- to 14-membered heterocyclo) wherein at least one carbon atom of one of the rings is replaced with a heteroatom. Each heteroatom is independently selected from the group consisting of oxygen, sulfur, including sulfoxide and sulfone, and/or nitrogen atoms, which can be oxidized or quaternized. The term "heterocyclo" is meant to include groups wherein a ring —CH$_2$— is replaced with a —C(=O)—, for example, cyclic ureido groups such as 2-imidazolidinone and cyclic amide groups such as β-lactam, γ-lactam, δ-lactam, ε-lactam, and piperazin-2-one. In one embodiment, the heterocyclo group is a 3- to 8-membered cyclic group containing one ring and one or two oxygen and/or nitrogen atoms. In one embodiment, the heterocyclo group is a 4-, 5- or 6-membered cyclic group containing one ring and one or two oxygen and/or nitrogen atoms. In one embodiment, the heterocyclo group is a 4- or 6-membered cyclic group containing one ring and one oxygen or nitrogen atom. The heterocyclo can be optionally linked to the rest of the molecule through any available carbon or nitrogen atom. Non-limiting exemplary heterocyclo groups include dioxanyl, tetrahydropyranyl, 2-oxopyrrolidin-3-yl, piperazin-2-one, piperazine-2,6-dione, 2-imidazolidinone, piperidinyl, morpholinyl, piperazinyl, pyrrolidinyl, and indolinyl.

EXAMPLES

Example 1

Synthesis of 5-chloro-N²-(2-isopropoxy-5-methyl-4-(2,2,6,6-tetramethyl-1,2,3,6-tetrahydropyridin-4-yl)phenyl)-N⁴-(2-(isopropylsulfonyl)phenyl)pyrimidine-2,4-diamine (Cpd. No. 2)

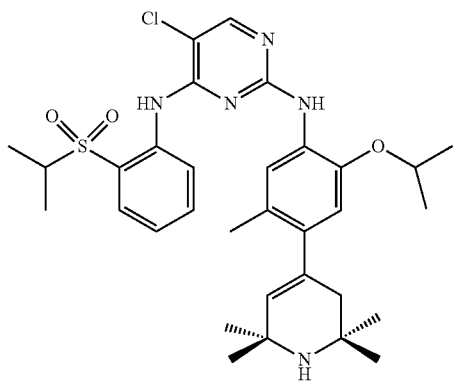

Step A: Synthesis of 4-(5-fluoro-2-methyl-4-nitrophenyl)-2,2,6,6-tetramethyl-1,2,3,6-tetrahydropyridine

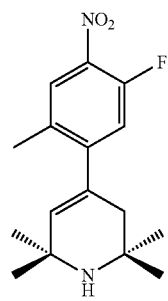

2,2,6,6-Tetramethyl-4-(4,4,5,5-tetramethyl-1,3,2-dioxaborolan-2-yl)-1,2,3,6-tetrahydropyridine (1.0 g, 3.77 mmol), Pd(dppf)Cl₂ (110 mg, 0.15 mmol), and K₂CO₃ (1.56 g, 11.31 mmol) were added to a solution of 1-bromo-5-fluoro-2-methyl-4-nitrobenzene (883 mg, 3.77 mmol) in DME-H₂O (22 mL, 10:1 mixture). The mixture was stirred at 80° C. for 12 hr under nitrogen. The reaction was cooled to room temperature and the product was extracted with ethyl acetate. The solvent was removed under reduced pressure and the residue was purified by silica gel chromatography with ethyl acetate/methanol (9/1, v/v) to afford the title compound (0.99 g, 90% yield). $^1$H NMR (400 MHz, CDCl₃) δ ppm 7.88 (d, J=7.6 Hz, 1H), 6.97 (d, J=11.6 Hz, 1H), 5.63 (s, 1H), 2.34 (s, 3H), 2.09-2.02 (m, 3H), 1.28 (s, 6H), 1.26 (s, 6H).

Step B: Synthesis of 4-(5-isopropoxy-2-methyl-4-nitrophenyl)-2,2,6,6-tetramethyl-1,2,3,6-tetrahydropyridine To a solution of tert-Butyl 4-(5-nitro-2-vinylphenyl)-5,6-dihydropyridine-1(2H)-carboxylate (0.99 g, 3.4 mmol) in 20 mL of 2-propanol was added Cs₂CO₃ (3.32 g, 10.2 mmol). The mixture was stirred at 60° C. overnight, and after cooling to room temperature, most of the 2-propanol was evaporated under reduced pressure. Water was added, and the solution was extracted with ethyl acetate. The organic layers were combined, dried over anhydrous Na₂SO₄, concentrated, and the crude product was purified by silica gel chromatography with ethyl acetate/methanol (9/1, v/v) to afford the title compound (0.9 g, 79%) as a pale yellow oil. $^1$H NMR (400 MHz, CDCl₃) δ 7.62 (s, 1H), 6.72 (s, 1H), 5.57 (t, J=1.7 Hz, 1H), 4.63-4.60 (m, 1H), 2.26 (s, 3H), 2.10-2.20 (m, 3H), 1.38 (d, J=6.0 Hz, 6H), 1.28 (s, 6H), 1.25 (s, 6H).

Step C: Synthesis of 2-isopropoxy-5-methyl-4-(2,2,6,6-tetramethyl-1,2,3,6-tetrahydropyridin-4-yl)aniline To a solution of 4-(5-isopropoxy-2-methyl-4-nitrophenyl)-2,2,6,6-tetramethyl-1,2,3,6-tetrahydropyridine (320 mg, 0.96 mmol) in 20 mL of ethanol was added several drops of 10% HCl, followed by iron powder (322 mg, 5.76 mmol). The mixture was stirred at 60° C. for 3 hr. The reaction was cooled to room temperature and the iron powder was filtered off. Ethanol was removed under reduced pressure and the title compound was obtained as colorless oil (250 mg, 86% yield). $^1$H NMR (400 MHz, CDCl₃) δ 6.54 (s, 1H), 6.51 (s, 1H), 5.47 (s, 1H), 4.49-4.45 (m, 1H), 3.68 (s, 2H), 2.17 (s, 3H), 2.05 (s, 2H), 1.34 (d, J=6.0 Hz, 6H), 1.25 (s, 6H), 1.23 (s, 6H).

Step D: Synthesis of 5-chloro-$N^2$-(2-isopropoxy-5-methyl-4-(2,2,6,6-tetramethyl-1,2,3,6-tetrahydropyridin-4-yl)phenyl)-$N^4$-(2-(isopropylsulfonyl)phenyl)pyrimidine-2,4-diamine

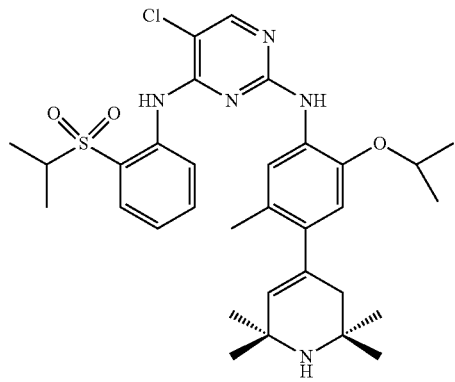

2-Isopropoxy-5-methyl-4-(2,2,6,6-tetramethyl-1,2,3,6-tetrahydropyridin-4-yl) aniline (250 mg, 0.828 mmol), 2,5-dichloro-N-(2-(isopropylsulfonyl)phenyl) pyrimidin-4-amine (286 mg, 0.828 mmol), Xantphos (48 mg, 0.083 mmol), Pd(OAc)$_2$ (9.3 mg, 0.042 mmol), and Cs$_2$CO$_3$ (810 mg, 2.48 mmol) were dissolved in anhydrous THF (10 mL). N$_2$ was bubbled through the reaction mixture for 5 min, and then the reaction vessel was sealed and heated under microwave irradiation to 150° C. for 30 min. The mixture was filtered and the filtrate concentrated under reduced pressure. After concentration, the crude product was purified by prep-HPLC (gradient from 10% to 60% acetonitrile in water) to give the title compound (130 mg, 26% yield). $^1$H NMR (400 MHz, CD$_3$OD) δ 8.37 (dd, J=8.3, 1.1 Hz, 1H), 8.24 (s, 1H), 7.99 (dd, J=8.0, 1.6 Hz, 1H), 7.80-7.62 (m, 2H), 7.52-7.38 (m, 1H), 6.76 (s, 1H), 5.62 (t, J=1.7 Hz, 1H), 4.70-4.58 (m, 1H), 3.44-3.33 (m, 1H), 2.50 (d, J=1.7 Hz, 2H), 2.14 (s, 3H), 1.63 (s, 6H), 1.59 (s, 6H), 1.34 (d, J=6.0 Hz, 6H), 1.27 (d, J=6.8 Hz, 6H).

Example 2

Synthesis of 5-chloro-$N^2$-(2-isopropoxy-5-methyl-4-(1,2,2,6,6-pentamethyl-1,2,3,6-tetrahydropyridin-4-yl)phenyl)-$N^4$-(2-(isopropylsulfonyl)phenyl)pyrimidine-2,4-diamine (Cpd. No. 1)

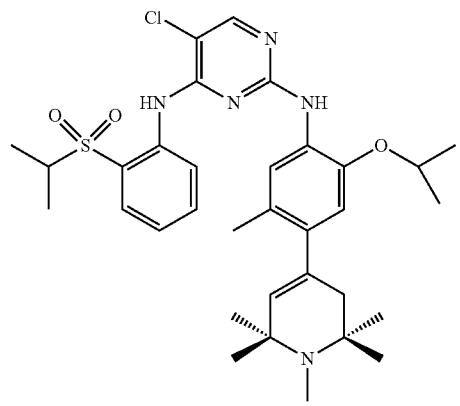

Step A: Synthesis of 4-(5-isopropoxy-2-methyl-4-nitrophenyl)-1,2,2,6,6-pentamethyl-1,2,3,6-tetrahydropyridine 37% Formaldehyde (365 mg, 4.5 mmol), acetic acid (135 mg, 2.25 mmol), and sodium triacetoxyborohydride (477 mg, 2.25 mmol) were added to a solution of 4-(5-isopropoxy-2-methyl-4-nitrophenyl)-2,2,6,6-tetramethyl-1,2,3,6-tetrahydropyridine (500 mg, 1.5 mmol) in DCM (20 mL) and the mixture was stirred at room temperature for 12 hr. Water was added to quench the reaction and the mixture was extracted with DCM. The solvent was removed under and the residue was purified by silica gel chromatography with ethyl acetate/methanol (9/1, v/v) to afford the title compound (460 mg, 88% yield) as a slightly yellow oil. $^1$H NMR (400 MHz, CDCl$_3$) δ ppm 7.62 (s, 1H), 6.76 (s, 1H), 5.42 (s, 1H), 4.65-4.56 (m, 1H), 2.38 (s, 3H), 2.28 (s, 3H), 2.22 (s, 2H), 1.37 (d, J=6.1 Hz, 6H), 1.24 (s, 6H), 1.20 (s, 6H).

Step B: Synthesis of 2-isopropoxy-5-methyl-4-(1,2,2,6,6-pentamethyl-1,2,3,6-tetrahydropyridin-4-yl) aniline To a solution of 4-(5-isopropoxy-2-methyl-4-nitrophenyl)-1,2,2,6,6-pentamethyl-1,2,3,6-tetrahydropyridine (460 mg, 1.33 mmol) in 20 mL of ethanol was added several drops of 10% HCl, followed by iron powder (448 mg, 8.0 mmol). The mixture was stirred at 60° C. for 3 hr. The reaction was cooled to room temperature and the iron powder was filtered off. Ethanol was removed under reduced pressure and the title compound was obtained as colorless oil (410 mg, 98% yield). MS m/z=317 [M+H]. $^1$H NMR (400 MHz, CDCl$_3$) δ 6.53 (s, 2H), 5.32 (s, 1H), 4.40-4.40 (m, 1H), 3.67 (s, 2H), 2.35 (s, 3H), 2.19 (s, 3H), 2.20-2.17 (m, 2H), 1.33 (d, J=6.1 Hz, 6H), 1.20 (s, 6H), 1.17 (s, 6H).

Step C: Synthesis of 5-chloro-N$^2$-(2-isopropoxy-5-methyl-4-(1,2,2,6,6-pentamethyl-1,2,3,6-tetrahydropyridin-4-yl)phenyl)-N$^4$-(2-(isopropylsulfonyl)phenyl) pyrimidine-2,4-diamine

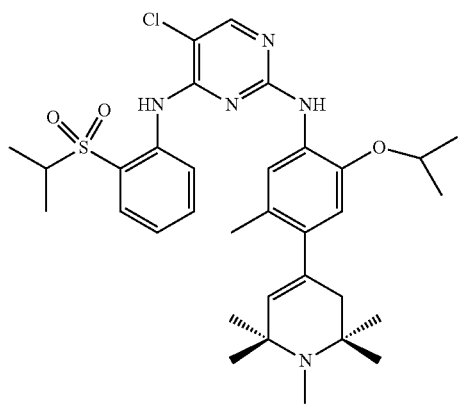

2-Isopropoxy-5-methyl-4-(1,2,2,6,6-pentamethyl-1,2,3,6-tetrahydropyridin-4-yl) aniline (154 mg, 0.488 mmol), 2,5-dichloro-N-(2-(isopropylsulfonyl)phenyl) pyrimidin-4-amine (168 mg, 0.488 mmol), Xantphos (28 mg, 0.0488 mmol), Pd(OAc)$_2$ (5.5 mg, 0.0244 mmol), and Cs$_2$CO$_3$ (477 mg, 1.464 mmol) were dissolved in anhydrous THF (10 mL). N$_2$ was bubbled through the reaction mixture for 5 min, and then the reaction vessel was sealed and heated under microwave irradiation to 150° C. for 30 min. The mixture was filtered and the filtrate concentrated under reduced pressure. After concentration, the crude product was purified by prep-HPLC (gradient from 10% to 60% acetonitrile in water) to give the title compound (110 mg, 36% yield). $^1$H NMR (400 MHz, CD$_3$OD) δ 8.36 (d, J=8.3 Hz, 1H), 8.25 (s, 1H), 8.00 (dd, J=7.9, 1.6 Hz, 1H), 7.80-7.62 (m, 2H), 7.55-7.40 (m, 1H), 6.78 (s, 1H), 5.62 (d, J=2.5 Hz, 1H), 4.72-4.55 (m, 1H), 3.42-3.33 (m, 1H), 2.98 (s, 3H), 2.95-2.82 (m, 1H), 2.44 (d, J=18.1 Hz, 1H), 2.15 (s, 3H), 1.65 (s, 3H), 1.61 (s, 3H), 1.59 (s, 3H), 1.56 (s, 3H), 1.34 (dd, J=6.0, 1.8 Hz, 6H), 1.27 (d, J=6.8 Hz, 6H).

Example 3

Synthesis of 5-chloro-N$^2$-(2-isopropoxy-5-methyl-4-(1-(tetrahydro-2H-pyran-4-yl)-1,2,3,6-tetrahydropyridin-4-yl)phenyl)-N$^4$-(2-(isopropylsulfonyl)phenyl)pyrimidine-2,4-diamine (Cpd. No. 5)

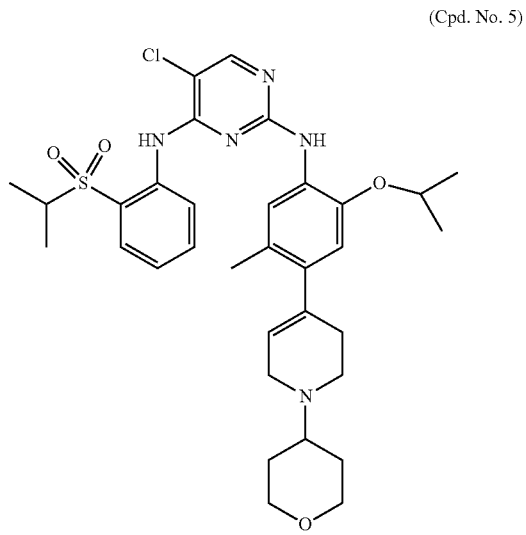 [SMILES: Cc1cc(Nc2ncc(Cl)c(Nc3ccccc3S(=O)(=O)C(C)C)n2)c(OC(C)C)cc1C1=CCN(C2CCOCC2)CC1]

Step A: Synthesis of tert-butyl 4-(5-fluoro-2-methyl-4-nitrophenyl)-3,6-dihydropyridine-1 (2H)-carboxylate

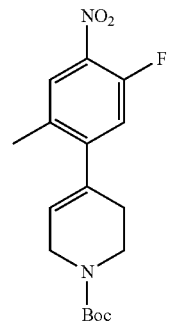 [SMILES: Cc1cc([N+](=O)[O-])c(F)cc1C1=CCN(C(=O)OC(C)(C)C)CC1]

Tert-butyl 4-(4,4,5,5-tetramethyl-1,3,2-dioxaborolan-2-yl)-3,6-dihydropyridine-1(2H)-carboxylate (620 mg, 2 mmol), Pd(dppf)Cl$_2$ (58 mg, 0.08 mmol), and K$_2$CO$_3$ (828 mg, 6 mmol) were added to a solution of 1-bromo-5-fluoro-2-methyl-4-nitrobenzene (470 mg, 2 mmol) in DME-H$_2$O (22 mL, 10:1 mixture). The mixture was stirred at 80° C. for 12 hr under nitrogen. The reaction was cooled to room temperature and the product was extracted with ethyl acetate. Solvent was removed under reduced pressure and the residue was purified by silica gel chromatography with hexane/ethyl acetate (9/1, v/v) to afford the title compound (640 mg, 95% yield) as a slightly yellow oil. $^1$H NMR (400 MHz, CDCl$_3$) δ ppm 7.89 (d, J=7.5 Hz, 1H), 7.02 (d, J=11.5 Hz, 1H), 5.68 (s, 1H), 4.10-4.07 (m, 2H), 3.65 (t, J=5.6 Hz, 2H), 2.39-2.32 (m, 2H), 2.33 (s, 3H), 1.52 (s, 9H).

Step B: Synthesis of tert-butyl 4-(5-isopropoxy-2-methyl-4-nitrophenyl)-3,6-dihydropyridine-1 (2H)-carboxylate

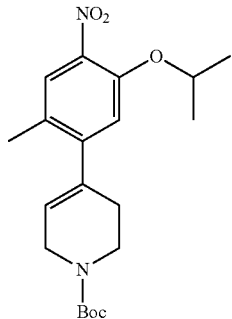

To a solution of tert-butyl 4-(5-fluoro-2-methyl-4-nitrophenyl)-3,6-dihydropyridine-1(2H)-carboxylate (640 mg, 1.9 mmol) in 20 mL of 2-propanol was added $Cs_2CO_3$ (1.862 g, 5.7 mmol). The mixture was stirred at 60° C. overnight, and after cooling to room temperature, most of the 2-propanol was evaporated under reduced pressure. Water was added, and the solution was extracted with ethyl acetate. The organic layers were combined, dried over anhydrous $Na_2SO_4$, concentrated, and the crude product was purified by silica gel chromatography with hexane/ethyl acetate (8/2, v/v) to afford the title compound (650 mg, 91%) as a yellow oil. $^1$H NMR (400 MHz, $CDCl_3$) δ 7.63 (s, 1H), 6.79 (s, 1H), 5.62 (s, 1H), 4.65-4.62 (m, 1H), 4.4.10-4.07 (m, 2H), 3.64 (t, J=5.6 Hz, 2H), 2.36-2.34 (m, 2H), 2.25 (s, 3H), 1.52 (s, 9H), 1.39 (d, J=6.1 Hz, 6H).

Step C: Synthesis of 4-(5-isopropoxy-2-methyl-4-nitrophenyl)-1-(tetrahydro-2H-pyran-4-yl)-1,2,3,6-tetrahydropyridine

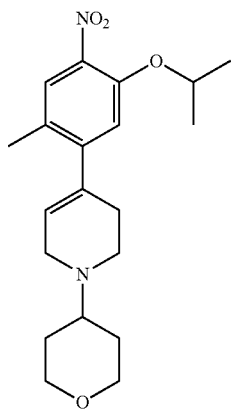

To a solution of tert-butyl 4-(5-isopropoxy-2-methyl-4-nitrophenyl)-5,6-dihydropyridine-1(2H)-carboxylate (217 mg, 0.576 mmol) in dichloromethane (5 mL) was added trifluoroacetic acid (1 mL) and the reaction mixture was stirred at room temperature for 6 hr. The dichloromethane and trifluoroacetic acid were removed under vacuum and 100 mL of dichloromethane was added, washed with saturated $NaHCO_3$ solution. The water layer was extracted with dichloromethane for additional two times (100 mL each). The organic layers were combined, washed with brine, dried over $Na_2SO_4$ and evaporated. The residue was dissolved in dichloromethane (10 mL) and tetrahydro-4H-pyran-4-one (173 mg, 1.728 mmol), sodium triacetoxyborohydride (244 mg, 1.152 mmol) and acetic acid (69 mg, 1.152 mmol) were then added. The reaction was stirred at room temperature overnight. The reaction was quenched by adding water (80 mL), and extracted with dichloromethane (3×100 mL). The organic layers were combined, washed with brine, dried over $Na_2SO_4$, concentrated and purified by silica gel column chromatography with ethyl acetate/methanol (9/1, v/v) to afford the title compound (170 mg, 82% for two steps) as a yellow oil. $^1$H NMR (400 MHz, $CDCl_3$) δ 7.63 (s, 1H), 6.83 (s, 1H), 5.62-5.59 (m, 1H), 4.58-4.56 (m, 1H), 4.11-4.01 (m, 2H), 3.43-3.28 (m, 4H), 2.78 (t, J=5.6 Hz, 2H), 2.60-2.56 (m, 1H), 2.40-2.36 (m, 2H), 2.23 (s, 3H), 1.86-1.82 (m, 2H), 1.69-1.65 (m, 2H), 1.35 (d, J=6.1 Hz, 6H).

Step D: Synthesis of 2-isopropoxy-5-methyl-4-(1-(tetrahydro-2H-pyran-4-yl)-1,2,3,6-tetrahydropyridin-4-yl)aniline

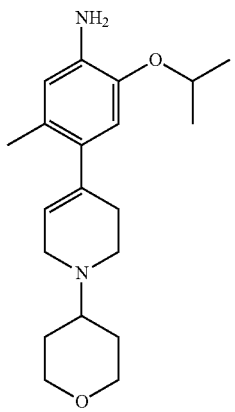 [SMILES: Cc1cc(N)c(OC(C)C)cc1C1=CCN(C2CCOCC2)CC1]

To a solution of 4-(5-isopropoxy-2-methyl-4-nitrophenyl)-1-(tetrahydro-2H-pyran-4-yl)-1,2,3,6-tetrahydropyridine (2.4 g, 6.66 mmol) in 30 mL of ethanol was added 4 mL of 10% HCl, followed by iron powder (2.23 g, 40 mmol). The mixture was stirred at 60° C. for 3 hr. The reaction was cooled to room temperature and the iron powder was filtered off. Ethanol was removed under reduced pressure and the title compound was obtained as pale yellow oil (2.0 g, 91% yield). MS m/z=331 [M+H].

Step E: Synthesis of 5-chloro-N²-(2-isopropoxy-5-methyl-4-(1-(tetrahydro-2H-pyran-4-yl)-1,2,3,6-tetrahydropyridin-4-yl)phenyl)-N⁴-(2-(isopropylsulfonyl)phenyl) pyrimidine-2,4-diamine

Example 4

Synthesis of 5-chloro-N²-(2-isopropoxy-5-methyl-4-(1-(oxetan-3-yl)-1,2,3,6-tetrahydropyridin-4-yl)phenyl)-N⁴-(2-(isopropylsulfonyl)phenyl)pyrimidine-2,4-diamine

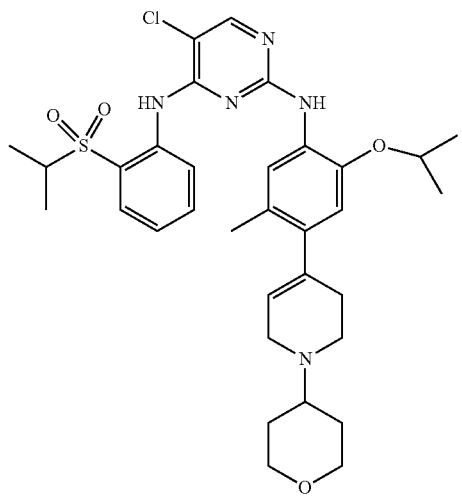 [SMILES: Cc1cc(Nc2ncc(Cl)c(Nc3ccccc3S(=O)(=O)C(C)C)n2)c(OC(C)C)cc1C1=CCN(C2CCOCC2)CC1]

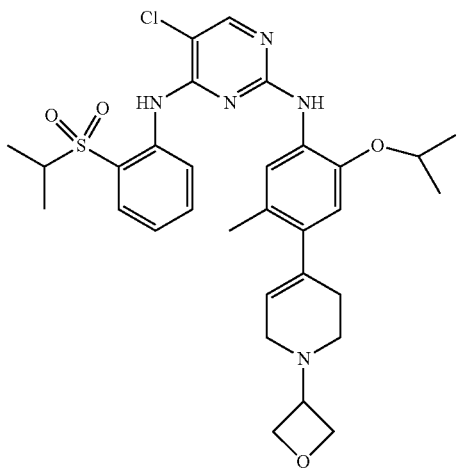

(Cpd. No. 6)

2-Isopropoxy-5-methyl-4-(1-(tetrahydro-2H-pyran-4-yl)-1,2,3,6-tetrahydropyridin-4-yl)aniline (330 mg, 1 mmol), 2,5-dichloro-N-(2-(isopropylsulfonyl)phenyl)pyrimidin-4-amine (345 mg, 1 mmol), Xantphos (58 mg, 0.1 mmol), Pd(OAc)₂ (11 mg, 0.05 mmol), and Cs₂CO₃ (975 mg, 3 mmol) were dissolved in anhydrous THF (20 mL). N₂ was bubbled through the reaction mixture for 5 min, and then the reaction vessel was sealed and heated under microwave irradiation to 150° C. for 30 min. The mixture was filtered and the filtrate concentrated under reduced pressure. After concentration, the crude product was purified by prep-HPLC (gradient from 10% to 60% acetonitrile in water) to the title compound (125 mg, 20% yield). ¹H NMR (400 MHz, DMSO-d₆) δ 9.46 (s, 1H), 8.46 (d, J=8.3 Hz, 1H), 8.27 (s, 1H), 8.06 (s, 1H), 7.85 (dd, J=8.3, 1.5 Hz, 1H), 7.66 (t, J=8.3 Hz, 1H), 7.59 (s, 1H), 7.37 (t, J=7.6 Hz, 1H), 6.73 (s, 1H), 5.57-5.50 (m, 1H), 4.58-4.54 (m, 1H), 3.96-3.87 (m, 2H), 3.47-3.43 (m, 1H), 3.31 (t, J=11.1 Hz, 2H), 3.17 (d, J=3.1 Hz, 2H), 2.70 (t, J=5.5 Hz, 2H), 2.29 (t, J=4.5 Hz, 2H), 2.07 (s, 3H), 1.78-1.74 (m, 2H), 1.49-1.45 (m, 2H), 1.23 (d, J=6.0 Hz, 6H), 1.16 (d, J=6.8 Hz, 6H).

Step A: Synthesis of tert-butyl 4-(4-amino-5-isopropoxy-2-methylphenyl)-3,6-dihydropyridine-1(2H)-carboxylate

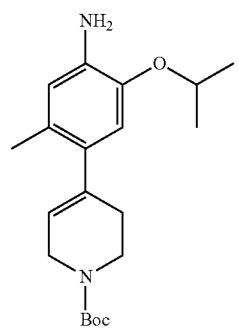 [SMILES: Cc1cc(N)c(OC(C)C)cc1C1=CCN(C(=O)OC(C)(C)C)CC1]

To a solution of tert-butyl 4-(5-isopropoxy-2-methyl-4-nitrophenyl)-3,6-dihydropyridine-1(2H)-carboxylate (217 mg, 0.576 mmol) in 20 mL of ethanol was added several drops of 10% HCl, followed by iron powder (194 mg, 3.457 mmol). The mixture was stirred at 60° C. for 3 hr. The reaction was cooled to room temperature and the iron powder was filtered off. Ethanol was removed under reduced pressure and the title compound was obtained as a pale yellow oil. This product was used directly without further purification.

Step B: Synthesis of 5-chloro-N²-(2-isopropoxy-5-methyl-4-(1-(oxetan-3-yl)-1,2,3,6-tetrahydropyridin-4-yl)phenyl)-N⁴-(2-(isopropylsulfonyl)phenyl)pyrimidine-2,4-diamine

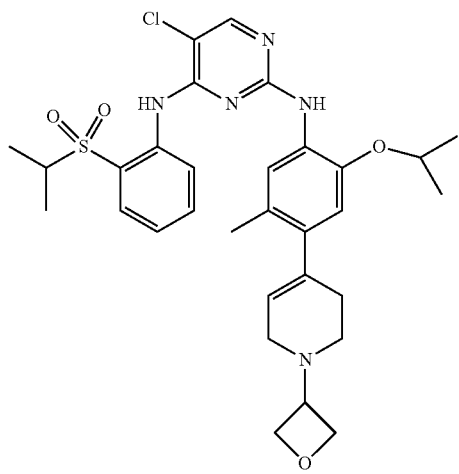 [SMILES: Cc1cc(Nc2ncc(Cl)c(Nc3ccccc3S(=O)(=O)C(C)C)n2)c(OC(C)C)cc1C1=CCN(C2COC2)CC1]

Tert-butyl 4-(4-amino-5-isopropoxy-2-methylphenyl)-3,6-dihydropyridine-1(2H)-carboxylate (120 mg, 0.348 mmol), 2,5-dichloro-N-(2-(isopropylsulfonyl)phenyl)pyrimidin-4-amine (120 mg, 0.348 mmol), Xantphos (28 mg, 0.048 mmol), Pd(OAc)₂ (5.5 mg, 0.024 mmol), and Cs₂CO₃ (400 mg, 1.23 mmol) were dissolved in anhydrous THF (8 mL). N₂ was bubbled through the reaction mixture for 5 min, and then the reaction vessel was sealed and heated under microwave irradiation to 150° C. for 30 min. The mixture was filtered and the filtrate concentrated under reduced pressure. The residue was dissolved in dichloromethane (5 mL). Trifluoroacetic acid (1 mL) was added and the reaction was stirred at room temperature for 6 hr. The dichloromethane and trifluoroacetic acid were removed under vacuum and 40 mL of dichloromethane was added, washed with saturated NaHCO₃ solution. The water layer was extracted with dichloromethane for additional two times (40 mL each). The organic layers were combined, washed with brine, dried over Na₂SO₄ and evaporated. The residue was dissolved in dichloromethane (10 mL) and oxetan-3-one (75 mg, 1.04 mmol), sodium triacetoxyborohydride (118 mg, 0.56 mmol) and acetic acid (34 mg, 0.56 mmol) were then added. The reaction was stirred at room temperature overnight. The reaction was quenched by adding water (80 mL), and extracted with dichloromethane (3×40 mL). The organic layers were combined, washed with brine, dried over Na₂SO₄. After concentration, the crude product was purified by prep-HPLC (gradient from 10% to 60% acetonitrile in water) to give the title compound (40 mg, 19% yield). ¹H NMR (400 MHz, CD₃OD) δ ppm 8.38 (d, J=8.0 Hz, 1H), 8.23 (s, 1H), 8.00-7.98 (m, 1H), 7.78-7.69 (m, 2H), 7.48-7.44 (m, 1H), 6.82 (s, 1H), 5.69-5.62 (m, 1H), 5.02-4.90 (m, 4H), 4.70-4.55 (m, 2H), 4.00-3.80 (m, 2H), 3.65-3.40 (m, 2H), 3.42-3.35 (m, 1H), 2.74 (s, 2H), 2.14 (s, 3H), 1.34 (d, J=6.1 Hz, 6H), 1.27 (d, J=6.8 Hz, 6H).

Example 5

Synthesis of 5-chloro-N²-(4-((cis)-2,6-dimethyl-1,2,3,6-tetrahydropyridin-4-yl)-2-isopropoxy-5-methylphenyl)-N⁴-(2-(isopropylsulfonyl)phenyl pyrimidine-2,4-diamine (Cpd. No. 9)

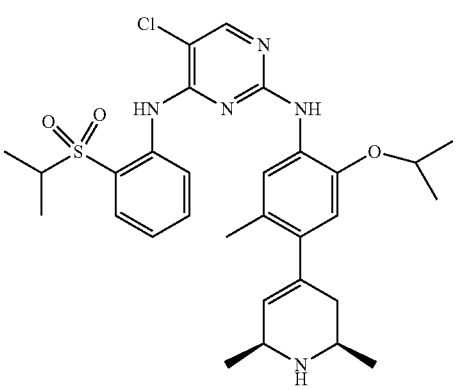

Step A: Synthesis of cis-1-(4-methoxybenzyl)-2,6-dimethylpiperidin-4-one

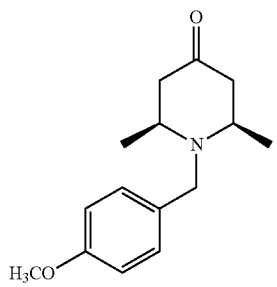 [SMILES: COc1ccc(CN2[C@H](C)CC(=O)C[C@@H]2C)cc1]

To a solution of acetone dicarboxylic acid (4 g, 27.4 mmol) in water (20 mL) was added 40% acetaldehyde (6 g, 54.8 mmol). Then 4-methoxyphenylmethanamine (3.75 g, 27.4 mmol) was added in small portions over 10 min. The resulting yellow solution was stirred at room temperature for three days. The reaction mixture was extracted with dichloromethane (3×60 mL). Combined extracts were washed with brine and dried with anhydrous Na₂SO₄. The solution was filtered and evaporated to give brown residue. The isomeric piperidones were separated by silica gel chromatography with dichloromethane/ethyl acetate (9/1, v/v). The desired title compound (4.0 g, 59%) was obtained as a pale yellow oil. ¹H NMR (400 MHz, CDCl₃) δ 7.30 (d, J=8.5 Hz, 2H), 6.87 (d, J=8.5 Hz, 2H), 3.86 (d, J=13.7 Hz, 1H), 3.81 (s, 3H), 3.55 (d, J=13.7 Hz, 1H), 3.28-3.24 (m, 2H), 2.49-2.45 (m, 2H), 2.20-2.16 (m, 2H), 1.09 (d, J=6.6 Hz, 6H).

Step B: Synthesis of cis-2,6-dimethylpiperidin-4-one

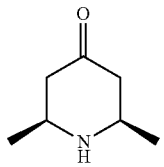

Cis-1-(4-methoxybenzyl)-2,6-dimethylpiperidin-4-one (4.0 g, 16.2 mmol) was dissolved in ethanol (20 mL) and catalyst (0.4 g, 10% Pd—C) was added. The mixture was stirred under hydrogen atmosphere for 12 hr. The catalyst was removed by filtration and the filtrate was evaporated under reduced pressure to give the title compound (1.8 g, 88% yield). $^1$H NMR (400 MHz, CDCl$_3$) δ 3.58-3.50 (m, 2H), 2.50-2.48 (m, 2H), 2.20-2.11 (m, 2H), 1.17 (d, J=6.6 Hz, 6H).

Step C: tert-butyl-cis-2,6-dimethyl-4-oxopiperidine-1-carboxylate

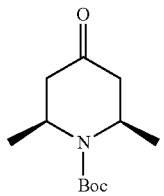

Di-tert-butyl dicarbonate (3.14 g, 14.4 mmol) and N,N-diisopropylethylamine (3.1 g, 24 mmol) were added to a solution of cis-1-(4-methoxybenzyl)-2,6-dimethylpiperidin-4-one (1.54 g, 12 mmol) in dichloromethane (30 mL) and the mixture was stirred at room temperature for 12 hr. Solvent was removed under reduced pressure and the residue was purified by silica gel chromatography with hexane/ethyl acetate (8/2, v/v) to afford the title compound (2.0 g, 73% yield) as a white solid. $^1$H NMR (400 MHz, CDCl$_3$) δ 4.41-4.39 (m, 2H), 2.85 (dd, J=17.8, 6.5 Hz, 2H), 2.37 (dd, J=17.8, 1.9 Hz, 2H), 1.50 (s, 9H), 1.25 (d, J=6.8 Hz, 6H).

Step D: Synthesis of tert-butyl-cis-2,6-dimethyl-4-(((trifluoromethyl) sulfonyl)oxy)-3,6-dihydropyridine-1(2H)-carboxylate

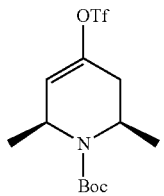

To a solution of tert-butyl-cis-2,6-dimethyl-4-oxopiperidine-1-carboxylate (500 mg, 2.2 mmol) in THF (20 mL) was slowly added 2.0 M LDA (1.1 mL, 2.2 mmol) in THF at −78° C. After 20 min, a solution of 1,1,1-trifluoro-N-phenyl-N-(trifluoromethylsulfonyl)methanesulfonamide (786 mg, 2.2 mmol) was slowly added to the mixture. The reaction mixture was stirred at 0° C. for 3 h. The solvent was evaporated under reduced pressure, and the residue was purified by column chromatography with hexane/ethyl acetate (20/1, v/v) to obtain the title compound (600 mg, 76% yield). $^1$H NMR (400 MHz, CDCl$_3$) δ 5.78-5.70 (m, 1H), 4.45-4.30 (m, 2H), 2.85-2.78 (m, 1H), 2.25-2.15 (m, 1H), 1.48 (s, 9H), 1.37 (d, J=6.3 Hz, 3H), 1.24 (d, J=6.5 Hz, 3H).

Step E: Synthesis of tert-butyl-cis-2,6-dimethyl-4-(4,4,5,5-tetramethyl-1,3,2-dioxaborolan-2-yl)-3,6-dihydropyridine-1(2H)-carboxylate

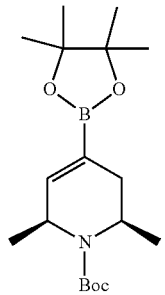

The suspension of tert-butyl-cis-2,6-dimethyl-4-(((trifluoromethyl)sulfonyl)oxy)-3,6-dihydropyridine-1(2H)-carboxylate (600 mg, 1.67 mmol), bis(pinacolato)diboron (467 mg, 1.84 mmol), potassium acetate (490 mg, 5.01 mmol), 1,10-bis(diphenylphosphino)ferrocene (47 mg, 0.084 mmol), and [1,10-bis(diphenylphosphino)ferrocene]dichloropalladium (II) complex in dichloromethane (61 mg, 0.084 mmol) were stirred in 1,4-dioxane (10 mL) at 80° C. for 12 h. The reaction mixture was extracted with ethyl acetate, and the organic layer was washed with brine, dried over anhydrous Na$_2$SO$_4$, and filtered. The solvent was evaporated under reduced pressure, and the residue was purified by column chromatography with hexane/ethyl acetate (9/1, v/v) to obtain the title compound (500 mg, 89% yield). $^1$H NMR (400 MHz, CDCl$_3$) δ 6.61-6.57 (m, 1H), 4.21-4.17 (m, 2H), 2.44-2.33 (m, 1H), 2.22-2.13 (m, 1H), 1.48 (s, 9H), 1.30-1.20 (m, 15H), 1.05 (d, J=6.4 Hz, 3H).

Step F: Synthesis of tert-butyl-cis-4-(5-fluoro-2-methyl-4-nitrophenyl)-2,6-dimethyl-3,6-dihydropyridine-1(2H)-carboxylate

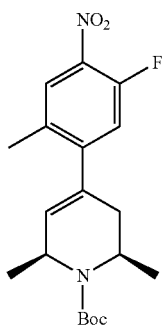 [SMILES: Cc1cc([N+](=O)[O-])c(F)cc1C1=C[C@H](C)N(C(=O)OC(C)(C)C)[C@H](C)C1]

Tert-butyl-cis-2,6-dimethyl-4-(4,4,5,5-tetramethyl-1,3,2-dioxaborolan-2-yl)-3,6-dihydropyridine-1(2H)-carboxylate (500 mg, 1.48 mmol), Pd(dppf)Cl$_2$ (43 mg, 0.06 mmol), and K$_2$CO$_3$ (613 mg, 4.44 mmol) were added to a solution of 1-bromo-5-fluoro-2-methyl-4-nitrobenzene (417 mg, 1.78 mmol) in DME-H$_2$O (22 mL, 10:1 mixture). The mixture was stirred at 80° C. for 12 hr under nitrogen. The reaction was cooled to room temperature and the product was extracted with ethyl acetate. Solvent was removed under reduced pressure and the residue was purified by silica gel chromatography with hexane/ethyl acetate (9/1, v/v) to afford the title compound (420 mg, 78% yield). $^1$H NMR (400 MHz, CDCl$_3$) δ 7.89 (d, J=7.5 Hz, 1H), 7.00 (d, J=11.5 Hz, 1H), 5.87-5.84 (m, 1H), 4.44-4.32 (m, 2H), 2.94-2.84 (m, 1H), 2.35 (s, 3H), 2.11-2.02 (m, 1H), 1.51 (s, 9H), 1.38 (d, J=6.4 Hz, 3H), 1.21 (d, J=6.4 Hz, 3H).

Step G: Synthesis of tert-butyl-cis-4-(5-isopropoxy-2-methyl-4-nitrophenyl)-2,6-dimethyl-3,6-dihydropyridine-1(2H)-carboxylate

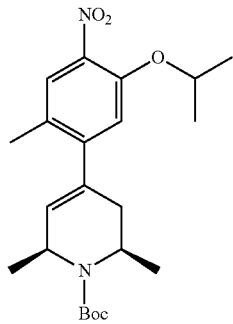 [SMILES: Cc1cc([N+](=O)[O-])c(OC(C)C)cc1C1=C[C@H](C)N(C(=O)OC(C)(C)C)[C@H](C)C1]

To a solution of tert-butyl-cis-4-(5-fluoro-2-methyl-4-nitrophenyl)-2,6-dimethyl-3,6-dihydropyridine-1(2H)-carboxylate (420 mg, 1.15 mmol) in 20 mL of 2-propanol was added Cs$_2$CO$_3$ (1.128 g, 3.46 mmol). The mixture was stirred at 60° C. overnight, and after cooling to room temperature, most of the 2-propanol was evaporated under reduced pressure. Water was added, and the solution was extracted with ethyl acetate. The organic layers were combined, dried over Na$_2$SO$_4$, concentrated, and the crude product was purified by silica gel chromatography with hexane/ethyl acetate (9/1, v/v) to afford the title compound (450 mg, 97%) as a slightly yellow oil. $^1$H NMR (400 MHz, CDCl$_3$) δ 7.63 (s, 1H), 6.77 (s, 1H), 5.82-5.79 (m, 1H), 4.63-4.60 (m, 1H), 4.38-4.34 (m, 2H), 2.92-2.87 (m, 1H), 2.27 (s, 3H), 2.11-2.00 (m, 1H), 1.51 (s, 9H), 1.39-1.36 (m, 9H), 1.21 (d, J=6.3 Hz, 3H).

Step H: Synthesis of tert-butyl-cis-4-(4-amino-5-isopropoxy-2-methylphenyl)-2,6-dimethyl-3,6-dihydropyridine-1(2H)-carboxylate

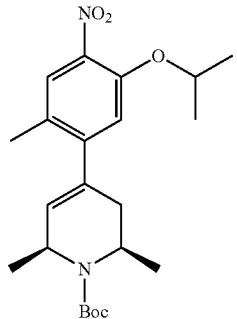 [SMILES: Cc1cc([N+](=O)[O-])c(OC(C)C)cc1C1=C[C@H](C)N(C(=O)OC(C)(C)C)[C@H](C)C1]

To a solution of tert-buty-cis-4-(5-isopropoxy-2-methyl-4-nitrophenyl)-2,6-dimethyl-3,6-dihydropyridine-1(2H)-carboxylate (230 mg, 0.569 mmol) in 20 mL of ethanol was added several drops of 10% HCl, followed by iron powder (191 mg, 3.42 mmol). The mixture was stirred at 60° C. for 3 hr. The reaction was cooled to room temperature and the iron powder was filtered off. Ethanol was removed under reduced pressure and the title compound was obtained as pale yellow oil. This product was used directly without further purification.

Step I: Synthesis of 5-chloro-N$^2$-(4-(cis-2,6-dimethyl-1,2,3,6-tetrahydropyridin-4-yl)-2-isopropoxy-5-methylphenyl)-N$^4$-(2-(isopropylsulfonyl)phenyl)pyrimidine-2,4-diamine

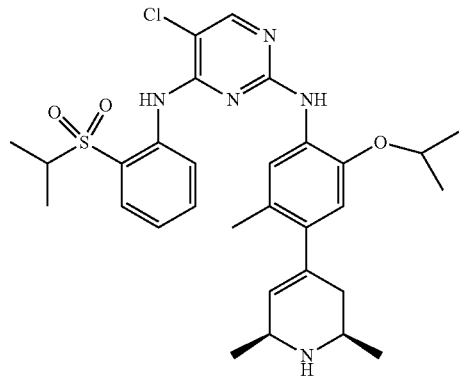 [SMILES: Cc1cc(Nc2ncc(Cl)c(Nc3ccccc3S(=O)(=O)C(C)C)n2)c(OC(C)C)cc1C1=C[C@H](C)N[C@H](C)C1]

Tert-butyl-cis-4-(4-amino-5-isopropoxy-2-methylphenyl)-2,6-dimethyl-3,6-dihydropyridine-1(2H)-carboxylate (213 mg, 0.57 mmol), 2,5-dichloro-N-(2-(isopropylsulfonyl)phenyl)pyrimidin-4-amine (197 mg, 0.57 mmol), Xantphos (33 mg, 0.057 mmol), Pd(OAc)$_2$ (6 mg, 0.029 mmol), and Cs$_2$CO$_3$ (555 mg, 1.71 mmol) were dissolved in anhydrous THF (20 mL). N$_2$ was bubbled through the reaction mixture for 5 min, and then the reaction vessel was sealed and heated under microwave irradiation to 150° C. for 30 min. The mixture was filtered and the filtrate concentrated under reduced pressure. The residue was dissolved in dichloromethane (5 mL). Trifluoroacetic acid (1 mL) was added and the reaction was stirred at room temperature for 6 hr. The dichloromethane and trifluoroacetic acid were removed under vacuum. The residue was purified by prep-HPLC (gradient from 10% to 60% acetonitrile in water) to give the title compound (110 mg, 33% yield). $^1$H NMR (400 MHz, CD$_3$OD) δ 8.35 (d, J=8.3 Hz, 1H), 8.24 (s, 1H), 7.99 (d, J=7.7 Hz, 1H), 7.74 (t, J=7.7 Hz, 1H), 7.64 (s, 1H), 7.49 (t, J=7.7 Hz, 1H), 6.80 (s, 1H), 5.65-5.59 (m, 1H), 4.65-4.61 (m, 1H), 4.21-4.17 (m, 1H), 3.82-3.78 (m, 1H), 3.41-3.37 (m, 1H), 2.70-2.60 (m, 1H), 2.40-2.36 (m, 1H), 2.12 (s, 3H), 1.54 (d, J=6.9 Hz, 3H), 1.49 (d, J=6.5 Hz, 3H), 1.33 (d, J=6.0 Hz, 6H), 1.26 (d, J=6.8 Hz, 6H).

Example 6

Synthesis of 5-chloro-N$^2$-(2-isopropoxy-5-methyl-4-((cis)-1,2,6-trimethyl-1,2,3,6-tetrahydropyridin-4-yl)phenyl)-N$^4$-(2-(isopropylsulfonyl)phenyl)pyrimidine-2,4-diamine (Cpd. No. 10)

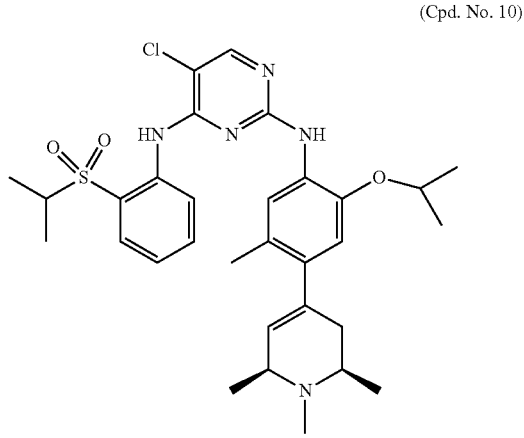 [SMILES: Cc1cc(Nc2ncc(Cl)c(Nc3ccccc3S(=O)(=O)C(C)C)n2)c(OC(C)C)cc1C1=C[C@H](C)N(C)[C@H](C)C1]

Step A: Synthesis of cis-4-(5-isopropoxy-2-methyl-4-nitrophenyl)-1,2,6-trimethyl-1,2,3,6-tetrahydropyridine

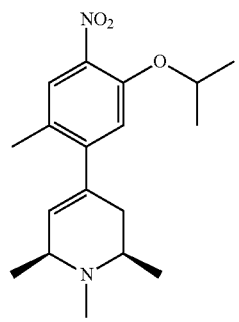 [SMILES: Cc1cc([N+](=O)[O-])c(OC(C)C)cc1C1=C[C@H](C)N(C)[C@H](C)C1]

To a solution of tert-butyl-cis-4-(5-isopropoxy-2-methyl-4-nitrophenyl)-2,6-dimethyl-3,6-dihydropyridine-1 (2H)-carboxylate (230 mg, 0.57 mmol) in dichloromethane (5 mL) was added trifluoroacetic acid (1 mL) and the reaction mixture was stirred at room temperature for 6 hr. The dichloromethane and trifluoroacetic acid were removed under vacuum and 100 mL of dichloromethane was added, washed with saturated NaHCO$_3$ solution. The water layer was extracted with dichloromethane for additional two times (100 mL each). The organic layers were combined, washed with brine, dried over Na$_2$SO$_4$ and evaporated. The residue was dissolved in dichloromethane (10 mL) and 37% formaldehyde (138 mg, 1.71 mmol), sodium triacetoxyborohydride (181 mg, 0.855 mmol) and acetic acid (51 mg, 0.855 mmol) were then added. The reaction was stirred at room temperature overnight. The reaction was quenched by adding water (80 mL), and extracted with dichloromethane (3×100 mL). The organic layers were combined, washed with brine, dried over Na$_2$SO$_4$, concentrated and purified by silica gel column chromatography with ethyl acetate/methanol (9/1, v/v) to afford the title compound (190 mg, 91% for two steps) as a yellow oil. $^1$H NMR (400 MHz, CDCl$_3$) δ 7.61 (s, 1H), 6.79 (s, 1H), 5.50-5.46 (m, 1H), 4.60-4.56 (m, 1H), 3.27-3.09 (m, 2H), 2.55-2.51 (m, 1H), 2.43 (s, 3H), 2.25 (s, 3H), 2.01-1.97 (m, 1H), 1.36 (dd, J=6.0, 2.2 Hz, 6H), 1.21 (d, J=6.7 Hz, 3H), 1.12 (d, J=6.5 Hz, 3H).

Step B: Synthesis of 2-isopropoxy-5-methyl-4-(cis-1,2,6-trimethyl-1,2,3,6-tetrahydropyridin-4-yl)aniline

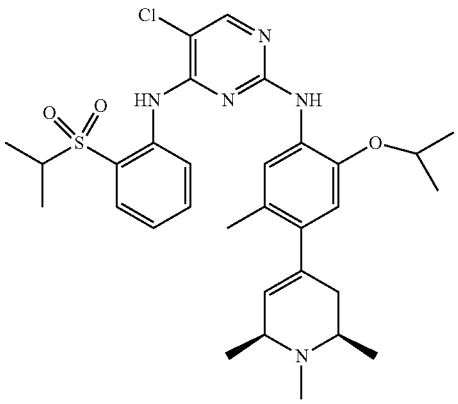 [SMILES: Cc1cc(Nc2ncc(Cl)c(Nc3ccccc3S(=O)(=O)C(C)C)n2)c(OC(C)C)cc1C1=C[C@H](C)N(C)[C@H](C)C1]

To a solution of cis-4-(5-isopropoxy-2-methyl-4-nitrophenyl)-1,2,6-trimethyl-1,2,3,6-tetrahydropyridine (181 mg, 0.57 mmol) in 20 mL of ethanol was added several drops of 10% HCl, followed by iron powder (191 mg, 3.42 mmol). The mixture was stirred at 60° C. for 3 hr. The reaction was cooled to room temperature and the iron powder was filtered off. Ethanol was removed under reduced pressure and the title compound was obtained as yellow oil. This product was used directly without further purification.

Step C: Synthesis of 5-chloro-N$^2$-(2-isopropoxy-5-methyl-4-(cis-1,2,6-trimethyl-1,2,3,6-tetrahydropyridin-4-yl)phenyl)-N$^4$-(2-(isopropylsulfonyl)phenyl)pyrimidine-2,4-diamine 2-Isopropoxy-5-methyl-4-(cis-1,2,6-trimethyl-1,2,3,6-tetrahydropyridin-4-yl)aniline (164 mg, 0.57 mmol), 2,5-dichloro-N-(2-(isopropylsulfonyl)phenyl)pyrimidin-4-amine (197 mg, 0.57 mmol), Xantphos (33 mg, 0.057 mmol), Pd(OAc)$_2$ (6 mg, 0.029 mmol), and Cs$_2$CO$_3$ (555 mg, 1.71 mmol) were dissolved in anhydrous THF (20 mL). N$_2$ was bubbled through the reaction mixture for 5 min, and then the reaction vessel was sealed and heated under microwave irradiation to 150° C. for 30 min. The mixture was filtered and the filtrate concentrated under reduced pressure. The residue was purified by prep-HPLC (gradient from 10% to 60% acetonitrile in water) to give the title compound (50 mg, 15% yield). $^1$H NMR (400 MHz, CD$_3$OD) δ 8.35 (d, J=8.2 Hz, 1H), 8.24 (s, 1H), 7.81-7.89 (m, 1H), 7.76-7.71 (m, 1H), 7.65 (s, 1H), 7.51-7.47 (m, 1H), 6.84 (s, 1H), 5.59-5.57 (m, 1H), 4.68-4.64 (m, 1H), 4.08-3.95 (m, 2H), 3.42-3.36 (m, 1H), 2.97 (s, 3H), 2.81-2.71 (m, 1H), 2.46-2.44 (m, 1H), 2.13 (s, 3H), 1.60 (d, J=6.8 Hz, 3H), 1.50 (d, J=5.5 Hz, 3H), 1.33 (d, J=6.0 Hz, 6H), 1.27 (d, J=6.8 Hz, 6H).

Example 7

Synthesis of 5-chloro-N$^2$-(4-((cis)-2,6-dicyclopropyl-1,2,3,6-tetrahydropyridin-4-yl)-2-isopropoxy-5-methylphenyl)-N$^4$-(2-(isopropylsulfonyl)phenyl)pyrimidine-2,4-diamine (Cpd .No. 15)

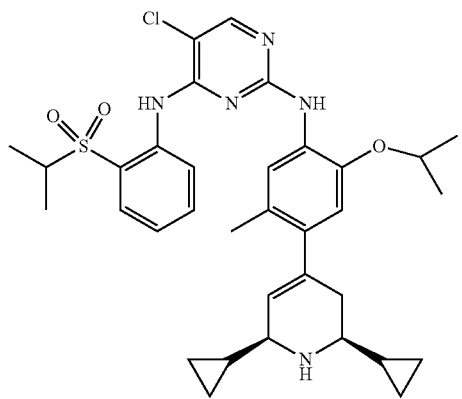

Step A: Synthesis of cis-2,6-dicyclopropyl-1-(4-methoxybenzyl)piperidin-4-one

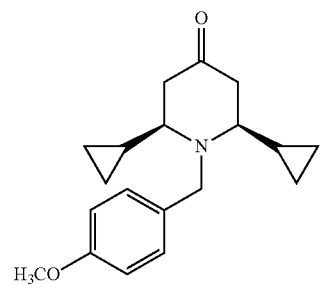 [SMILES: COc1ccc(CN2[C@@H](C3CC3)CC(=O)C[C@H]2C2CC2)cc1]

To a solution of acetone dicarboxylic acid (3.0 g, 20.5 mmol) in water (20 mL) was added cyclopropanecarbaldehyde (2.876 g, 41 mmol). Then 4-methoxyphenylmethanamine (2.8 g, 20.5 mmol) was added in small portions over 10 min. The resulting yellow solution was stirred at room temperature for three days. The reaction mixture was extracted with dichloromethane (3×60 mL). Combined extracts were washed with brine and dried with anhydrous Na$_2$SO$_4$. The solution was filtered and evaporated to give brown residue. The isomeric piperidones were separated by silica gel chromatography with hexane/ethyl acetate (7/1, v/v). The desired title compound (34.0 g, 54%) was obtained as a pale yellow oil. $^1$H NMR (400 MHz, CDCl$_3$) δ 7.35 (d, J=8.6 Hz, 2H), 6.88 (d, J=8.6 Hz, 2H), 4.34 (d, J=13.9 Hz, 1H), 3.95 (d, J=13.9 Hz, 1H), 3.83 (s, 3H), 2.64-2.38 (m, 6H), 0.81-0.77 (m, 2H), 0.71-0.38 (m, 4H), 0.35-0.30 (m, 2H), 0.10-0.03 (m, 2H).

Step B: Synthesis of cis-2,6-dicyclopropylpiperidin-4-one

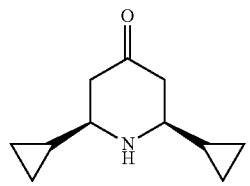 [SMILES: O=C1C[C@@H](C2CC2)N[C@@H](C2CC2)C1]

Cis-2,6-dicyclopropyl-1-(4-methoxybenzyl)piperidin-4-one (3.0 g, 11 mmol) was dissolved in ethanol (20 mL) and catalyst (0.3 g, 10% Pd—C) was added. The mixture was stirred under hydrogen atmosphere for 12 hr. The catalyst was removed by filtration and the filtrate was evaporated under reduced pressure to give the title compound (1.52 g, 91% yield). This product was used directly in the next step without further purification.

Step C: Synthesis of tert-butyl-cis-2,6-dicyclopropyl-4-oxopiperidine-1-carboxylate

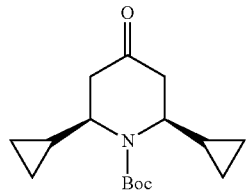 [SMILES: CC(C)(C)OC(=O)N1[C@@H](C2CC2)CC(=O)C[C@H]1C1CC1]

Di-tert-butyl dicarbonate (1.73 g, 7.95 mmol) and N,N-diisopropylethylamine (1.71 g, 13.24 mmol) were added to a solution of cis-2,6-dicyclopropylpiperidin-4-one (1.0 g, 6.62 mmol) in dichloromethane (20 mL) and the mixture was stirred at room temperature for 12 hr. Solvent was removed under reduced pressure and the residue was purified by silica gel chromatography with hexane/ethyl acetate (9/1, v/v) to afford the title compound (0.85 g, 51% yield) as a colorless oil. $^1$H NMR (400 MHz, CDCl$_3$) δ 3.83-3.81 (m, 2H), 2.90 (dd, J=17.4, 6.0 Hz, 2H), 2.54 (dd, J=17.4, 2.7 Hz, 2H), 1.52 (s, 9H), 0.91-0.88 (m, 2H), 0.75-0.72 (m, 2H), 0.62-0.43 (m, 4H), 0.18-0.15 (m, 2H).

Step D: Synthesis of tert-butyl-cis-2,6-dicyclopropyl-4-(((trifluoromethyl) sulfonyl)oxy)-3,6-dihydropyridine-1(2H)-carboxylate

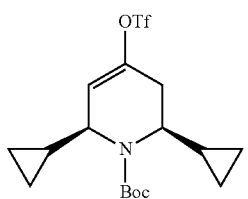 [SMILES: CC(C)(C)OC(=O)N1[C@@H](C2CC2)C=C(OS(=O)(=O)C(F)(F)F)C[C@H]1C1CC1]

To a solution of tert-butyl-cis-2,6-dicyclopropyl-4-oxopiperidine-1-carboxylate (1.7 g, 6.77 mmol) in THF (20 mL) was slowly added 2.0 M LDA (3.39 mL, 6.78 mmol) in THF at −78° C. After 20 min, a solution of 1,1,1-trifluoro-N-phenyl-N-(trifluoromethylsulfonyl)methanesulfonamide (2.417 g, 6.77 mmol) was slowly added to the mixture. The reaction mixture was stirred at 0° C. for 3 hr. The solvent was evaporated under reduced pressure, and the residue was purified by column chromatography with hexane/ethyl acetate (20/1, v/v) to obtain the title compound (1.6 g, 58% yield). $^1$H NMR (400 MHz, CDCl$_3$) δ 5.77 (d, J=4.7 Hz, 1H), 4.20-4.18 (m, 1H), 2.82-2.84 (m, 1H), 2.73-2.61 (m, 1H), 2.57-2.49 (m, 1H), 1.55-1.53 (m, 1H), 1.49 (s, 9H), 1.09-1.06 (m, 1H), 0.62-0.42 (m, 6H), 0.35-0.25 (m, 1H), 0.22-0.11 (m, 1H).

Step E: Synthesis of tert-butyl cis-2,6-dicyclopropyl-4-(4,4,5,5-tetramethyl-1,3,2-dioxaborolan-2-yl)-3,6-dihydropyridine-1(2H)-carboxylate

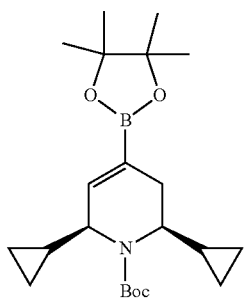 [SMILES: CC(C)(C)OC(=O)N1[C@@H](C2CC2)C=C(B2OC(C)(C)C(C)(C)O2)C[C@H]1C1CC1]

The suspension of tert-butyl-cis-2,6-dicyclopropyl-4-(((trifluoromethyl) sulfonyl)oxy)-3,6-dihydropyridine-1(2H)-carboxylate (1.6 g, 4.13 mmol), bis(pinacolato) diboron (1.255 mg, 4.96 mmol), potassium acetate (1.214 mg, 12.39 mmol), 1,10-bis(diphenylphosphino) ferrocene (114 mg, 0.21 mmol), and [1,10-bis(diphenylphosphino)ferrocene]dichloropalladium (II) complex in dichloromethane (154 mg, 0.21 mmol) were stirred in 1,4-dioxane (20 mL) at 80° C. for 12 hr. The reaction mixture was extracted with ethyl acetate, and the organic layer was washed with brine, dried over anhydrous Na$_2$SO$_4$, and filtered. The solvent was evaporated under reduced pressure, and the residue was purified by column chromatography with hexane/ethyl acetate (9/1, v/v) to obtain the title compound (1.6 g, 99% yield). $^1$H NMR (400 MHz, CDCl$_3$) δ 6.49 (d, J=4.7 Hz, 1H), 4.07-4.05 (m, 1H), 2.80-2.78 (m, 1H), 2.50-2.38 (m, 1H), 2.30-2.28 (m, 1H), 1.48 (s, 9H), 1.39-1.25 (m, 1H), 1.28 (s, 12H), 1.08-1.00 (m, 1H), 0.55-0.37 (m, 6H), 0.30-0.20 (m, 1H), 0.14-0.05 (m, 1H).

Step F: Synthesis of tert-butyl-cis-2,6-dicyclopropyl-4-(5-fluoro-2-methyl-4-nitrophenyl)-3,6-dihydropyridine-1(2H)-carboxylate

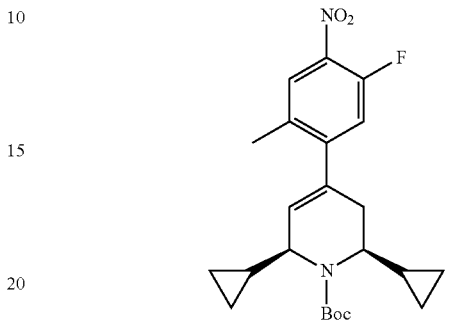

Tert-butyl-cis-2,6-dicyclopropyl-4-(4,4,5,5-tetramethyl-1,3,2-dioxaborolan-2-yl)-3,6-dihydropyridine-1(2H)-carboxylate (1.35 g, 3.74 mmol), Pd(dppf)Cl$_2$ (109 mg, 0.15 mmol), and K$_2$CO$_3$ (1.55 g, 11.22 mmol) were added to a solution of 1-bromo-5-fluoro-2-methyl-4-nitrobenzene (1.05 g, 4.49 mmol) in DME-H$_2$O (22 mL, 10:1 mixture). The mixture was stirred at 80° C. for 12 hr under nitrogen. The reaction was cooled to room temperature and the product was extracted with ethyl acetate. Solvent was removed under reduced pressure and the residue was purified by silica gel chromatography with hexane/ethyl acetate (9/1, v/v) to afford the title compound (1.20 g, 77% yield). $^1$H NMR (400 MHz, CDCl$_3$) δ 7.90 (d, J=7.5 Hz, 1H), 7.04 (d, J=11.5 Hz, 1H), 5.80-5.65 (m, 1H), 4.30-4.26 (m, 1H), 3.30-3.20 (m, 1H), 2.65-2.55 (m, 1H), 2.49 (dd, J=16.2, 5.8 Hz, 1H), 2.37 (s, 3H), 1.53 (s, 9H), 1.40-1.30 (m, 1H), 0.95-0.83 (m, 1H), 0.68-0.49 (m, 6H), 0.35-0.14 (m, 2H).

Step G: Synthesis of tert-butyl-cis-2,6-dicyclopropyl-4-(5-isopropoxy-2-methyl-4-nitrophenyl)-3,6-dihydropyridine-1(2H)-carboxylate

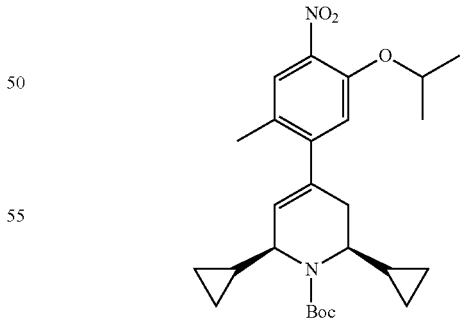

To a solution of tert-butyl-cis-2,6-dicyclopropyl-4-(5-fluoro-2-methyl-4-nitrophenyl)-3,6-dihydropyridine-1(2H)-carboxylate (670 mg, 1.61 mmol) in 20 mL of 2-propanol was added Cs$_2$CO$_3$ (1.574 g, 4.83 mmol). The mixture was stirred at 60° C. overnight, and after cooling to room temperature, most of the 2-propanol was evaporated under reduced pressure. Water was added, and the solution was extracted with ethyl acetate. The organic layers were combined, dried over Na$_2$SO$_4$, concentrated, and the crude product was purified by silica gel chromatography with hexane/ethyl acetate (9/1, v/v) to afford the title compound (700 mg, 95%) as a yellow oil. $^1$H NMR (400 MHz, CDCl$_3$) δ 7.65 (s, 1H), 6.82 (s, 1H), 5.70-5.66 (m, 1H), 4.66-4.56 (m, 1H), 4.33-4.30 (m, 1H), 3.28-3.20 (m, 1H), 2.67-2.56 (m, 1H), 2.47 (dd, J=16.0, 5.1 Hz, 1H), 2.28 (s, 3H), 1.53 (s, 9H), 1.42-1.24 (m, 2H), 1.40 (d, J=6.0 Hz, 6H), 0.70-0.44 (m, 6H), 0.34-0.25 (m, 1H), 0.20-0.10 (m, 1H).

Step H: Synthesis of tert-butyl-cis-4-(4-amino-5-isopropoxy-2-methylphenyl)-2,6-dicyclopropyl-3,6-dihydropyridine-1(2H)-carboxylate

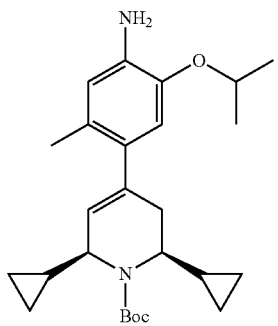 [SMILES: Cc1cc([N+](=O)[O-])c(OC(C)C)cc1C1=C[C@H](C2CC2)N(C(=O)OC(C)(C)C)[C@H](C2CC2)C1]

To a solution of tert-butyl-cis-2,6-dicyclopropyl-4-(5-isopropoxy-2-methyl-4-nitrophenyl)-3,6-dihydropyridine-1(2H)-carboxylate (380 mg, 0.833 mmol) in 20 mL of ethanol was added several drops of 10% HCl, followed by iron powder (280 mg, 5.0 mmol). The mixture was stirred at 60° C. for 3 hr. The reaction was cooled to room temperature and the iron powder was filtered off. Ethanol was removed under reduced pressure and the title compound was obtained as a pale yellow oil. This product was used directly without further purification.

Step I: Synthesis of 5-chloro-N$^2$-(4-((cis)-2,6-dicyclopropyl-1,2,3,6-tetrahydropyridin-4-yl)-2-isopropoxy-5-methylphenyl)-N$^4$-(2-(isopropylsulfonyl)phenyl)pyrimidine-2,4-diamine

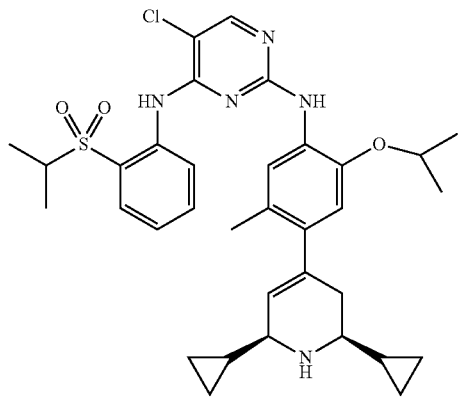 [SMILES: Cc1cc(Nc2ncc(Cl)c(Nc3ccccc3S(=O)(=O)C(C)C)n2)c(OC(C)C)cc1C1=C[C@H](C2CC2)N[C@H](C2CC2)C1]

Tert-butyl-cis-4-(4-amino-5-isopropoxy-2-methylphenyl)-2,6-dicyclopropyl-3,6-dihydropyridine-1(2H)-carboxylate (350 mg, 0.822 mmol), 2,5-dichloro-N-(2-(isopropylsulfonyl)phenyl)pyrimidin-4-amine (283 mg, 0.822 mmol), Xantphos (48 mg, 0.0822 mmol), Pd(OAc)$_2$ (9 mg, 0.0411 mmol), and Cs$_2$CO$_3$ (801 mg, 2.466 mmol) were dissolved in anhydrous THF (20 mL). N$_2$ was bubbled through the reaction mixture for 5 min, and then the reaction vessel was sealed and heated under microwave irradiation to 150° C. for 30 min. The mixture was filtered and the filtrate concentrated under reduced pressure. The residue was dissolved in dichloromethane (5 mL). Trifluoroacetic acid (1 mL) was added and the reaction was stirred at room temperature for 6 hr. The dichloromethane and trifluoroacetic acid were removed under vacuum. The residue was purified by prep-HPLC (gradient from 10% to 60% acetonitrile in water) to give the title compound (150 mg, 29% yield). $^1$H NMR (400 MHz, CD$_3$OD) δ 8.36 (d, J=8.3 Hz, 1H), 8.24 (s, 1H), 7.99 (d, J=8.0, 1H), 7.79-7.68 (m, 1H), 7.67 (s, 1H), 7.48 (t, J=7.7 Hz, 1H), 6.83 (s, 1H), 5.62 (s, 1H), 4.70-4.58 (m, 1H), 3.44-3.35 (m, 2H), 2.90-2.79 (m, 1H), 2.72-2.52 (m, 2H), 2.14 (s, 3H), 1.33 (d, J=6.1 Hz, 6H), 1.27 (d, J=6.9, 6H), 1.20-1.03 (m, 2H), 0.84-0.71 (m, 6H), 0.54-0.44 (m, 2H).

Example 8

Synthesis of 5-chloro-N$^2$-(4-((cis)-2,6-dicyclopropyl-1-methyl-1,2,3,6-tetrahydropyridin-4-yl)-2-isopropoxy-5-methylphenyl)-N$^4$-(2-(isopropylsulfonyl)phenyl)pyrimidine-2,4-diamine (Cpd. No. 16)

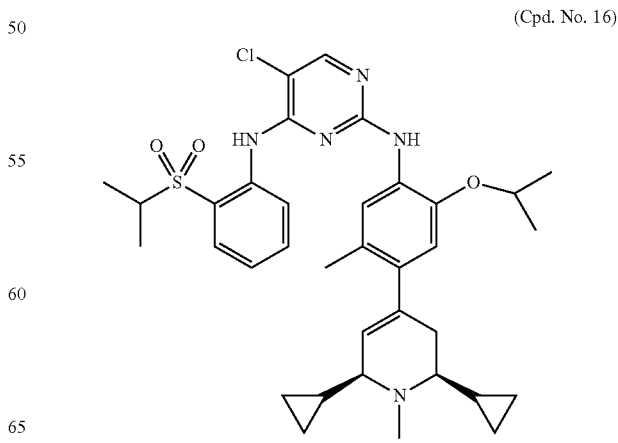

87

Step A: Synthesis of cis-2,6-dicyclopropyl-4-(5-isopropoxy-2-methyl-4-nitrophenyl)-1-methyl-1,2,3,6-tetrahydropyridine

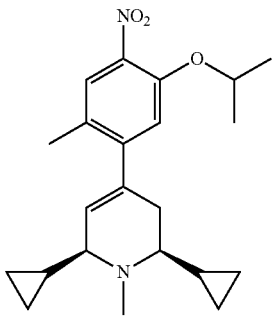 [SMILES: Cc1cc([N+](=O)[O-])c(OC(C)C)cc1C1=C[C@H](C2CC2)N(C)[C@H](C2CC2)C1]

To a solution of tert-butyl-cis-2,6-dicyclopropyl-4-(5-isopropoxy-2-methyl-4-nitrophenyl)-3,6-dihydropyridine-1(2H)-carboxylate (390 mg, 0.855 mmol) in dichloromethane (5 mL) was added trifluoroacetic acid (1 mL) and the reaction mixture was stirred at room temperature for 6 hr. The dichloromethane and trifluoroacetic acid were removed under vacuum and 100 mL of dichloromethane was added, washed with saturated NaHCO$_3$ solution. The water layer was extracted with dichloromethane for additional two times (100 mL each). The organic layers were combined, washed with brine, dried over Na$_2$SO$_4$ and evaporated. The residue was dissolved in dichloromethane (10 mL) and 37% formaldehyde (208 mg, 2.56 mmol), sodium triacetoxyborohydride (290 mg, 1.368 mmol) and acetic acid (82 mg, 1.368 mmol) were then added. The reaction was stirred at room temperature overnight. The reaction was quenched by adding water (80 mL), and extracted with dichloromethane (3×100 mL). The organic layers were combined, washed with brine, dried over Na$_2$SO$_4$, concentrated and purified by silica gel column chromatography with ethyl acetate/methanol (9/1, v/v) to afford the title compound (275 mg, 87% for two steps) as a yellow oil. MS m/z=371 (M+H).

Step B: Synthesis of 4-(cis-2,6-dicyclopropyl-1-methyl-1,2,3,6-tetrahydropyridin-4-yl)-2-isopropoxy-5-methylaniline

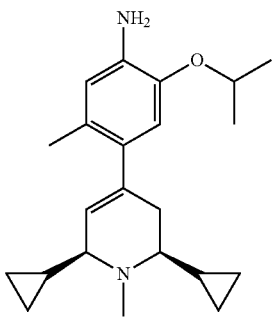

To a solution of cis-2,6-dicyclopropyl-4-(5-isopropoxy-2-methyl-4-nitrophenyl)-1-methyl-1,2,3,6-tetrahydropyridine (370 mg, 1.0 mmol) in 20 mL of ethanol was added several drops of 10% HCl, followed by iron powder (336 mg, 6.0 mmol). The mixture was stirred at 60° C. for 3 hr.

88

The reaction was cooled to room temperature and the iron powder was filtered off. Ethanol was removed under reduced pressure and the title compound was obtained as pale yellow oil. This product was used directly without further purification.

Step C: Synthesis of 5-chloro-N$^2$-(4-(cis-2,6-dicyclopropyl-1-methyl-1,2,3,6-tetrahydropyridin-4-yl)-2-isopropoxy-5-methylphenyl)-N$^4$-(2-(isopropylsulfonyl)phenyl) pyrimidine-2,4-diamine

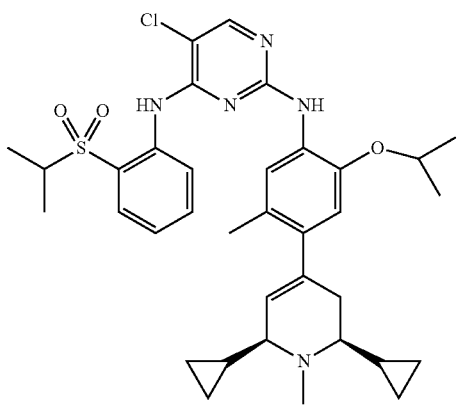 [SMILES: Cc1cc(Nc2ncc(Cl)c(Nc3ccccc3S(=O)(=O)C(C)C)n2)c(OC(C)C)cc1C1=C[C@H](C2CC2)N(C)[C@H](C2CC2)C1]

4-(Cis-2,6-dicyclopropyl-1-methyl-1,2,3,6-tetrahydropyridin-4-yl)-2-isopropoxy-5-methylaniline (270 mg, 0.794 mmol), 2,5-dichloro-N-(2-(isopropylsulfonyl)phenyl)pyrimidin-4-amine (274 mg, 0.794 mmol), Xantphos (46 mg, 0.0794 mmol), Pd(OAc)$_2$ (9 mg, 0.040 mmol), and Cs$_2$CO$_3$ (801 mg, 2.465 mmol) were dissolved in anhydrous THF (20 mL). N$_2$ was bubbled through the reaction mixture for 5 min, and then the reaction vessel was sealed and heated under microwave irradiation to 150° C. for 30 min. The mixture was filtered and the filtrate concentrated under reduced pressure. The residue was purified by prep-HPLC (gradient from 10% to 60% acetonitrile in water) to give the title compound (110 mg, 21% yield). MS m/z=650 (M+H).

Example 9

In Vitro Activity

H3122 and Kappas-299 cells were purchased from American Type Culture Collection (Manassas, Va., USA) and were used within 2 months after initiating from original stocks. All cell lines were cultured as recommended. For cell growth inhibition assay, cells were treated with different concentrations of the tested compounds, diluted from stock to culture media containing a 0.2% DMSO as the final concentration. Cell viability was determined using the WST-8 cell proliferation assay kit (Dojindo Molecular Technologies) according to manufacturer's instructions. Three independent experiments in triplicates were performed. Data were analyzed using Prism software to determine 50% of cell growth inhibition (IC$_{50}$) values versus DMSO control.

TABLE 4

| Cpd. No. | Inhibitory activity (nM) | H3122 (nM) (EML4-ALK) | Kappas-299 (nM) (NPM-ALK) |
|---|---|---|---|
| 1 | 1.8 | 92 | 30 |
| 2 | 4.4 | 132 | 39 |
| 5 | 0.85 | 27 | 13 |
| 9 | 1.1 | 54.9 | 35.9 |
| 10 | 0.98 | 54.9 | 37.5 |
| 15 | 6.6 | 196 | 121 |
| 16 | 6.3 | 160 | 97.7 |

Example 10

Inhibition of Wild-Type and Mutant ALK

The cytoplasmic domain (amino acid 1058-1620) of wild-type human ALK protein expressed as N-terminal GST-fusion protein was purchased from Carna Biosciences, Inc (Japan). Mutated ALK proteins were expressed in SF9 insect cells with N-terminal tags cleaved after purification. Kinase activities of all enzymes were assessed using a Lance® TR-FRET assay kit from Perkin Elmer Life Sciences (Waltham, Mass.). 2.5 µL of compound solution and 5 µL of protein solution were added into a black low volume 384 well microtiter plate which was incubated for 30 minutes with gentle shaking at room temperature, followed by adding 2.5 µL of fluorescently labeled peptide substrate (ULight™-IRS-1 (Tyr983) Peptide) and ATP mixture solution. The kinase reaction was performed in 50 mM HEPES (pH 7.5) with 1 mM EGTA, 1 mM $MgCl_2$, and 2 mM DTT, 0.01% Tween-20 added right before the assay. Final concentrations of ATP, substrates, and DMSO were 100 µM, 20 nM, and 0.5%, respectively. Concentrations of different ALK proteins were adjusted accordingly to achieve comparable enzymatic activities for both wild-type and all mutated ALK proteins. Final ALK concentrations were 1 nM, 1 nM, lnM, 128 nM, 2 nM, and 4 nM for wild-type, F1174L, L1196M, S1206Y, G1269A, and G1202R, respectively. The reaction was allowed to perform for 90 minutes in dark with gentle shaking at room temperature after which 10 µL of 20 mM EDTA and 2 nM Eu-W1024 anti-phosphotyrosine antibody (PT66) mixture solution in the detection buffer from the manufacturer was added to terminate the reaction and detect the phosphorylation of the peptide substrate. The final mixture was incubated in the dark for 1 hour before the plate was read on a Tecan Infinite M-1000 multi-mode plate reader (Tecan, Durham N.C.) with an excitation wavelength of 320 nm. Emission intensities were measured at both 620 and 665 nm with the intensity ratio between 665 and 620 nm corresponding to the peptide substrate phosphorylation. $IC_{50}$ values of inhibitors were obtained by fitting the ratio of 665/620 nm vs inhibitor concentrations in a sigmoidal dose-response curve (variable slope) with a non-linear regression. See Tables 5 and 6.

TABLE 5

| Enzyme | Cpd. No. 5 $IC_{50}$ (nM) |
|---|---|
| WT | 0.85 |
| F1197M | 3.3 |
| G1269A | 4.3 |
| L1196M | 0.73 |
| S1206Y | 1.3 |
| C1156Y | 0.82 (k) |
| V1180L | + (c) |
| F1174L | -- (c) |
| G1202R | 9.2 |

+ = active;
-- = inactive;
(c) = cell based assay;
(k) = KINOME scan

TABLE 6

| G1202R | Cpd. No. 5 | Crizotimb | Alectinib | Ceritinib | Lorlatinib | CJ-2360 |
|---|---|---|---|---|---|---|
| $IC_{50}$ (nM) | 9.2 | 46.2 | 34.7 | 11.5 ± 5.0 | 2.1 ± 0.4 | 119 |

Example 11

Kinase Activity

Cpd. No. 5 was screened for its activity against a panel of human kinases using the KINOMEscan™ screening platform from LeadHunter Discovery Services (currently DiscoverX Corporation (Fremont, Calif. 94538, United States). See Table 7.

TABLE 7

| Enzyme | Cpd. No. 5 $K_d$ (nM) |
|---|---|
| ROS1 | 0.73 |
| FAK | 5.4 |
| LTK | 0.62 |
| LRRK2 | 6.5 |
| LRRK2(G2019S) | 6.6 |
| FER | 11 |
| FES | 12 |
| IGF1R | 9 |
| INSR | 54 |
| INSRR | 32 |

Example 12

Pharmacokinetics

Routine pharmacokinetics studies were performed for Cpd. No. 5 in SD rats and beagle dogs. See Tables 8 and 9.

Example 13

In Vivo Efficacy

Drug Preparation
Cpd. Nos. 5 and 6 were dissolved in a solution of 98% PEG200: 2% TPGS (Sigma). LDK378 (ceritinib) is a known ALK inhibitor.
Cell Culture
Human lymphoma cells, KARPAS 299 were maintained at 37° C., 95% air, 5% carbon dioxide in RPMI 1640 medium supplemented with 10% Fetal Bovine Serum, 100 units/ml of penicillin and 100 units/ml of streptomycin (GIBCO™, Invitrogen Corp.) and passaged twice weekly.

Xenograft Tumor Cell Injection

Tumor cells for xenografts were washed twice in PBS, and re-suspended in an ice cold mixture of 1:1 PBS and Matrigel (BD Biosciences, Invitrogen Corp.) for a final Matrigel protein concentration of 5 mg/ml. Cells at $5\times10^6$ cells in 0.1 ml were injected subcutaneously (s.c.) into the flank region of each mouse. All tumors were inoculated into SCID mice (strain:236 C.B-17 SCID, Charles River).

Xenograft Tumor Growth and Weight Monitoring

The size of tumors growing in the mice was measured in two dimensions using calipers. Tumor volume (mm$^3$)= (AxB$^2$)/2 where A and B are the tumor length and width (in mm), respectively. During treatment, tumor volume and body weight were measured three times a week. After the treatment was stopped, tumor volume and body weight was measured at least once a week.

Assessment of Toxicity and End Point

Tumors were not allowed to exceed 10% of the animal's total body weight. If an animal had two or more tumors the total weight of all tumors were not allowed to exceed 10% of the animal's total body weight. At the end of the experimental period or when tumor size approached 10% of the total body weight, the animal was euthanized. Animals that showed profound morbidity or a weight loss of over 20% of body weight were euthanized.

Determination of In Vivo Antitumor Efficacy

Before treatment began, tumors were allowed to grow to an average of 150 mm$^3$ (70-270 mm$^3$) in volume, at which point the blood vessel supplies to the tumor should have been well established. Mice with tumors within acceptable size range were randomized into treatment groups of 7 mice. Drug was given orally, once daily for 3 weeks. The Control group received vehicle alone. See FIG. 1.

What is claimed is:

1. A compound having Formula I:

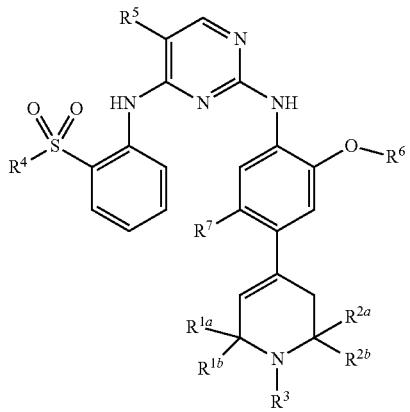

or a pharmaceutically acceptable salt or solvate thereof, wherein:

$R^{1a}$ and $R^{1b}$ are independently selected from the group consisting of hydrogen, $C_{1-6}$ alkyl, and $C_{3-8}$ cycloalkyl;

$R^{2a}$ and $R^{2b}$ are independently selected from the group consisting of hydrogen, $C_{1-6}$ alkyl, and $C_{3-8}$ cycloalkyl;

$R^3$ is selected from the group consisting of hydrogen, $C_{1-6}$ alkyl, $C_{3-6}$ cycloalkyl, and $C_{4-8}$ heterocyclo, $R^4$ is selected from the group consisting of $C_{1-4}$ alkyl, and $C_{3-6}$ cycloalkyl;

$R^5$ is halo;

TABLE 8

| Compound | Dose (mg/kg) IV | Dose (mg/kg) PO | Tmax (h) IV | Tmax (h) PO | Cmax(ng/mL) IV | Cmax(ng/mL) PO | AUC0-t (ng·h/mL) IV | AUC0-t (ng·h/mL) PO | AUC0-∞ (ng·h/mL) IV | AUC0-∞ (ng·h/mL) PO | $t_{1/2}$ (h) IV | $t_{1/2}$ (h) PO | CL (iv) (L/h/kg) | $V_{ss}$ (iv) (L/kg) | MRT$_{INF}$ (iv)(h) | F(AUC0-t) |
|---|---|---|---|---|---|---|---|---|---|---|---|---|---|---|---|---|
| Cpd. No. 5 (solution) | 1 | 10 | 0.083 | 2.67 | 234 | 153 | 506 | 1759 | 576 | 1788 | 3.94 | 3.93 | 1.75 | 7.97 | 4.54 | 31.1% |
| Cpd. No. 5 (suspension) |  | 10 |  | 3.67 |  | 75.9 |  | 719 |  | 733 |  | 4.05 |  |  |  | 12.7 |
| Cpd. No. 5 (mesylate) |  | 10 |  | 1.0 |  | 127 |  | 958 |  | 971 |  | 3.84 |  |  |  | 16.9 |

TABLE 9

| Compound | Dose (mg/kg) IV | Dose (mg/kg) PO | Tmax (h) IV | Tmax (h) PO | Cmax(ng/mL) IV | Cmax(ng/mL) PO | AUC0-t (ng·h/mL) IV | AUC0-t (ng·h/mL) PO | AUC0-∞ (ng·h/mL) IV | AUC0-∞ (ng·h/mL) PO | $t_{1/2}$ (h) IV | $t_{1/2}$ (h) PO | CL (iv) (L/h/kg) | $V_{ss}$ (iv) (L/kg) | MRT$_{INF}$ (iv)(h) | F(AUC0-t) |
|---|---|---|---|---|---|---|---|---|---|---|---|---|---|---|---|---|
| Cpd. No. 5 | 1 | 5 | 0.083 | 1.67 | 314 | 239 | 1821 | 2929 | 2137 | 3711 | 19.7 | 20.0 | 0.486 | 10.8 | 22.1 | 33.3% |

It is to be understood that the foregoing embodiments and exemplifications are not intended to be limiting in any respect to the scope of the disclosure, and that the claims presented herein are intended to encompass all embodiments and exemplifications whether or not explicitly presented herein All patents and publications cited herein are fully incorporated by reference in their entirety.

$R^6$ is selected from the group consisting of $C_{1-4}$ alkyl, and $C_{3-6}$ cycloalkyl; and $R^7$ is selected from the group consisting of hydrogen, $C_{1-4}$ alkyl, and $C_{3-6}$ cycloalkyl, with proviso that when $R^{1a}$, $R^{1b}$, $R^{2a}$, and $R^{2b}$ are each hydrogen, then $R^3$ is selected from the group consisting of $C_{3-6}$ cycloalkyl and $C_{4-8}$ heterocyclo.

2. The compound of claim 1 having Formula II:

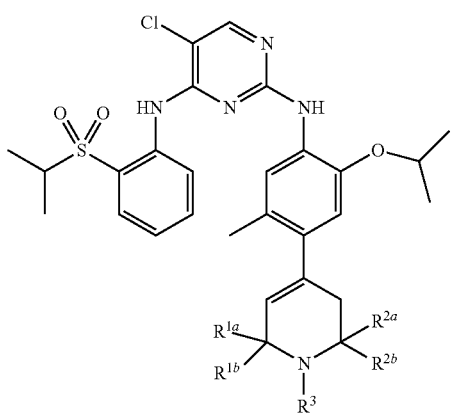

or a pharmaceutically acceptable salt or solvate thereof, wherein:

$R^{1a}$ and $R^{1b}$ are independently selected from the group consisting of hydrogen, $C_{1-4}$ alkyl, and $C_{3-6}$ cycloalkyl;

$R^{2a}$ and $R^{2b}$ are independently selected from the group consisting of hydrogen, $C_{1-4}$ alkyl, and $C_{3-6}$ cycloalkyl; and $R^3$ is selected from the group consisting of hydrogen, $C_{1-4}$ alkyl, $C_{3-6}$ cycloalkyl, and $C_{4-8}$ heterocyclo.

3. The compound of claim 2, or a pharmaceutically acceptable salt or solvate thereof, wherein $R^{1b}$ and $R^{2b}$ are each hydrogen.

4. The compound of claim 3, or a pharmaceutically acceptable salt or solvate thereof, wherein $R^{1a}$ and $R^{2a}$ are each hydrogen.

5. The compound of claim 2, or a pharmaceutically acceptable salt or solvate thereof, having Formula III:

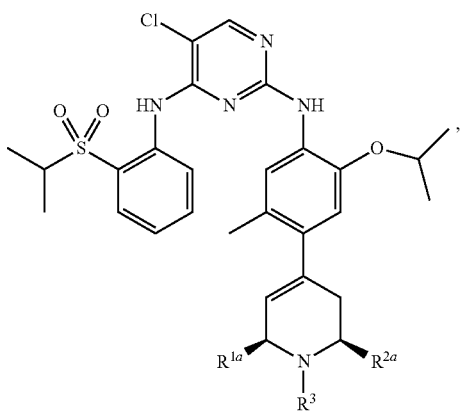

wherein:

$R^{1a}$ and $R^{2a}$ are each independently selected from the group consisting of $C_{1-4}$ alkyl, and $C_{3-6}$ cycloalkyl; and the compound has an enantiomeric excess of 90% or more.

6. The compound of claim 2, or a pharmaceutically acceptable salt or solvate thereof, having Formula IV:

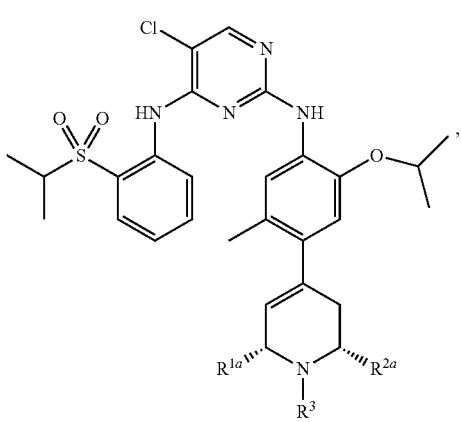

wherein:

$R^{1a}$ and $R^{2a}$ are each independently selected from the group consisting of $C_{1-4}$ alkyl, and $C_{3-6}$ cycloalkyl; and the compound has an enantiomeric excess of 90% or more.

7. The compound of claim 2, or a pharmaceutically acceptable salt or solvate thereof, having Formula V:

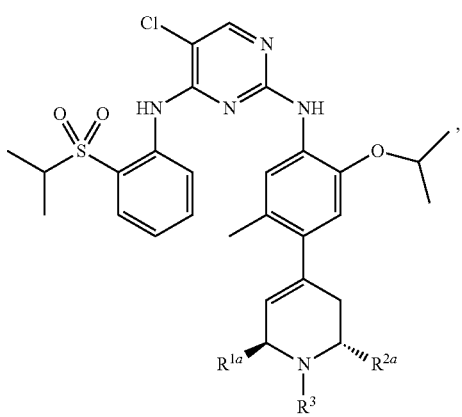

wherein:

$R^{1a}$ and $R^{2a}$ are each independently selected from the group consisting of $C_{1-4}$ alkyl, and $C_{3-6}$ cycloalkyl; and the compound has an enantiomeric excess of 90% or more.

8. The compound of claim 2, or a pharmaceutically acceptable salt or solvate thereof, having Formula VI:

$$\text{VI}$$

wherein:
R$^{1a}$ and R$^{2a}$ are each independently selected from the group consisting of C$_{1-4}$ alkyl, and C$_{3-6}$ cycloalkyl; and
the compound has an enantiomeric excess of 90% or more.

9. The compound of claim 2, or a pharmaceutically acceptable salt or solvate thereof, wherein R$^{1a}$ and R$^{2a}$ are each methyl.

10. The compound of claim 2, or a pharmaceutically acceptable salt or solvate thereof, wherein R$^{1a}$ and R$^{2a}$ are each cyclopropyl.

11. The compound of claim 2, or a pharmaceutically acceptable salt or solvate thereof, wherein R$^3$ is selected from the group consisting of:

and

12. The compound of claim 1, or a pharmaceutically acceptable salt or hydrate thereof, selected from the group consisting of:
5-chloro-N$^2$-(2-isopropoxy-5-methyl-4-(1,2,2,6,6-pentamethyl-1,2,3,6-tetrahydropyridin-4-yl)phenyl)-N$^4$-(2-(isopropylsulfonyl)phenyl)pyrimidine-2,4-diamine;
5-chloro-N$^2$-(2-isopropoxy-5-methyl-4-(2,2,6,6-tetramethyl-1,2,3,6-tetrahydropyridin-4-yl)phenyl)-N$^4$-(2-(isopropylsulfonyl)phenyl)pyrimidine-2,4-diamine;
5-chloro-N$^2$-(4-((cis)-2,6-diethyl-1,2,3,6-tetrahydropyridin-4-yl)-2-isopropoxy-5-methylphenyl)-N$^4$-(2-(isopropylsulfonyl)phenyl)pyrimidine-2,4-diamine;
5-chloro-N$^2$-(4-((cis)-2,6-diethyl-1-methyl-1,2,3,6-tetrahydropyridin-4-yl)-2-isopropoxy-5-methylphenyl)-N$^4$-(2-(isopropylsulfonyl)phenyl)pyrimidine-2,4-diamine;
5-chloro-N$^2$-(2-isopropoxy-5-methyl-4-(1-(tetrahydro-2H-pyran-4-yl)-1,2,3,6-tetrahydropyridin-4-yl)phenyl)-N$^4$-(2-(isopropylsulfonyl)phenyl)pyrimidine-2,4-diamine;
5-chloro-N$^2$-(2-isopropoxy-5-methyl-4-(1-(oxetan-3-yl)-1,2,3,6-tetrahydropyridin-4-yl)phenyl)-N$^4$-(2-(isopropylsulfonyl)phenyl)pyrimidine-2,4-diamine;
5-chloro-N$^2$-(4-((cis)-2,6-dicyclobutyl-1,2,3,6-tetrahydropyridin-4-yl)-2-isopropoxy-5-methylphenyl)-N$^4$-(2-(isopropylsulfonyl)phenyl)pyrimidine-2,4-diamine;
5-chloro-N$^2$-(4-((cis)-2,6-dicyclobutyl-1-methyl-1,2,3,6-tetrahydropyridin-4-yl)-2-isopropoxy-5-methylphenyl)-N$^4$-(2-(isopropylsulfonyl)phenyl)pyrimidine-2,4-diamine;
5-chloro-N$^2$-(4-((cis)-2,6-dimethyl-1,2,3,6-tetrahydropyridin-4-yl)-2-isopropoxy-5-methylphenyl)-N$^4$-(2-(isopropylsulfonyl)phenyl)pyrimidine-2,4-diamine;
5-chloro-N$^2$-(2-isopropoxy-5-methyl-4-((cis)-1,2,6-trimethyl-1,2,3,6-tetrahydropyridin-4-yl)phenyl)-N$^4$-(2-(isopropylsulfonyl)phenyl)pyrimidine-2,4-diamine;
5-chloro-N$^2$-(4-((trans)-2,6-diethyl-1,2,3,6-tetrahydropyridin-4-yl)-2-isopropoxy-5-methylphenyl)-N$^4$-(2-(isopropylsulfonyl)phenyl)pyrimidine-2,4-diamine;
5-chloro-N$^2$-(4-((trans)-2,6-diethyl-1-methyl-1,2,3,6-tetrahydropyridin-4-yl)-2-isopropoxy-5-methylphenyl)-N$^4$-(2-(isopropylsulfonyl)phenyl)pyrimidine-2,4-diamine;
5-chloro-N$^2$-(4-((trans)-2,6-dimethyl-1,2,3,6-tetrahydropyridin-4-yl)-2-isopropoxy-5-methylphenyl)-N$^4$-(2-(isopropylsulfonyl)phenyl)pyrimidine-2,4-diamine;
5-chloro-N$^2$-(2-isopropoxy-5-methyl-4-((trans)-1,2,6-trimethyl-1,2,3,6-tetrahydropyridin-4-yl)phenyl)-N$^4$-(2-(isopropylsulfonyl)phenyl)pyrimidine-2,4-diamine;
5-chloro-N$^2$-(4-((cis)-2,6-dicyclopropyl-1,2,3,6-tetrahydropyridin-4-yl)-2-isopropoxy-5-methylphenyl)-N$^4$-(2-(isopropylsulfonyl)phenyl)pyrimidine-2,4-diamine;
5-chloro-N$^2$-(4-((cis)-2,6-dicyclopropyl-1-methyl-1,2,3,6-tetrahydropyridin-4-yl)-2-isopropoxy-5-methylphenyl)-N$^4$-(2-(isopropylsulfonyl)phenyl)pyrimidine-2,4-diamine;
5-chloro-N$^2$-(4-((trans)-2,6-dicyclopropyl-1,2,3,6-tetrahydropyridin-4-yl)-2-isopropoxy-5-methylphenyl)-N$^4$-(2-(isopropylsulfonyl)phenyl)pyrimidine-2,4-diamine;
5-chloro-N$^2$-(4-((trans)-2,6-dicyclopropyl-1-methyl-1-1,2,3,6-tetrahydropyridin-4-yl)-2-isopropoxy-5-methylphenyl)-N$^4$-(2-(isopropylsulfonyl)phenyl)pyrimidine-2,4-diamine;
5-chloro-N$^2$-(4-((cis)-2,6-dimethyl-1-(tetrahydro-2H-pyran-4-yl)-1,2,3,6-tetrahydropyridin-4-yl)-2-isopropoxy-5-methylphenyl)-N$^4$-(2-(isopropylsulfonyl) phenyl) pyrimidine-2,4-diamine;
5-chloro-N$^2$-(4-((cis)-2,6-dimethyl-1-(oxetan-3-yl)-1,2,3,6-tetrahydropyridin-4-yl)-2-isopropoxy-5-methylphenyl)-N$^4$-(2-(isopropylsulfonyl)phenyl)pyrimidine-2,4-diamine;
5-chloro-N$^2$-(4-((trans)-2,6-diethyl-1-(tetrahydro-2H-pyran-4-yl)-1,2,3,6-tetrahydropyridin-4-yl)-2-isopropoxy-5-methylphenyl)-N$^4$-(2-(isopropylsulfonyl) phenyl) pyrimidine-2,4-diamine;
5-chloro-N$^2$-(4-((2S,6S)-2,6-diethyl-1-(oxetan-3-yl)-1,2,3,6-tetrahydropyridin-4-yl)-2-isopropoxy-5-methylphenyl)-N$^4$-(2-(isopropylsulfonyl)phenyl)pyrimidine-2,4-diamine;
5-chloro-NM-(4-((trans)-2,6-dimethyl-1-(tetrahydro-2H-pyran-4-yl)-1,2,3,6-tetrahydropyridin-4-yl)-2-isopropoxy-5-methylphenyl)-N$^4$-(2-(isopropylsulfonyl) phenyl) pyrimidine-2,4-diamine;

5-chloro-N\M-(4-((trans)-2,6-dimethyl-1-(oxetan-3-yl)-1,2,3,6-tetrahydropyridin-4-yl)-2-isopropoxy-5-methylphenyl)-N$^4$-(2-(isopropylsulfonyl)phenyl)pyrimidine-2,4-diamine 5-chloro-N$^2$-(4-((cis)-2,6-dicyclopropyl-1-(tetrahydro-2H-pyran-4-yl)-1,2,3,6-tetrahydropyridin-4-yl)-2-isopropoxy-5-methylphenyl)-N$^4$-(2-(isopropylsulfonyl)phenyl) pyrimidine-2,4-diamine;

5-chloro-N$^2$-(4-((cis)-2,6-dicyclopropyl-1-(oxetan-3-yl)-1,2,3,6-tetrahydropyridin-4-yl)-2-isopropoxy-5-methylphenyl)-N$^4$-(2-(isopropylsulfonyl)phenyl)pyrimidine-2,4-diamine;

5-chloro-N$^2$-(4-((trans)-2,6-dicyclobutyl-1-(tetrahydro-2H-pyran-4-yl)-1,2,3,6-tetrahydropyridin-4-yl)-2-isopropoxy-5-methylphenyl)-N-(2-(isopropylsulfonyl)phenyl) pyrimidine-2,4-diamine;

5-chloro-N$^2$-(4-((trans)-2,6-dicyclobutyl-1-(oxetan-3-yl)-1,2,3,6-tetrahydropyridin-4-yl)-2-isopropoxy-5-methylphenyl)-N-(2-(isopropylsulfonyl)phenyl)pyrimidine-2,4-diamine;

5-chloro-N$^2$-(4-((trans)-2,6-dicyclopropyl-1-(tetrahydro-2H-pyran-4-yl)-1,2,3,6-tetrahydropyridin-4-yl)-2-isopropoxy-5-methylphenyl)-N$^2$-(2-(isopropylsulfonyl)phenyl) pyrimidine-2,4-diamine;

5-chloro-N$^2$-(4-((trans)-2,6-dicyclopropyl-1-(oxetan-3-yl)-1,2,3,6-tetrahydropyridin-4-yl)-2-isopropoxy-5-methylphenyl)-N-(2-(isopropylsulfonyl)phenyl)pyrimidine-2,4-diamine;

5-chloro-N$^2$-(4-((2S,6R)-2,6-dimethyl-1,2,3,6-tetrahydropyridin-4-yl)-2-isopropoxy-5-methylphenyl)-N$^4$-(2-(isopropylsulfonyl)phenyl)pyrimidine-2,4-diamine;

5-chloro-N$^2$-(2-isopropoxy-5-methyl-4-((2S,6R)-1,2,6-trimethyl-1,2,3,6-tetrahydropyridin-4-yl)phenyl)-N$^4$-(2-(isopropylsulfonyl)phenyl)pyrimidine-2,4-diamine;

5-chloro-N$^2$-(4-((2R,6R)-2,6-dicyclopropyl-1,2,3,6-tetrahydropyridin-4-yl)-2-isopropoxy-5-methylphenyl)-N$^4$-(2-(isopropylsulfonyl)phenyl)pyrimidine-2,4-diamine;

5-chloro-N$^2$-(4-((2R,6R)-2,6-dicyclopropyl-1-methyl-1,2,3,6-tetrahydropyridin-4-yl)-2-isopropoxy-5-methylphenyl)-N$^4$-(2-(isopropylsulfonyl)phenyl)pyrimidine-2,4-diamine;

5-chloro-N$^2$-(4-((2R,6S)-2,6-dimethyl-1,2,3,6-tetrahydropyridin-4-yl)-2-isopropoxy-5-methylphenyl)-N$^4$-(2-(isopropylsulfonyl)phenyl)pyrimidine-2,4-diamine;

5-chloro-N$^2$-(2-isopropoxy-5-methyl-4-((2R,6S)-1,2,6-trimethyl-1,2,3,6-tetrahydropyridin-4-yl)phenyl)-N$^4$-(2-(isopropylsulfonyl)phenyl)pyrimidine-2,4-diamine;

5-chloro-N$^2$-(4-((2S,6S)-2,6-dimethyl-1,2,3,6-tetrahydropyridin-4-yl)-2-isopropoxy-5-methylphenyl)-N$^4$-(2-(isopropylsulfonyl)phenyl)pyrimidine-2,4-diamine;

5-chloro-N$^2$-(2-isopropoxy-5-methyl-4-((2S,6S)-1,2,6-trimethyl-1,2,3,6-tetrahydropyridin-4-yl)phenyl)-N$^4$-(2-(isopropylsulfonyl)phenyl)pyrimidine-2,4-diamine;

5-chloro-N$^2$-(4-((2R,6R)-2,6-dimethyl-1,2,3,6-tetrahydropyridin-4-yl)-2-isopropoxy-5-methylphenyl)-N$^4$-(2-(isopropylsulfonyl)phenyl)pyrimidine-2,4-diamine;

5-chloro-N$^2$-(2-isopropoxy-5-methyl-4-((2R,6R)-1,2,6-timethyl-1,2,3,6-tetrahydropyridin-4-yl)phenyl)-N$^4$-(2-(isopropylsulfonyl)phenyl)pyrimidine-2,4-diamine;

5-chloro-N$^2$-(4-((2S,6S)-2,6-dicyclopropyl-1,2,3,6-tetrahydropyridin-4-yl)-2-isopropoxy-5-methylphenyl)-N$^4$-(2-(isopropylsulfonyl)phenyl)pyrimidine-2,4-diamine;

5-chloro-N$^2$-(4-((2S,6S)-2,6-dicyclopropyl-1-methyl-1,2,3,6-tetrahydropyridin-4-yl)-2-isopropoxy-5-methylphenyl)-N$^4$-(2-(isopropylsulfonyl)phenyl)pyrimidine-2,4-diamine;

5-chloro-N$^2$-(4-((2R,6S)-2,6-dicyclopropyl-1,2,3,6-tetrahydropyridin-4-yl)-2-isopropoxy-5-methylphenyl)-N$^4$-(2-(isopropylsulfonyl)phenyl)pyrimidine-2,4-diamine;

5-chloro-N$^2$-(4-((2R,6S)-2,6-dicyclopropyl-1-methyl-1,2,3,6-tetrahydropyridin-4-yl)-2-isopropoxy-5-methylphenyl)-N$^4$-(2-(isopropylsulfonyl)phenyl)pyrimidine-2,4-diamine;

5-chloro-N$^2$-(4-((2S,6R)-2,6-dicyclopropyl-1,2,3,6-tetrahydropyridin-4-yl)-2-isopropoxy-5-methylphenyl)-N$^4$-(2-(isopropylsulfonyl)phenyl)pyrimidine-2,4-diamine;

5-chloro-N$^2$-(4-((2S,6R)-2,6-dicyclopropyl-1-methyl-1,2,3,6-tetrahydropyridin-4-yl)-2-isopropoxy-5-methylphenyl)-N$^4$-(2-(isopropylsulfonyl)phenyl)pyrimidine-2,4-diamine;

5-chloro-N$^2$-(4-((2R,6S)-2,6-dimethyl-1-(tetrahydro-2H-pyran-4-yl)-1,2,3,6-tetrahydropyridin-4-yl)-2-isopropoxy-5-methylphenyl)-N$^4$-(2-(isopropylsulfonyl)phenyl) pyrimidine-2,4-diamine;

5-chloro-N$^2$-(4-((2R,6S)-2,6-dimethyl-1-(oxetan-3-yl)-1,2,3,6-tetrahydropyridin-4-yl)-2-isopropoxy-5-methylphenyl)-N$^4$-(2-(isopropylsulfonyl)phenyl)pyrimidine-2,4-diamine;

5-chloro-N$^2$-(4-((2S,6S)-2,6-dimethyl-1-(tetrahydro-2H-pyran-4-yl)-1,2,3,6-tetrahydropyridin-4-yl)-2-isopropoxy-5-methylphenyl)-N$^2$-(2-(isopropylsulfonyl)phenyl) pyrimidine-2,4-diamine;

5-chloro-N$^2$-(4-((2S,6S)-2,6-dimethyl-1-(oxetan-3-yl)-1,2,3,6-tetrahydropyridin-4-yl)-2-isopropoxy-5-methylphenyl)-N$^4$-(2-(isopropylsulfonyl)phenyl)pyrimidine-2,4-diamine;

5-chloro-N$^2$-(4-((2R,6R)-2,6-dimethyl-1-(tetrahydro-2H-pyran-4-yl)-1,2,3,6-tetrahydropyridin-4-yl)-2-isopropoxy-5-methylphenyl)-N$^2$-(2-(isopropylsulfonyl)phenyl) pyrimidine-2,4-diamine;

5-chloro-N$^2$-(4-((2R,6R)-2,6-dimethyl-1-(oxetan-3-yl)-1,2,3,6-tetrahydropyridin-4-yl)-2-isopropoxy-5-methylphenyl)-N-(2-(isopropylsulfonyl)phenyl)pyrimidine-2,4-diamine;

5-chloro-N$^2$-(4-((2S,6S)-2,6-dicyclopropyl-1-(tetrahydro-2H-pyran-4-yl)-1,2,3,6-tetrahydropyridin-4-yl)-2-isopropoxy-5-methylphenyl)-N$^4$-(2-(isopropylsulfonyl)phenyl) pyrimidine-2,4-diamine;

5-chloro-N$^2$-(4-((2S,6S)-2,6-dicyclopropyl-1-(oxetan-3-yl)-1,2,3,6-tetrahydropyridin-4-yl)-2-isopropoxy-5-methylphenyl)-N$^4$-(2-(isopropylsulfonyl)phenyl)pyrimidine-2,4-diamine;

5-chloro-N$^2$-(4-((2R,6S)-2,6-dicyclopropyl-1-(tetrahydro-2H-pyran-4-yl)-1,2,3,6-tetrahydropyridin-4-yl)-2-isopropoxy-5-methylphenyl)-N$^4$-(2-(isopropylsulfonyl)phenyl) pyrimidine-2,4-diamine;

5-chloro-N$^2$-(4-((2R,6S)-2,6-dicyclopropyl-1-(oxetan-3-yl)-1,2,3,6-tetrahydropyridin-4-yl)-2-isopropoxy-5-methylphenyl)-N$^4$-(2-(isopropylsulfonyl)phenyl)pyrimidine-2,4-diamine;

5-chloro-N$^2$-(4-((2S,6R)-2,6-dicyclopropyl-1-(tetrahydro-2H-pyran-4-yl)-1,2,3,6-tetrahydropyridin-4-yl)-2-isopropoxy-5-methylphenyl)-N$^4$-(2-(isopropylsulfonyl)phenyl) pyrimidine-2,4-diamine; and 5-chloro-N$^2$-(4-((2S,6R)-2,6-dicyclopropyl-1-(oxetan-3-yl)-1,2,3,6-tetrahydropyridin-4-yl)-2-isopropoxy-5-methylphenyl)-N$^4$-(2-(isopropylsulfonyl)phenyl)pyrimidine-2,4-diamine.

13. The compound of claim 12, or a pharmaceutically acceptable salt or hydrate thereof, which is 5-chloro-N$^2$-(2-isopropoxy-5-methyl-4-(1-(tetrahydro-2H-pyran-4-yl)-1,2,3,6-tetrahydropyridin-4-yl)phenyl)-N$^4$-(2-(isopropylsulfonyl)phenyl)pyrimidine-2,4-diamine.

14. A pharmaceutical composition comprising the compound of claim 1, or a pharmaceutically acceptable salt or hydrate thereof, and a pharmaceutically acceptable carrier.

* * * * *

UNITED STATES PATENT AND TRADEMARK OFFICE
CERTIFICATE OF CORRECTION

PATENT NO. : 10,709,705 B2
APPLICATION NO. : 15/559445
DATED : July 14, 2020
INVENTOR(S) : Shaomeng Wang et al.

It is certified that error appears in the above-identified patent and that said Letters Patent is hereby corrected as shown below:

In the Claims

At Column 92, Line 30, "heterocyclo," should be -- heterocyclo; --.

At Column 94, Lines 40-55, " 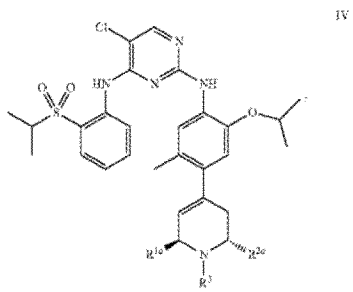 " should be 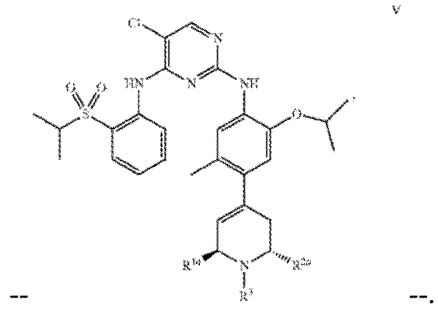 -- --.

At Column 96, Line 44, "methyl-1-1," should be -- methyl-1 --.

At Column 96, Line 64, "5-chloro-NM-" should be -- 5-chloro-$N^2$- --.

At Column 97, Line 1, "5-chloro-NM-" should be -- 5-chloro-$N^2$- --.

At Column 97, Line 4, "4-diamine" should be -- 4-diamine; --.

Signed and Sealed this
First Day of December, 2020

Andrei Iancu
*Director of the United States Patent and Trademark Office*

CERTIFICATE OF CORRECTION (continued)
U.S. Pat. No. 10,709,705 B2

At Column 97, Line 16, "-N-" should be -- $-N^4-$ --.

At Column 97, Line 20, "-N-" should be -- $-N^4-$ --.

At Column 97, Line 24, "-$N^2$-" should be -- $-N^4-$ --.

At Column 97, Line 28, "-N-" should be -- $-N^4-$ --.

At Column 97, Line 59, "timethyl-1," should be -- trimethyl-1, --.

At Column 98, Line 7, "4-diamine" should be -- 4-diamine; --.

At Column 98, Line 25, "-$N^2$-" should be -- $-N^4-$ --.

At Column 98, Line 33, "-$N^2$-" should be -- $-N^4-$ --.

At Column 98, Line 37, "-N-" should be -- $-N^4-$ --.